(12) United States Patent  
Müller et al.

(10) Patent No.: US 11,872,379 B2  
(45) Date of Patent: Jan. 16, 2024

(54) DRUG DELIVERY DEVICE

(71) Applicant: Haselmeier AG, St. Gallen (CH)

(72) Inventors: Heiko Müller, Stuttgart (DE); Wouter Reubzaet, Brunssum (NL); André Hild, Aachen (DE)

(73) Assignee: MEDMIX SWITZERLAND AG, Haag (CH)

( * ) Notice: Subject to any disclaimer, the term of this patent is extended or adjusted under 35 U.S.C. 154(b) by 214 days.

(21) Appl. No.: 17/472,550

(22) Filed: Sep. 10, 2021

(65) Prior Publication Data

US 2022/0323684 A1 Oct. 13, 2022

(30) Foreign Application Priority Data

Apr. 7, 2021 (EP) .................................. 21167293  
Jun. 25, 2021 (EP) .................................. 21181883  
(Continued)

(51) Int. Cl.  
*A61M 5/315* (2006.01)  
*A61M 5/19* (2006.01)  
(Continued)

(52) U.S. Cl.  
CPC .......... *A61M 5/31543* (2013.01); *A61M 5/19* (2013.01); *A61M 5/3153* (2013.01);  
(Continued)

(58) Field of Classification Search  
CPC ................ A61M 5/31543; A61M 5/19; A61M 5/31501; A61M 5/31511; A61M 5/3153;  
(Continued)

(56) References Cited

U.S. PATENT DOCUMENTS 5,147,328 A 9/1992 Dragosits et al.  
5,693,027 A 12/1997 Hansen et al.  
(Continued)

FOREIGN PATENT DOCUMENTS

CN 106470716 A 3/2017  
EP 1 920 794 A1 5/2008  
(Continued)

OTHER PUBLICATIONS

International Search Report and Written Opinion dated Aug. 10, 2022 in corresponding International Application No. PCT/EP2022/059335.  
(Continued)

*Primary Examiner* — Dung T Ulsh  
(74) *Attorney, Agent, or Firm* — GLOBAL IP COUNSELORS, LLP

(57) ABSTRACT

A drug delivery device with a housing configured to connect to a dispensing unit including a compartment containing a fluid, a piston rod configured to move in a proximal direction for ejecting the fluid, and a dosing mechanism including an actuation member to be actuated by a user. The device includes a conversion mechanism configured to convert a movement of the actuation member to a movement of the piston rod. The conversion mechanism includes a dose selector member, which is rotationally fixed to the housing and axially movable with respect to the housing, and a dosing member, which is rotationally movable with respect to the dose selector member. The drug delivery device includes a friction reduction mechanism provided between the dose selector member and the dosing member to reduce friction between the dose selector member and the dosing member.

18 Claims, 54 Drawing Sheets

(30) Foreign Application Priority Data

Jun. 25, 2021 (EP) .................................... 21181887
Jul. 8, 2021 (EP) .................................... 21184545

(51) Int. Cl.
*A61M 5/34* (2006.01)
*A61M 5/31* (2006.01)

(52) U.S. Cl.
CPC .... *A61M 5/31501* (2013.01); *A61M 5/31511* (2013.01); *A61M 5/31536* (2013.01); *A61M 5/31551* (2013.01); *A61M 5/348* (2013.01); *A61M 2005/3126* (2013.01); *A61M 2005/3151* (2013.01); *A61M 2005/3154* (2013.01); *A61M 2205/581* (2013.01); *A61M 2205/582* (2013.01)

(58) Field of Classification Search
CPC .......... A61M 5/31536; A61M 5/31551; A61M 5/348; A61M 5/3155; A61M 5/31568; A61M 5/3158; A61M 5/31563; A61M 5/2422; A61M 5/31585; A61M 5/31593; A61M 5/24; A61M 2005/3126; A61M 2005/3151; A61M 2005/3154; A61M 2005/244; A61M 2005/2407; A61M 2005/2488; A61M 2205/581; A61M 2205/582; A61M 2205/0222; A61M 2205/60

See application file for complete search history.

(56) References Cited

U.S. PATENT DOCUMENTS

| | | | |
|---|---|---|---|
| 5,785,048 | A | 7/1998 | Koerner |
| 6,126,646 | A | 10/2000 | Hansen et al. |
| 6,648,859 | B2 | 11/2003 | Bitdinger et al. |
| 8,491,538 | B2 | 7/2013 | Kohlbrenner et al. |
| 9,180,251 | B2 | 11/2015 | Avery |
| 9,205,196 | B2 | 12/2015 | Harms et al. |
| 9,717,859 | B2 | 8/2017 | Harms et al. |
| 10,092,699 | B2 | 10/2018 | Jugl et al. |
| 10,350,361 | B2 | 7/2019 | Stephenson et al. |
| 2003/0109834 | A2 | 6/2003 | Bitdinger et al. |
| 2009/0275916 | A1 | 11/2009 | Harms et al. |
| 2010/0168677 | A1 | 7/2010 | Gabriel et al. |
| 2013/0090602 | A1 | 4/2013 | Avery et al. |
| 2014/0350484 | A1* | 11/2014 | Kohlbrenner ..... A61M 5/31583 604/222 |
| 2015/0202370 | A1 | 7/2015 | Jugl et al. |
| 2015/0224266 | A1 | 8/2015 | Pumpltre et al. |
| 2016/0058941 | A1 | 3/2016 | Wu et al. |
| 2016/0317751 | A1 | 11/2016 | Andersen |
| 2017/0098058 | A1 | 4/2017 | McCullough et al. |
| 2017/0266387 | A1 | 9/2017 | Keitel et al. |
| 2019/0117898 | A1* | 4/2019 | Hirschel ........... A61M 5/31585 |
| 2019/0184092 | A1 | 6/2019 | Sjolund et al. |
| 2020/0018861 | A1 | 1/2020 | Bryson et al. |
| 2020/0101229 | A1* | 4/2020 | Plambech ......... A61M 5/31585 |
| 2020/0345945 | A1 | 11/2020 | Jugl et al. |
| 2020/0376205 | A1* | 12/2020 | Keitel ..................... A61M 5/24 |
| 2021/0361876 | A1* | 11/2021 | Dahmen ........... A61M 5/31551 |
| 2023/0181836 | A1* | 6/2023 | Quinn ............... A61M 5/31553 604/209 |

FOREIGN PATENT DOCUMENTS

| | | |
|---|---|---|
| EP | 3 597 233 A1 | 1/2020 |
| EP | 3597237 A1 | 1/2020 |
| JP | 6579489 B2 | 9/2019 |
| WO | 99/16485 A1 | 4/1999 |
| WO | 99/16487 A1 | 4/1999 |
| WO | 2011/131782 A2 | 10/2011 |
| WO | 2011138316 A1 | 11/2011 |
| WO | 2020/152192 A1 | 7/2020 |
| WO | 2021/069284 A1 | 4/2021 |
| WO | 2021122671 A1 | 6/2021 |
| WO | 2021126671 A1 | 6/2021 |

OTHER PUBLICATIONS

International Search Report and Written Opinion dated Aug. 10, 2022 in corresponding International Application No. PCT/EP2022/059317.
International Search Report and Written Opinion dated Aug. 3, 2022 in corresponding International Application No. PCT/EP2022/059344.
International Search Report and Written Opinion dated Feb. 11, 2021 in corresponding International Patent Application No. PCT/EP2020/077459 filed Oct. 1, 2020.
Extended European Search Report dated Sep. 24, 2021 in corresponding European Patent Application No. 21167293.6.
Extended European Search Report dated Dec. 8, 2021 in corresponding European Patent Application No. 21181883.6.
European Search Report issued in corresponding European Application No. 21202384.0 dated Apr. 8, 2022.
International Search Report and Written Opinion dated Jul. 25, 2022 in corresponding International Application PCT/EP2022/059334.
Extended European Search Report dated Jan. 4, 2022 in corresponding European Patent Application No. 21184545.8.
Extended European Search Report dated Dec. 13, 2021 in corresponding European Patent Application No. 21181887.7.

* cited by examiner

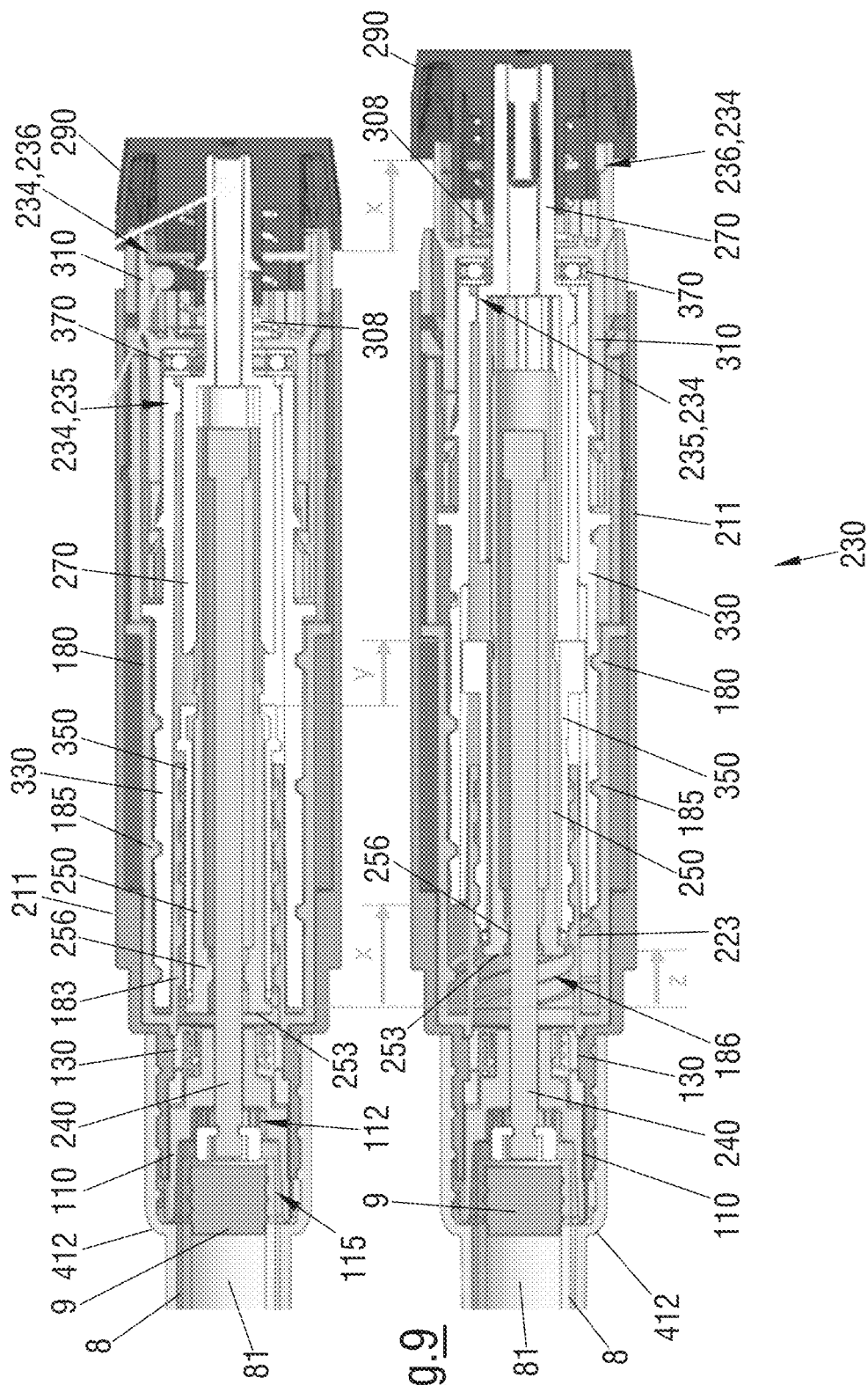

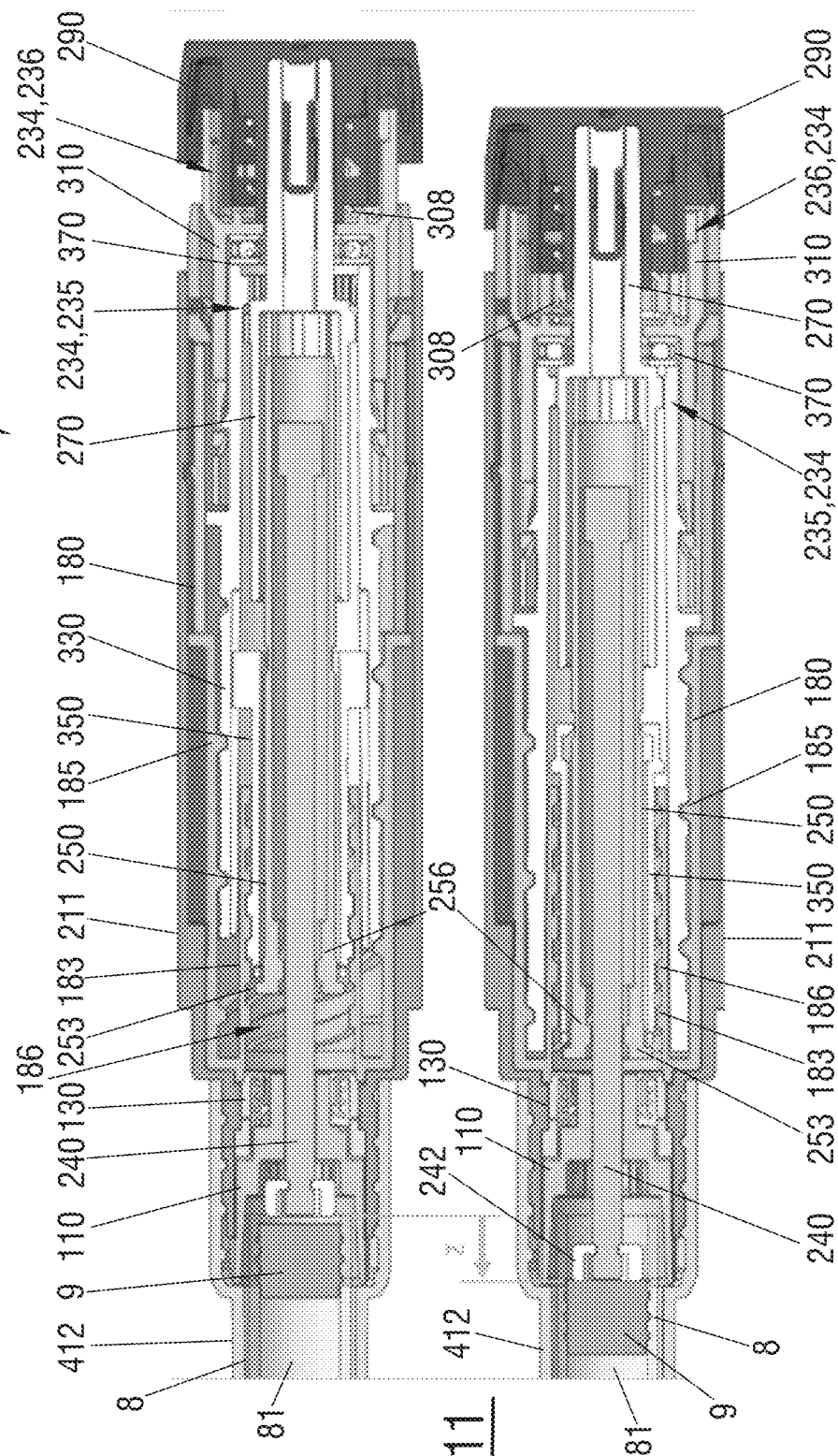

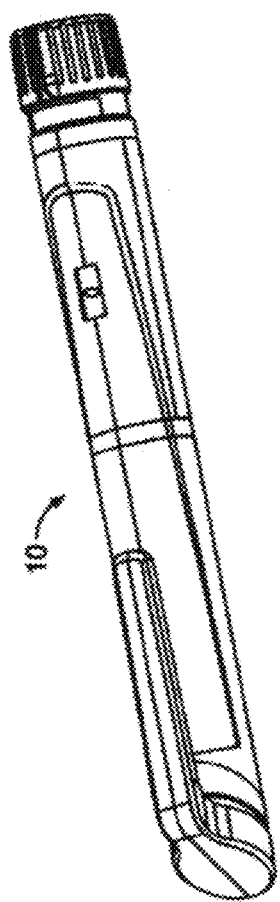
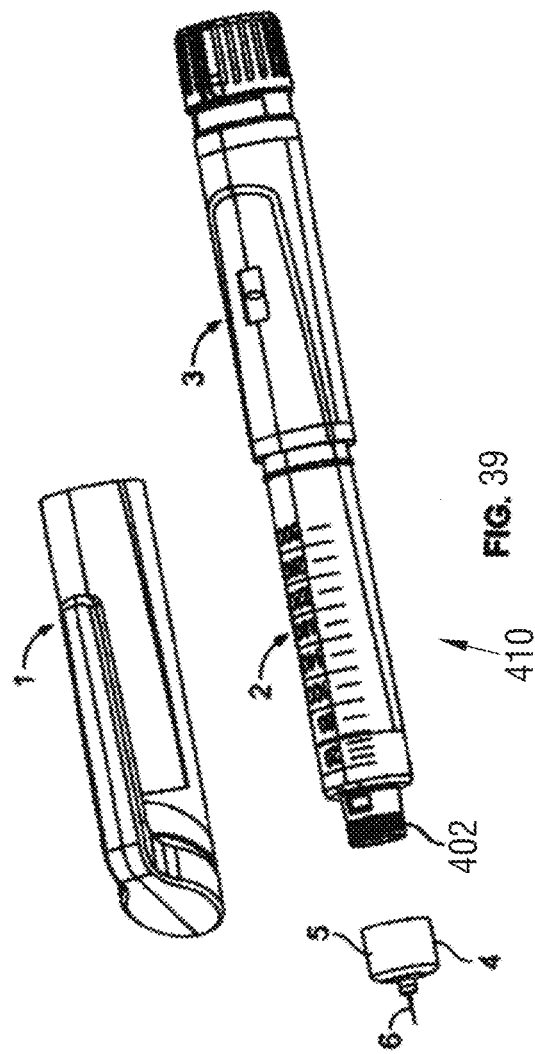
FIG. 38
FIG. 39

DRUG DELIVERY DEVICE

CROSS-REFERENCE TO RELATED APPLICATION

This application claims priority to European Patent Application No. 21167293.6 filed on Apr. 7, 2021, European Patent Application No. 21181883.6 filed on Jun. 25, 2021, European Patent Application No. 21181887.7 filed on Jun. 25, 2021, and European Patent Application No. 21184545.8 filed on Jul. 8, 2021, the contents of each of which are hereby incorporated herein by reference in their entirety.

BACKGROUND

Field of the Invention

The invention relates to drug delivery devices having friction reduction mechanisms.

Background Information

To date, conventional drug delivery devices which can be used by medically non-trained people, such as for example patients, to self-administer medicaments are becoming more and more sophisticated in view of their dose setting mechanisms and/or their dose delivery mechanisms. Uses of such devices can include, for example, diabetics, where medication management, i.e. the degree to which a patient follows medical instructions and protocols which can originate from a medically trained person such as a doctor, is often of extreme importance. Of the known conventional drug delivery devices, which can be actuated manually, semi-automatically or automatically to eject a drug out of a drug compartment, the pen-type device is generally very popular such that it is now available both in reusable and disposable designs.

Conventional disposable drug delivery devices can be completely discarded once the drug compartment of the device has been emptied to a degree that no further dose of medicament can be ejected from the device. With single use devices, the device is discarded after a single dose has been ejected, while multi-use devices enable the repeated ejection of several doses from the same medicament container or drug compartment.

With reusable devices, the drug delivery device includes the possibility to reset the delivery device such that the medicament container can be replaced with a new one when the last dose has been delivered from the container. The emptying of the container can happen after one dose ejection or after several dose ejections.

SUMMARY

Conventional devices of the art which are configured such that the patient can self-adjust the amount and/or the size of the doses usually comprise rather complex dose setting and delivery mechanisms which include several different components that rotate with respect to each other. These devices are reliable when it comes to dose setting and dose delivery but they also have shown that they are rather susceptible to wear such that they need to be replaced quite often.

Therefore, it is an object of embodiments of the invention to provide drug delivery devices which are more robust against wear and tear when used multiple times. This object is solved by the subject matter disclosed herein.

In one embodiment of the present disclosure, a drug delivery device with a housing is provided, with the housing being configured to connect to a dispensing unit comprising a compartment containing a fluid, a piston rod configured to move in a proximal direction, for example out of the housing, for ejecting the fluid, and a dosing mechanism, wherein the dosing mechanism comprises an actuation member to be actuated by a user for advancing the piston rod and to thereby eject a set dose out of the compartment. The device further comprises a conversion mechanism, which is configured to convert a movement of the actuation member to a movement of the piston rod. The conversion mechanism comprises a dose selector member, such as a dose selector sleeve, which is rotationally fixed to the housing and axially movable with respect to the housing, and a dosing member, such as a dose setting sleeve, which is rotationally movable with respect to the dose selector member. The dose selector member is disposed between the actuation member and the dosing member. The drug delivery device further comprises a friction reduction mechanism, which is disposed between the dose selector member and the dosing member to reduce friction between the dose selector member and the dosing member upon relative rotational movement with respect to each other.

In this connection it is noted that throughout the application text, the expressions "proximal" and "distal" refer to parts of the delivery device, which are closer or further away from the body of a patient, respectively, and which are therefore closer to or further away from a delivery or injection site, respectively. Hence, a proximal end of the drug delivery device is the part where the dispensing unit is located, and thus optionally closest to a needle that can be attached to the dispensing unit, whereas a distal end of the drug delivery device is the part which is located at the opposite end of the drug delivery device that can be configured to be held by the patient during drug delivery.

As can be seen from the above, a drug delivery device is provided with which a user is able to set a dose of drug which he or she would like to have injected, and to self-administer said drug by operating the actuation member. For this purpose, the conversion mechanism can be configured to transfer a movement of the actuation member to a movement of the piston rod such that first a defined dose can be set which can then be ejected out of the connected cartridge.

The dispensing unit can be releasably or permanently connected to the housing. When being permanently connected, the dispensing unit may, for example, be integrated into the housing. It also can be connected to the housing by a non-releasable connection that is configured not to disengage during intended use of the device. For example, the non-releasable connection between the housing and the dispensing unit can be configured to withstand all forces that occur during the intended use of the device. When being configured to be releasably connected to the housing, the dispensing unit can comprise connection means, such as threaded connection means, for attachment to the housing of the drug delivery device.

The dispensing unit can comprise a cartridge and the compartment containing the drug can be part of and/or or surrounded by the cartridge. The cartridge can be held within a cartridge container. With other embodiments, the dispensing unit can be configured as a single piece component that surrounds the compartment containing the drug.

In this connection it is further noted that the conversion mechanism can comprise several components or members such as the dosing member and the dose selector member which are configured to transfer a movement of the actuating member to a movement of the piston rod. This can be done, for example, by translating a rotation and/or an axial movement of the actuation member to an axial movement of the piston rod such that the piston rod can eject the drug out of the cartridge. The conversion mechanism can, for example, provide a mechanical advantage that translates a force, which is exerted by a user of the device on the actuation member, into a larger or smaller force, with which the piston rod is advanced in the proximal direction.

For the above purposes, the dose selector member, which is rotationally fixed to the housing and axially movable with respect to the housing is provided together with the dosing member, which is rotationally movable with respect to the dose selector member. Furthermore, the dose selector member is disposed between the actuation member and the dosing member. Hence, these components, i.e. the dose selector member and dosing member can transfer a rotational and/or axial movement of the actuation member to the piston rod.

The dose selector member and the dosing member can be configured to be pressed against each other and to simultaneously rotate with respect to one another during dose delivery and/or during dose setting. The friction reduction mechanism that is disposed between the two components then reduces the friction, which can arise when one of the two components rotates with respect to the other one while simultaneously transferring an axial force from one of the components, such as the dose selector member, to the other one, such as the dosing member.

the friction reduction mechanism can be designed as a mechanism which is provided in addition to the different components of the conversion mechanism.

According to an embodiment of the invention, the friction reduction mechanism comprises a bearing element, for example a ball bearing. Thus, the friction reduction mechanism can not only be provided by the elements of the dosing mechanism themselves but rather by an additional element, such as the bearing element.

In this connection it is noted that the bearing element can be configured as an individual component separate from the dose selector member and/or the dosing member. This has the advantage that, for example, when the bearing element begins to fail because of wear it can be replaced with a new one without having to replace the whole drug delivery device. Furthermore, a separate element efficiently reduces friction between the dose selector member and the dosing member. For example, the bearing element can have a different material than the dose selector member and/or the dosing member. The material of the bearing element can provide a coefficient of friction that is smaller than that of the material of the dose selector member and/or the dosing member.

According to an embodiment the bearing element is configured to rotate with respect to the dose selector member and/or the dosing member. Since the dosing member is rotationally movable with respect to the dose selector member, a bearing element that is configured to rotate with respect to one or both of the dose selector member and the dosing member can further help to reduce the friction that arises because of the rotational movement of said two members with respect to one another.

According to a further embodiment, the bearing element is axially restrained between the dose selector member and the dosing member. That is, the bearing element cannot be allowed to move axially between the dose selector member and the dosing member in order to ensure that a friction reducing effect can always be provided. Alternatively, the axially restrained bearing element can only be allowed to axially move at most a limited distance between the dose selector member and the dosing member, which distance is defined by the distance between the dose selector member and the dosing member. The distance between the dose selector member and the dosing member can also be limited, for example by a connector that connects the dose selector member to the dosing member.

According to an embodiment, the dose selector member is axially restrained, such as axially fixed, with respect to the dosing member, and the friction reduction mechanism is sandwiched between the dosing member and the dose selector member. In this context the expression "sandwiched" can mean that the friction reduction mechanism is disposed between the dosing member and the selector sleeve in such a way that said two sleeves hold the friction reduction mechanism in place. This can be done by axially restraining, such as fixing, the dose selector member with respect to the dosing member such that an axial movement between the two is not possible or limited.

In another embodiment of the invention, the dose selector member is connected to the dosing member by a connector, such as a snap-on connector, that restricts relative movement between the dose selector member and the dosing member in the axial direction and allows for relative rotational movement between the dose selector member and the dosing member. Such a connector can, for example, be provided by a hook connection or anything alike. Especially, a movement of the dosing member in a proximal direction, i.e. in a direction towards the dispensing unit, with respect to the dose selector member can be prevented with such a connection.

According to an embodiment, the friction reduction mechanism is provided at a distal end of the dosing member. This way, an axial movement of the dosing member can also be prevented in a distal direction, i.e. in a direction away from the dispensing unit and towards the dose selector member. This is because the friction reduction mechanism can be provided at said distal end. Hence, at said distal end the dosing member can touch the friction reduction mechanism that can further lean against the dose selector member to prevent an axial movement of the dosing member in said direction.

It can be possible that the dose selector member comprises a contact surface which is in contact with the friction reduction mechanism. Hence, the contact surface can be in direct contact with the friction reduction mechanism. This way the friction reduction mechanism can not only reduce the friction at said contact surface but also limit an axial movement of the dose selector member in the proximal direction.

According to an embodiment the contact surface can comprise a ring shape and/or can be provided at an inner surface of the dose selector member. The contact surface can thus either be provided at an outer or an inner surface of the dose selector member. In an additional embodiment it can further be possible to provide the contact surface at a proximal end of the dose selector member.

The contact surface can surround the whole circumference of the dose selector member. The contact surface can also be provided inside the dose selector member, such as a ring-shaped inside surface, that only surrounds a part of the cross-sectional area of the dose selector member.

It can further be possible that the dosing member is partially located inside the dose selector member. In this case the friction reduction mechanism can also be disposed inside the dose selector member such that it is in contact with the contact surface of the dose selector member.

According to an embodiment, the contact surface can be provided at a proximal end of the dose selector member such that the friction reduction mechanism completely separates the dose selector member from the dosing member.

In another embodiment it could generally also be possible that the contact surface, such as the ring-shaped contact surface, is provided at an outer surface of the dose selector member such that the dose selector member can partially be provided inside the dosing member with the friction reduction mechanism being disposed between the contact surface and the dose selector member.

It can further be possible that the dosing member is coupled to the housing via a threaded connection that translates rotation of the dosing member into an axial movement of the dosing member with respect to the housing. That is, during the processes of dose setting and/or dose delivery the dosing member can be configured to move in an axial distal or proximal direction with respect to the housing of the drug delivery device while simultaneously rotating with respect to the housing.

For example, during dose setting, the dosing member can be rotated by rotating the actuation member, which can then lead to an axial movement of the dosing member due to the threaded connection to the housing.

As another example, during dose delivery, the actuation member can press on the dose selector member and dose selector member can in turn press on the dosing member. The threaded connection of the dosing member to the housing can then convert the induced axial movement of the dosing member into a rotation of the dosing member with respect to the housing.

The axial motion can in some embodiments be limited by one or more stopping features which can be provided to limit the axial movement of the dosing member in the distal and/or proximal direction.

In a further embodiment the actuation member can further be axially movable with respect to the dose selector member and configured to move towards the dose selector member when being actuated by a user. For example, the actuation member can be configured to be actuated by the user such that it moves towards the dose selector member, i.e. in a proximal direction, upon transferring the drug delivery device from a dose setting state into a dose delivery state. A dosing mechanism of the drug delivery device can be configured to allow for a setting of the dose to be injected when the dose delivery device is in the dose setting state, while it can be configured to allow for a delivery of the set dose when the dose delivery device is in the dose delivery state.

According to an embodiment, the actuation member is rotationally movable with respect to the dose selector member, for example for setting the dose to be injected. Such an additional rotational movability can either be provided in addition to the axial movability or in some cases also instead of it.

The actuation member can be, for example, be axially movable with respect to the dose selector member to transfer a dosing mechanism of the dose delivery device from a dose setting state into a dose delivery state. In the dose delivery state, further axial movement of the actuation member with respect to the housing can force the dose selector member to follow this axial movement, so that the actuation member and the dose selector member move in unison with respect to the housing. Axial movement of the actuation member for transferring the drug delivery device into the dose delivery state and subsequent unison axial movement of the actuation member and the dose selector member can both be directed in the proximal direction. During dose delivery, the actuation member and/or the dose selector member and/or the dosing member can retain their relative axial positions with respect to each other.

Furthermore, the actuation member can be rotationally movable with respect to the housing and the dose selector member during dose setting, whereby rotation of the actuation member changes the set dose. During dose delivery, the actuation member can be rotationally locked with respect to the dose selector member and the housing.

During dose setting, changing the set dose can cause an axial movement of the dosing member and/or the dose selector member and/or the actuation member with respect to the housing. Thereby, the dosing member and/or the dose selector member and/or the actuation member can retain their relative axial positions with respect to each other.

According to an embodiment, the conversion mechanism further comprises a nut, and a driver, wherein the nut is threadedly engaged with the piston rod and rotationally fixed to the housing during delivery of the set dose, and wherein the driver is rotatable and axially movable with respect to the housing during dose delivery and configured to axially advance the nut during dose delivery.

As mentioned above, the driver is rotatable and axially movable with respect to the housing during dose delivery, i.e. during ejection of the fluid out of the delivery device. Furthermore, the driver is configured to axially advance the nut during said dose delivery. This can for example be realized by a threaded connection between the driver and the housing such that a rotation of the driver can be translated into an axial movement of the driver which can then be transferred to the nut.

The driver can be configured to axially advance the nut during dose delivery by transferring an axial force to the nut, either directly, that is by directly abutting against the nut, or indirectly, that is by transferring the axial force to the nut via one or more intermediate members.

The piston rod can be rotationally fixed with respect to the housing at least during dose delivery. In this case, the nut and the piston rod are rotationally fixed with respect to each other during dose delivery so that the threaded connection axially locks the nut with the piston rod during dose delivery. Therefore, the nut and the piston rod are configured to simultaneously move axially during dose delivery as if they were a single member.

During dose setting, the nut can be configured to rotate with respect to the piston rod. For example, the piston rod can be rotationally locked to the housing also during dose setting and the nut can be configured to rotated with respect to the housing during dose setting. Rotation of the nut then axially advances the nut with respect to the piston rod during dose setting due to the threaded connection between nut and piston rod. Axial advancement of the nut with respect to the piston rod and/or with respect to the housing can define the axial advancement of the piston rod with respect to the housing during dose delivery.

According to an embodiment, the conversion mechanism comprises a further friction reduction mechanism, wherein the further friction reduction mechanism is provided between the nut and the driver to reduce friction therebetween during dose delivery. This can be helpful if the driver rotates with respect to the nut during dose setting and/or dose delivery such that a friction between these two components, which is caused by said rotation, can be reduced.

In this connection it is noted that the further friction reduction mechanism can be a bearing, for example a disc bearing. Such bearings are known and can thus easily be disposed between the nut and the driver without the need of further mechanism components.

In some embodiments the driver can be connected to the nut via a connection which limits axial movement between the driver and the nut. Such a connection or connector can not only limit but in some cases even prevent an independent axial movement between the driver and the nut. It can nevertheless be possible that said connection still allows a rotational movement between these two components.

The connection can be provided at a distal end of the driver. In some cases, such an arrangement can lead to the nut being arranged at the distal end of the driver whereas in other cases this can also mean that the nut is at least partially provided inside the driver such that the connection can connect with a middle section of the nut.

In this connection it can further be possible that the connection can be configured as a snap connector. Such connectors are especially advantageous when an axial movement between two components is supposed to be suppressed and at the same time rotational movement between the components is supposed to be allowed.

In some embodiments the driver is rotationally fixed with respect to the dosing member. Such a rotational fixing of the driver with respect to the dosing member may, for example, be realized by linear guides or anything similar that still allow an axial movement between the driver and the dosing member.

In some embodiments, the driver is coupled to the housing via a threaded connection that translates rotational movement of the driver into axial movement. As already mentioned above, the axial movement can then be transferred to the nut. The threaded connection between the driver and the housing can have a pitch that is different, for example slightly different, from the pitch of the threaded connection between the nut and the piston rod such that a path travelled by the driver during dose setting is different from the path travelled by the nut. In some embodiments, the driver can travel a longer distance than the nut. This can prevent locking between the nut and the driver during dose setting in cases in which the nut and the driver are moved independently along the longitudinal axis and it has to be assured that the two members do not approach each other during rotation.

The invention further relates to another drug delivery device with a housing, which is configured to connect to a dispensing unit comprising a compartment containing a fluid, a piston rod configured to move in a proximal direction out of the housing for ejecting the fluid, and a dosing mechanism, wherein the dosing mechanism comprises an actuation member to be actuated by a user for advancing the piston rod and to thereby eject a set dose out of the compartment. Furthermore, the dosing mechanism comprises a conversion mechanism, which is configured to convert movement of the actuation member to movement of the piston rod. The conversion mechanism comprises a nut and a driver, wherein the nut is threadedly engaged with the piston rod and rotationally fixed to the housing during delivery of the set dose. The driver is rotatable and axially movable with respect to the housing during dose delivery and configured to axially advance the nut during dose delivery. Furthermore, the conversion mechanism comprises a friction reduction mechanism, wherein the friction reduction mechanism is disposed between the nut and the driver to reduce friction therebetween during dose delivery.

As can be seen from the above, a drug delivery device is provided with which a user is able to set a dose of drug which he or she would like to have injected, and to self-administer said drug by operating the actuation member. For this purpose, the conversion mechanism is configured to transfer a movement of the actuation member to a movement of the piston rod such that a set dose can be ejected out of the compartment.

The compartment can be a part of the dispensing unit which can be connected or which is permanently connected to the housing of the drug delivery device, for instance at a proximal end of the drug delivery device.

In this connection it is further noted that the conversion mechanism can comprise several components such as the nut and the driver which are configured to transfer movement of the actuating member to movement of the piston rod. This can be done, for example, by translating a rotation and/or an axial movement of the actuation member to an axial movement of the piston rod such that the piston rod can eject the drug out of the cartridge.

For the above purpose, the driver is rotatable and axially movable with respect to the housing during injection of the drug. i.e. when the drug is ejected out of the cartridge, and configured to axially advance the nut during said injection. The nut is further configured to advance the piston rod since said two components are threadedly engaged with one another such that a movement of the nut can lead to an axial movement of the piston rod.

Since the driver rotates with respect to the housing during dose delivery and the nut does not and since the driver axially advances, for example pushes, the nut during dose delivery, relative rotation of the nut and the driver under simultaneous axial load can lead to considerable friction during dose delivery. Providing the friction reduction mechanism between the two components can then reduce this friction and allow for easier dose delivery.

The friction reduction mechanism can be designed as a mechanism which is provided in addition to the different components of the conversion mechanism.

The friction reduction mechanism can further comprise a bearing element, for example a disc bearing. Thus, the friction reduction mechanism can not only be provided by the elements of the dosing mechanism themselves but rather by an additional bearing element.

According to an embodiment the bearing element is configured as a component separate from the nut and/or the driver. This has the advantage that, for example, when the bearing element starts to fail because of wear it can be replaced with a new one without having to replace the whole drug delivery device.

According to a further embodiment the bearing element is configured to rotate with respect to the nut and/or the driver. Since the nut and the driver rotate with respect to each other during dose delivery, the bearing element that is configured to rotate with respect to one or both of the nut and the driver can further help to reduce the friction that arises because of the rotational movement of said two components to one another.

According to another embodiment the bearing element is axially restrained between the nut and the driver. That is, the bearing element can not be allowed to move axially between the nut and the driver in order to ensure that friction reducing effect can always be provided. Alternatively, the axially restrained bearing element can only be allowed to travel at most a limited distance between the nut and the driver, for example a distance that is smaller than the axial extent of the bearing element.

The nut can further be connected to the driver by a connection, such as a snap-on connection, that restricts relative movement between the nut and the driver in the axial direction, for example during actuation of the device. Such a connection can, for example, be provided by a hook connection or anything alike. Especially, movement of the nut in a proximal direction, i.e. in a direction towards the dispensing unit, with respect to the driver can be prevented with such a connection.

In some embodiments the friction reduction mechanism can be provided at a proximal end of the driver. In this embodiment the nut can be at least partially provided inside the driver such that the friction reduction mechanism can be provided at the proximal end of the driver while still acting between the nut and the driver.

In this connection it is further noted that it is possible that a proximal front surface of the driver rests against the friction reduction mechanism. Hence, in order for the friction reduction mechanism to be able to act between the driver and the nut, the nut needs to extend partially from the proximal end of the driver.

In some embodiments, the nut can even extend at least partially from the proximal end of the driver.

It can further be possible that the friction reduction mechanism is provided at a proximal end of the nut. Hence, for the case where the nut extends beyond the proximal end of the driver the friction reduction mechanism can also be provided at the proximal end of the nut such that the proximal end of the nut as well as the driver are operatively coupled to one another via the friction reduction mechanism.

In some embodiments the friction reduction mechanism rests against a proximal protrusion of the nut. Such a protrusion can, for example, be realized by providing a ring-shaped contact surface which extends along the circumference of the proximal end of the nut. Hence, the friction reduction mechanism, such as for example the bearing element, can be sandwiched, i.e. pinched, between the proximal protrusion of the nut and the proximal end of the driver.

It can further be possible that the driver is connected to the nut via a connection, such as a connector, which limits axial movement between the driver and the nut. Such a connection can not only limit but in some cases even prevent an independent axial movement between the driver and the nut. It can nevertheless be possible that the connection still allows a rotational movement between these two components.

The connection can be provided at a distal end of the driver. In some embodiments, such an arrangement can lead to the nut being arranged at the distal end of the driver whereas in other embodiments this can also mean that the nut is at least partially disposed inside the driver such that the connector can connect with a middle section of the nut.

It can further be possible that the connection is configured as a snap fit connector. Such connectors are especially advantageous when an axial movement between two components is supposed to be suppressed and at the same time a rotational movement between the components is supposed to be allowed.

In some embodiments the driver is rotationally fixed with respect to the dosing member. Such a rotational fixing of the driver with respect to the dosing member may, for example, be realized by linear guides or anything similar that still allows an axial movement between the driver and the dosing member.

The driver can be coupled to the housing via a threaded connection that translates rotational movement of the driver into axial movement. As already mentioned above, said axial movement can then be transferred to the nut. Said threaded connection between the driver and the housing can have a pitch that is different than the pitch of the threaded connection between the nut and the piston rod such that a travelled path of the driver is different from the travelled path of the nut. In some cases the driver can travel a longer distance than the piston rod.

With all drug delivery devices according to embodiments of the present disclosure, the conversion mechanism for transferring axial movement of the actuation member to axial movement of the piston rod can comprise the dose selector member, the dosing member, the driver, the nut and/or the inner housing. It furthermore can comprise the friction reduction mechanism, such as the ball bearing, between the dose selector member and the dosing member and/or the friction reduction mechanism, such as the disc bearing, between the driver and the nut.

With all drug delivery devices and dispensing units according to the present disclosure, a medication stored in the compartment can be selected from the group of members consisting of diabetes medication, such as insulin, growth hormones, fertility hormones, osteoporosis medication, blood thinners, such as heparin, and drugs against migraine, HIV associated lipodystrophy, non-alcoholic fatty liver diseases or obesity.

BRIEF DESCRIPTION OF THE DRAWINGS

The invention will be explained in more detail hereinafter with reference to the drawings.

FIG. 8 is a longitudinal cross sectional view of the dosing mechanism of the drug delivery device through the first cross sectional plane prior to setting a dose;

FIG. 9 is a longitudinal cross sectional view of the dosing mechanism through the first cross sectional plane after setting a dose, the dosing mechanism still being in a dose setting state;

FIG. 10 is a longitudinal cross sectional view of the dosing mechanism through the first cross sectional plane after setting the dose, the dosing mechanism being in a dose delivery state;

FIG. 11 is a longitudinal cross sectional view of the dosing mechanism through the first cross sectional plane after delivering the dose, the dosing mechanism being in the dose setting state;

FIG. 38 is a perspective view of a further drug delivery device;

FIG. 39 is the further drug delivery device with a removed cap;

DETAILED DESCRIPTION

In the embodiments of the present application, the term "distal part/end" refers to the part/end of the device, or the parts/ends of the components or members thereof, which in accordance with the use of the device, is located the furthest away from a delivery/injection site of a patient. Correspondingly, the term "proximal part/end" refers to the part/end of the device, or the parts/ends of the members thereof, which in accordance with the use of the device is located closest to the delivery/injection site of the patient.

The embodiments of the present disclosure of dose stops are applicable with a number of medicament delivery devices, for example, injection devices. One possible injection device is the pen-type design illustrated in FIG. 1.

Figure 1:
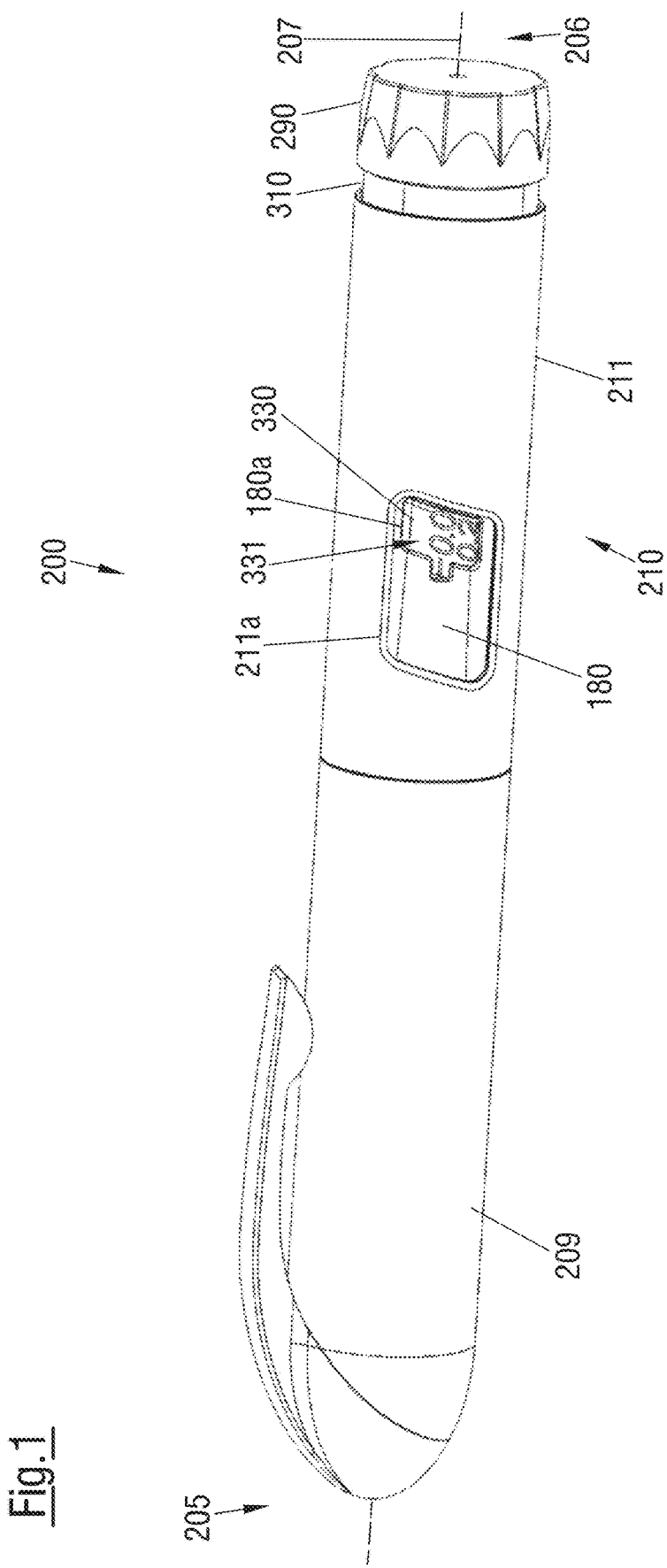
FIG. 1 is a perspective view of a drug delivery device according to an embodiment of the present invention with an attached cap.

FIG. 1 shows a drug delivery device 200 that comprises a connection device or means for attaching a dispensing unit. The drug delivery device has a generally tubular housing 210, which is elongated along a longitudinal axis 207. A generally tubular cap 209 is attached to a proximal end 205 of the housing 210. At a distal end 206 of the housing 210, which distal end 206 is located opposite to the proximal end 205 along the longitudinal axis 207, the drug delivery device 200 comprises a dose setting member 290.

The dose setting member 290 is rotatable around the longitudinal axis 207 and is configured to be gripped and rotated by a user of the device 200 to set a dose to be delivered by the device 200. In this way the dose setting member 290 can also be considered a knob or the like. In the embodiment shown in FIG. 1, the dose setting member 290 is configured as a knob that terminates the drug delivery device 200 at its distal end 206. With other embodiments, the dose setting member 290 can also be, for example, configured as a rotatable sleeve or ring that surrounds the longitudinal axis 207.

The dose setting member 290 is connected to the housing 210 via a dose selector member 310 that is rotationally locked and axially movable relative to the housing 210 both during dose setting and during dose delivery. When increasing a set dose by turning the dose setting member 290 relative to the housing 210 and the dose selector member 310, the dose selector member 310 moves distally out of the housing 210, thereby also moving the dose setting member 290 in the distal direction.

The housing 210 comprises an outer housing 211, which, in the present embodiment, is made from metal, and an inner housing 180. The inner housing 180 is located within the outer housing 211. In the present embodiment, it is made from a plastic material. The outer housing 211 comprises a window 211a through which a part of the inner housing 180 and a window 180a within the inner housing 180 is visible to a user of the device 200. Through the windows 211a and 180a, a dose indication member 330, which is located inside the generally tubular inner housing 180, is visible to the user.

The dose indication member 330 is also configured as a generally tubular member and carries on its outer cylindrical surface a dose scale comprising several optical markers 331 that correspond to the respective set dose. When setting a dose, the dose indication member 330 rotates within the inner housing 180, which changes the location of the scale and thus also the optical markers 331 visible through the windows 211a and 180a.

Figure 2:
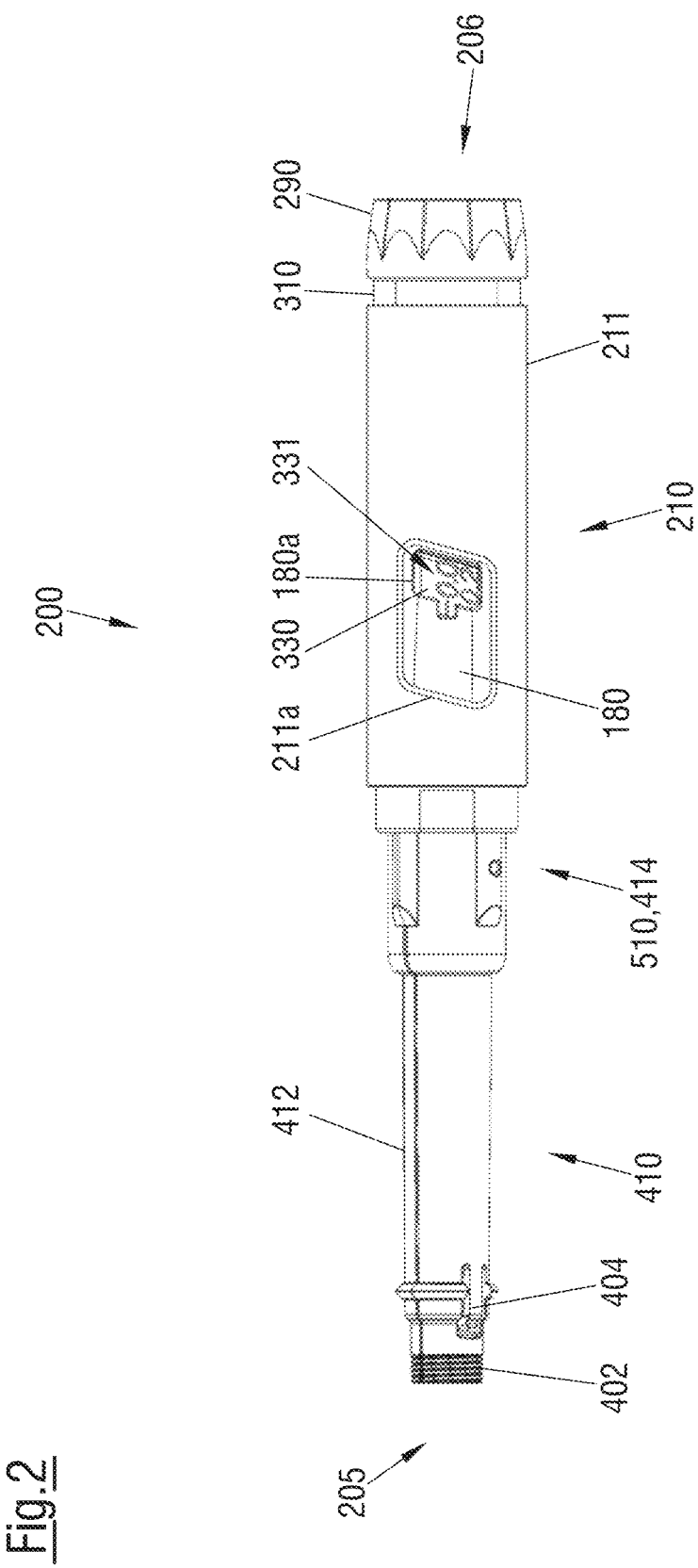
FIG. 2 is a perspective view of the drug delivery device with the cap removed and an attached dispensing unit.
Figure 3:
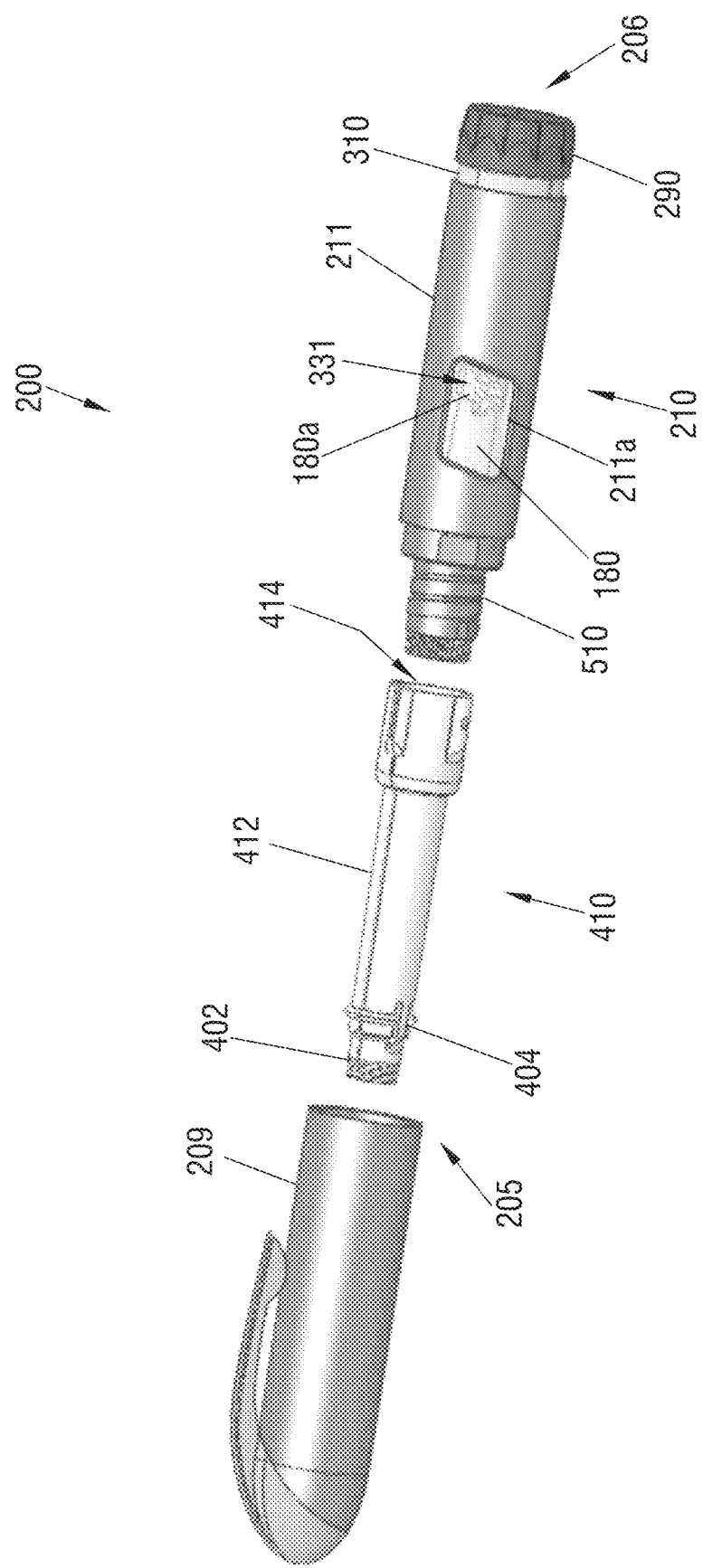
FIG. 3 is a perspective view of the drug delivery device, the cap and the dispensing unit.

FIG. 2 shows the drug delivery device 200 with the cap 209 removed. A dispensing unit 410 that comprises the drug to be delivered by the device 200 is removably attached to the proximal end 205 of the housing 210. FIG. 3 shows the cap 209 and the dispensing unit 410 removed from the drug delivery device 200. With the cap 209 and the dispensing unit 410 attached to the housing 210 of the device 200, the dispensing unit 410 is fully received within the cap 209.

The dispensing unit 410 comprises a cartridge holder 412, which, in the current embodiment, is made from a plastic material. The cartridge holder 412 attaches to the outer housing 211 of the drug delivery device 200 via a connection, which comprises first connection device or means 510 located at the proximal end of the housing 210 and corresponding first connection device 414 located at the distal end of the dispensing unit 410. The first connection device 510 of the housing 210 are formed as integral part of the outer housing 211 and the first connection device 414 of the dispensing unit 410 are formed as integral part of the cartridge holder 412.

At its proximal end, the cartridge holder 412 of the dispensing unit 410 comprises a needle connector 402 that is configured to receive a hollow needle or cannula through which the drug is delivered by the drug delivery device 200. In the present embodiment, the needle connector 402 is configured as a threaded connector. With other embodiments, the needle connector 402 can also be configured as, for example, a snap-fit, bayonet or Luer-Lok connection.

Figure 4:
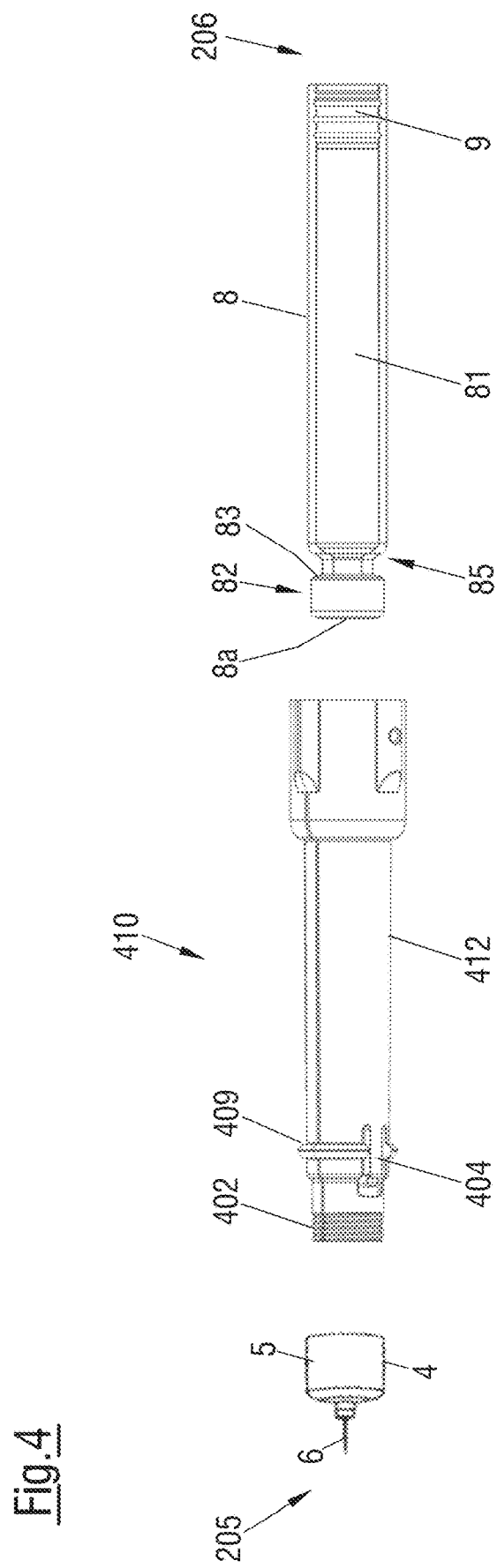
FIG. 4 is a side view of the dispensing unit comprising a cartridge holder and a cartridge and a needle attachable to the dispensing unit.

FIG. 4 shows the cartridge holder 412 of the dispensing unit 410 and a cartridge 8 that can be inserted into the cartridge holder 412, as well as a needle 4 attachable to the needle connector 402.

The cartridge 8 has a generally cylindrical body, which, in the present embodiment, is made from glass, and which surrounds a drug compartment 81 that contains a liquid drug to be delivered by the drug delivery device 200. The drug compartment 81 is sealed at its distal end by an elastic plunger 9, which is movable along the longitudinal axis within the body of the cartridge 8. At its proximal end, the cartridge 8 comprises an annular rim 82, which is separated from the body by an annular detent 85 located distally from the annular rim 82. At a proximal front surface of the cartridge 8, which is orientated perpendicular to the longitudinal axis 207, the cartridge 8 comprises a sealing element or means or septum 8a, which seals the drug compartment 81 in the proximal direction.

When being fully inserted into the cartridge holder 412, the sealing element 8a is located at the proximal end of the cartridge holder 412 and accessible through an opening of the cartridge holder 412. The cartridge 8 is non-releasably held in its inserted position by a snap hook 404. The snap hook 404 is configured as a flexible member. In the present embodiment, the snap hook 404 is formed by a cut-out portion of the cartridge holder 412. Upon insertion of the cartridge 8 into the cartridge holder 412, the snap hook 404 snaps over the annular rim 82 of the cartridge 8. A radially inwardly protruding finger of the snap hook 404 is then located within the annular detent 85 of the cartridge 8 and prevents distal movement of the cartridge 8 by abutting against a distal surface 83 of the annular rim 82.

This non-releasable connection between the cartridge 8 and the cartridge holder 412 prevents the removal of the cartridge 8 from the cartridge holder 412 during the intended use of the dispensing unit 410. For example, it prevents removal of the cartridge container 8 unless the snap hook 404 is intentionally and/or forcefully brought out of engagement with the annular rim 82. The non-releasable connection is thereby configured in a way that such disengagement is only possible using tools or excessive forces that are higher than the forces acting on the non-releasable connection during normal and/or intended use of the dispensing unit 410, for example during mounting of the dispensing unit 410 to the housing 210, during attachment of the needle 4 to the cartridge container 412 or during handling of the dispensing unit 410 with the cartridge 8 inserted into the cartridge holder 412. This handling can also comprise shock forces that can occur during transport and/or unintentional dropping of the dispensing unit and that do not exert forces that would destroy the dispensing unit 410 and/or the cartridge holder 412 and/or the cartridge 8. The non-releasable connection between the cartridge 8 and the cartridge holder 412 allows to provide and sell the dispensing unit 410 with an inserted cartridge 8 as a single, pre-mounted unit.

The needle 4 is configured as a pen needle. It comprises a hub 5 that carries a double-ended cannula 6. The cannula 6 is longitudinally received within the hub 5. The hub 5 comprises at its distal end a hub connector that matches the needle connector 402 of the cartridge holder 412. In the present embodiment, the hub connector is configured as an inner thread matching the outer thread of the needle connector 402. The cannula 6 protrudes from the proximal end of the hub 5. It has sharp ends at both its proximal and distal ends. With its distal end, the cannula 6 penetrates the sealing element 8a of the cartridge 8 and thus establishes a fluid connection between the drug compartment 81 and the proximal end of the cannula 6. The proximal end of the cannula 6 is configured to be inserted into a delivery site, such as a skin of the user of the device 200, thereby permitting injection of the drug into the delivery site.

Figure 5:
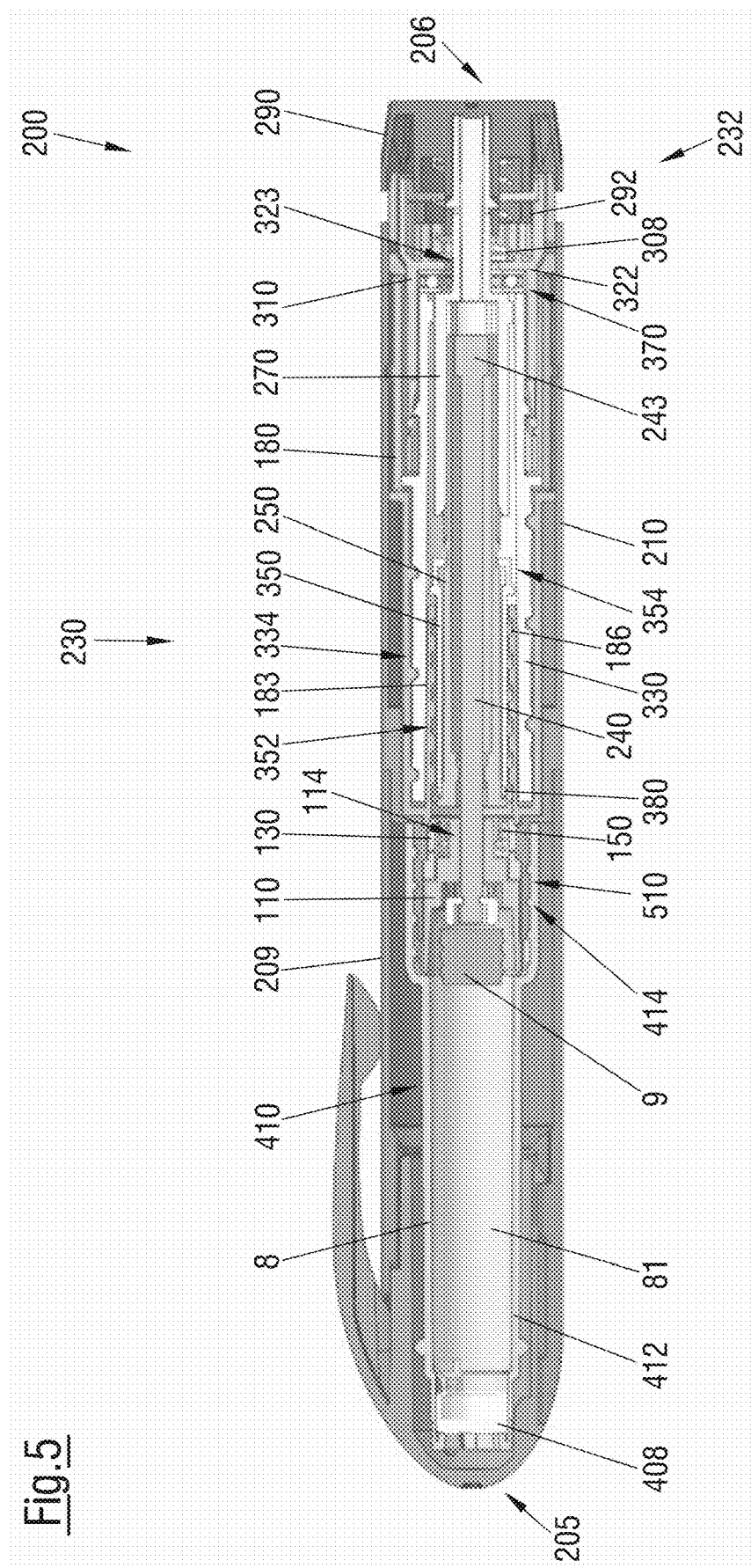
FIG. 5 is a longitudinal cross sectional view of the drug delivery device, the dispensing unit and the cap through a first cross sectional plane with the drug delivery device being in a dose setting state.
Figure 6:
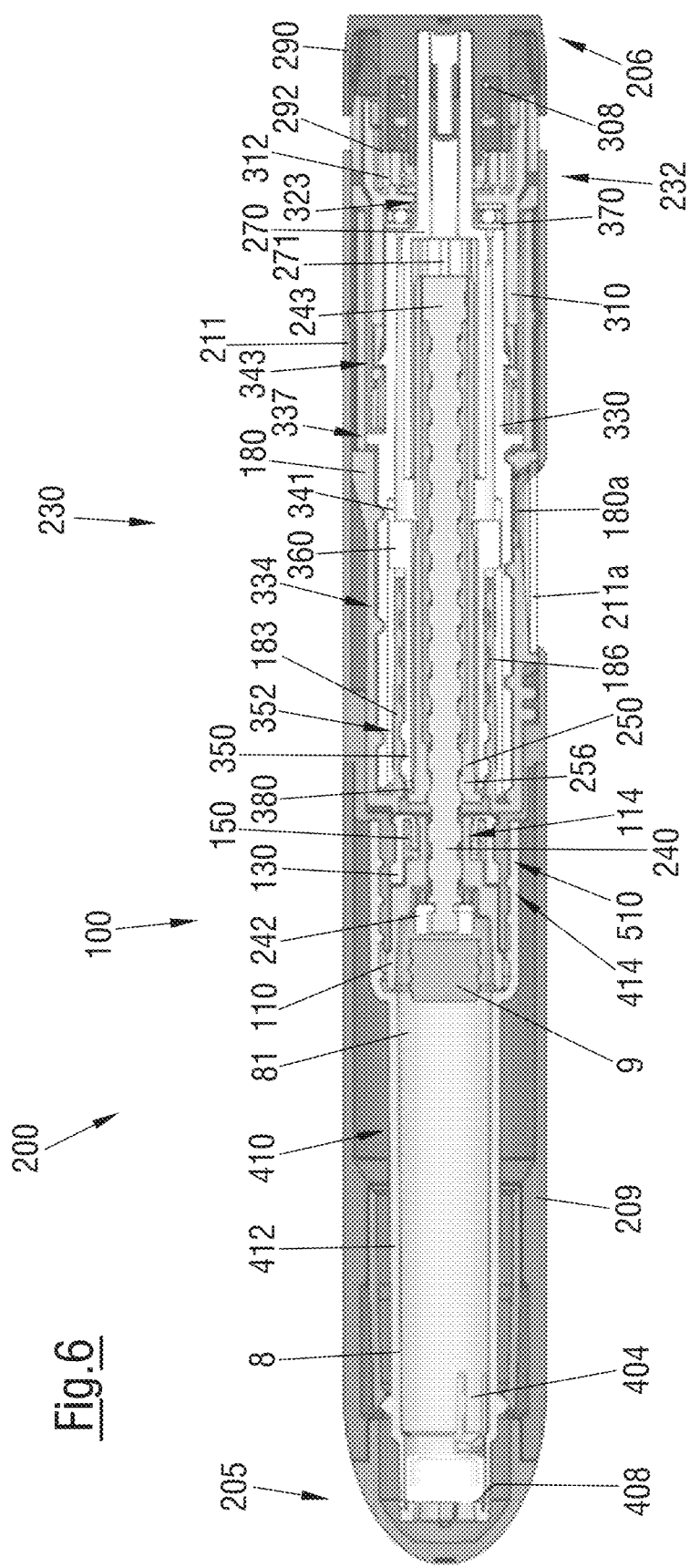
FIG. 6 is a longitudinal cross sectional view of the drug delivery device, the first dispensing unit and the cap through a second cross sectional plane perpendicular to the first cross sectional plane with the drug delivery device being in the dose setting state.
Figure 7:
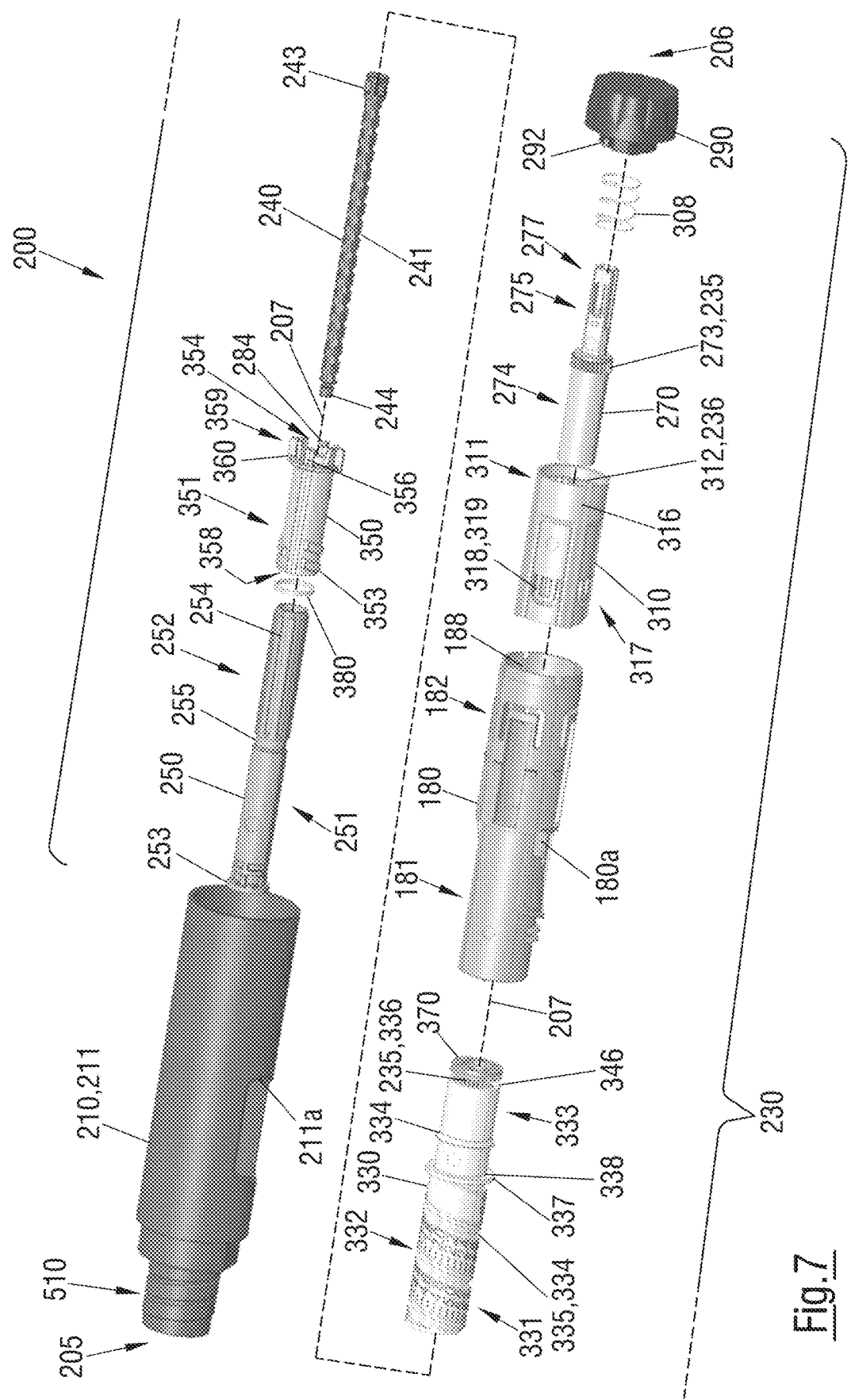
FIG. 7 is an exploded partial view of a dosing mechanism of the drug delivery device.

FIG. 5 and FIG. 6 show longitudinal cross sectional views of the drug delivery device 200 along two different planes that are orientated perpendicular to each other. FIG. 7 shows a partial exploded view of the components of the drug delivery device 200 that are visible in FIG. 5 and FIG. 6. The drug delivery device 200 comprises a dosing mechanism 230 that is configured to set a dose of drug to be delivered by the drug delivery device 200 and to expel the set dose by moving the plunger 9 in the proximal direction.

The dosing mechanism 230 comprises a piston rod assembly with a piston rod 240, which is elongated along the longitudinal axis 207, and a plunger disc 242 (see FIGS. 5 and 6) mounted to the proximal end of the piston rod 240. The piston rod assembly is configured to directly contact the plunger 9 by the plunger disc 242 and to advance the plunger 9 within the cartridge 8 upon movement of the piston rod assembly in the proximal direction. The piston rod 240 has a non-circular cross-section and an outer thread 241 that essentially covers its entire length. At its proximal end, the piston rod 240 comprises a disc connector 244 for receiving the plunger disc 242. At its distal end, the piston rod 240 comprises a stop feature 243, which terminates the outer thread 241 and is exemplarily configured as a thickened portion of the piston rod 240 having a larger radial extent than the minor diameter of the thread 241.

The piston rod 240 is located within the housing 210 that is within the outer housing 211 and the inner housing 180. In use, the piston rod 240 can protrude from the proximal end of the housing 210 such that the plunger disc 242 can be completely moved out of the housing 210 and into the cartridge 8. The piston rod 240 always protrudes from the proximal end of the inner housing 180. It can be completely retracted into the outer housing 211, for example, after resetting and/or prior to and/or directly after attaching a new dispensing unit 410 to the device 200. During the use of the device 200, the piston rod 240 is moved in the proximal direction to also protrude from the outer housing 211. The plunger disc 242 is permanently located outside the inner housing 180 and can be fully retracted into the outer housing 211, for example after completion of a resetting operation and/or prior to and/or directly after attaching a new dispensing unit 410 to the device 200.

The piston rod 240 is rotationally locked with respect to the housing 210 during both dose setting and dose delivery. In the present embodiment, the piston rod 240 is connected to the housing 210 via a resetting element 110 of a resetting mechanism 100 of the drug delivery device 200, see FIGS. 5 and 6. The resetting element 110 is rotationally fixed with respect to the housing 210 during both dose delivery and dose setting. It comprises a longitudinal opening 114 that receives the piston rod such that the plunger disc 242 is located at a proximal side of the opening 114 and the stop feature 243 is located at a distal side of the opening 114. The opening 114 is configured as a through hole with a non-circular cross section that matches the non-circular cross-section of the piston rod 240 thereby allowing axial movement but preventing rotational movement of the piston rod 240 with respect to the resetting element 110.

The piston rod 240 is surrounded by a hollow, generally cylindrical nut 250. The nut 250 is threadedly engaged with the thread 241 of the piston rod 240. In the present embodiment, the nut 250 comprises a threaded section with an inner thread 256 that engages the outer thread of the piston rod 240. The threaded section is located in a proximal part 251 of the nut 250, at the proximal end of the nut 250. With other embodiments, the threaded section can also cover other parts of the nut 250 or be located at other portions of the nut 250. The nut 250 further permanently surrounds the stop feature 243 of the piston rod 240, irrespective of the set and/or delivered doses.

The nut 250 has a distal part 252 that is surrounded by a proximal part 274 of a clutch member 270 of the dosing mechanism 230. The nut 250 is rotationally fixed to the clutch member 270 and axially movable with respect to the clutch member 270.

In the present embodiment, the nut 250 is engaged with the clutch member 270 by a splined connection between the nut 250 and the clutch member 270. The splined connection exemplarily comprises longitudinal grooves 254 that are located on the outer surface of the distal part 252 of the nut 250 and that are distributed around the circumference of the nut 250. The grooves 254 run parallel to the longitudinal axis 207 and are engaged by corresponding longitudinal ridges 271 that are distributed on an inner surface of the clutch member 270, see FIG. 6.

With other embodiments, a rotationally fixed and axially movable connection between the nut 250 and the clutch member 270 can also be achieved by different means, for example by a splined connection between longitudinal ridges on the outer surface of the nut 250 and corresponding longitudinal grooves on the inner surface of the clutch member 270. Additionally or alternatively, the connection can also be mediated by one or more intermediate members.

The clutch member 270 is, at its distal end, fixedly connected to the dose setting member 290 by a connection 277 that prevents both relative axial and relative rotational movement between the clutch member 270 and the dose setting member 290. With other embodiments of the drug delivery device 200, the dose setting member 290 and the clutch member 270 can also be configured as a single component. Alternatively, the connection between the clutch member 270 and the dose setting member 290 can also be mediated by one or more intermediate members.

In its proximal part 251, the nut 250 is surrounded by a driver 350. The driver 350 is configured as a hollow, generally cylindrical member. Furthermore, the driver 350 is axially fixed and rotationally movable with respect to the nut 250 and both axially and rotationally movable with respect to the housing 210 during both dose setting and dose delivery. Thereby, the driver 350 is threadedly engaged with the housing 210.

The inner housing 180 comprises at its proximal end an inner sleeve 183 that receives a proximal part 351 of the driver 350. The driver 350 comprises a thread 353 that engages with a drive thread 186 of the inner sleeve 183. In the exemplary embodiment, the thread 353 of the driver 350 is configured as an outer thread and the drive thread 186 is configured as an inner thread. The thread 353 is located on the proximal part 351 of the driver 350. With other embodiments, a threaded connection between the driver 350 and the housing 210 can also be achieved by other ways, for example by an outer thread on the housing 210 and an inner thread on the driver 350.

The dosing mechanism 230 furthermore comprises the dosing member 330. The dosing member 330 is configured as a hollow generally cylindrical member. It surrounds both the driver 350 and the clutch member 270. The dosing member 330 constitutes a dose setting sleeve of the drug delivery device 200.

The driver 350 is located within a proximal part 331 of the dosing member 330 and the clutch member 270 is located with its proximal part 274 in a distal part 333 of the dosing member 330.

The dosing member 330 is axially and rotationally movable with respect to the housing 210 during both dose setting and dose delivery. It is furthermore threadedly engaged with the housing 210 so that it is forced to move on a helical path with respect to the housing 210.

The dosing member 330 is located between the inner sleeve 183 and an outer wall of the inner housing 180. It has a thread 335 that is engaged with a dose thread 185 of the housing 210 (see FIG. 8). With the exemplary embodiment, the thread 335 of the dosing member 330 is configured as an outer thread and the dose thread 185 is configured as an inner thread located on an inner surface of the outer wall of the inner housing 180. With other embodiments, a threaded connection between the dosing member 330 and the housing 210 can also be realized in different ways. For example, the threaded connection could be disposed between the dosing member 330 and the inner sleeve 183 of the inner housing 180.

The dosing member 330 is configured as a dose indication member and comprises the optical markers 331 on its outer surface. The optical markers 331 form a helical scale with a pitch that corresponds to the pitch of the thread 335 on the outer surface of the dosing member 330.

The driver 350 is axially movable and rotationally fixed with respect to the dosing member 330 during both dose setting and dose delivery. With the exemplary embodiment, this is achieved by a splined connection between the driver 350 and the dosing member 330.

The driver 350 comprises radially extending longitudinal splines 360 that engage with corresponding longitudinal grooves 341 disposed on an inner surface of the dosing member 330 (see FIG. 6). The splines 360 are located in the distal part 359 of the driver 350 and the grooves 341 are located in a proximal part 332 of the dosing member 330. With other embodiments, the splined connection between the driver 350 and the dosing member 330 can also be achieved in different ways. For example, the driver 350 can comprise grooves that are engaged by corresponding splines of the dosing member 330.

The dose selector member 310 is configured as a hollow, generally cylindrical member. It constitutes a dose selector sleeve of the drug delivery device.

The dose selector member 310 is axially fixed and rotationally movable with respect to the dosing member 330. Therefore, the dose selector member 310 is forced to axially follow a movement of the dosing member 330 while the dosing member 330 is free to rotate with respect to the dose selector member 310, which itself is rotationally fixed with respect to the housing 210.

The dosing member 330 is received within the dose selector member 310. With the current embodiment, a proximal part 317 of the dose selector member 310 receives the distal part 333 of the dosing member 330. The clutch member 270, the proximal part 274 of which is located within the dosing member 330, axially extends with its distal part 275 from the dosing member 330. The distal part 275 of the clutch member 270 thereby extends through an opening 323 in a radially orientated inner wall 322 of the dose selector member 310 (see FIG. 5), which inner wall 322 separates the proximal part 317 of the dose selector member 310 from a distal part 311.

FIG. 8 shows a longitudinal cross sectional view of the dosing mechanism 230 of the drug delivery device 200 through the first plane prior to setting a dose to be delivered by the drug delivery device 200. To set the dose, the dose setting member 290 is gripped by a user and rotated with respect to the housing 210. This causes the clutch member 270 to rotate together with the dose setting member 290. Due to the rotationally fixed connection between the clutch member 270 and the nut 250, the nut 250 also rotates together with the dose setting member 290. Since the piston rod 240 is rotationally fixed with respect to the housing 210 and the piston rod 240 is threadedly engaged with the nut 250, rotation of the nut 250 causes the nut 250 to axially advance along the piston rod 240 in the distal direction. When increasing the set dose, the nut 250 travels in the distal direction, and when decreasing the set dose, the nut 250 travels in the proximal direction.

During dose setting, the dose setting member 290 is rotationally fixed with respect to the dosing member 330. This is achieved by a clutch mechanism 234 that comprises a first part 235 that acts between the dose setting member 290 and the dosing member 330.

The first part 235 of the clutch mechanism 234 comprises clutch elements 336 (see FIG. 7) that are located on the dosing member 330 and that engage, during dose setting, with corresponding clutch elements 273 located on the clutch member 270. The engagement between these clutch elements 336, 273 prevents relative rotational movement between the dose setting member 290 and the dosing member 330 while allowing axial movement for disengagement of the first part 235 of the clutch mechanism 234.

Since the first part 235 of the clutch mechanism 234 is closed during dose setting, the dosing member 330 rotates together with the dose setting member 270. The threaded engagement between the dosing member 330 and the housing 210 then causes the dosing member 330 to axially travel within the housing 210 during dose setting. Upon increasing the set dose, the dosing member 330 travels in the distal direction, and upon decreasing the set dose, the dosing member 330 travels in the proximal direction.

Since the dose selector member 310 is axially fixed with respect to the dosing member 330, distal movement of the dosing member 330 causes the dose selector member 310 to axially travel out of the housing 310 in the distal direction, thereby also moving the dose setting member 290 into the distal direction, while proximal movement of the dosing member 330 causes the dose selector member 310 to axially travel into the housing 210 thereby also moving the dose setting member 290 into the proximal direction.

As the dosing member 330 is rotationally fixed with respect to the driver 350, rotation of the dosing member 330 also causes the driver 350 to rotate together with the dose setting member 290. The threaded connection between the driver 350 and the housing 210 then causes the driver 350 to move in the distal direction when increasing the set dose and to move in the proximal direction when decreasing the set dose.

A first pitch of the threaded connection between the piston rod 240 and the nut 250 and a second pitch of the threaded connection between the driver 350 and the housing 210 are matched to each other to cause the nut 250 and the driver 350 to travel essentially the same axial distance upon rotational movement of the dose setting member 290. The first and second pitches are smaller than a third pitch of the threaded connection between the dosing member 330 and the housing 210. This causes the dosing member 330 to travel a larger axial distance upon rotation of the dose setting member 290 than the nut 250 and the driver 350.

With the device 200, the nut 250 and the clutch member 270 are only rotationally locked but free to move axially with respect to each other. This allows the clutch member 270 and the dose setting member 290 to travel larger distances in the axial direction during dose setting than the nut 250. Likewise, the driver 350 and the dosing member 330 are only rotationally locked but free to move axially with respect to each other. This allows the dosing member 330 to travel larger distances in the axial direction during dose setting than the driver 350.

FIG. 9 shows the dose setting mechanism 232 after a dose has been set. During dose setting, the dosing member 330 has traveled a first distance x in the distal direction, while the driver 350 has traveled a second distance y and the nut 250 has traveled a third distance z. The first distance x is larger than the second and third distances y, z.

Due to manufacturing tolerances, the first pitch of the threaded connection between the piston rod 240 and the nut 250 varies among different threaded connections between a minimum first pitch and a maximum first pitch and the second pitch of the threaded connection between the driver 350 and the housing 210 varies among different threaded connections between a minimum second pitch and a maximum second pitch. With the drug delivery device 200, the maximum first pitch is smaller than or at most equal to the minimum second pitch. This ensures that the second distance y traveled by the driver 350 in the distal direction is always slightly larger than the third distance z traveled by the nut 250.

The dose setting member 290, which also acts as an actuation member to effect injection of the set dose, is axially movable with respect to the dose selector member 310 between a distal position and a proximal position. A biasing member 308, which is configured as a compression spring, biases the dose setting member 290 into the distal position during dose setting.

To effect ejection of a set dose, the user of the device 200 pushes the dose setting member 290 from the distal position into the proximal position. This transfers the dosing mechanism 230 from a dose setting state into a dose delivery state. The dosing mechanism 230 of the drug delivery device 200 is configured to allow for a setting of the dose to be injected when the dose delivery device 200 and the dosing mechanism 230 are in the dose setting state, while it is configured to enable the delivery of the set dose when the dose delivery device 200 and the dosing mechanism 230 are in the dose delivery state.

FIG. 10 shows the dosing mechanism 230 after the dose has been set and the dosing mechanism 230 has been transferred from the dose setting state into the dose delivery state. Moving the dose setting member 290 into the proximal direction also causes the clutch member 270 to move into the proximal direction. Thereby, the first part 235 of the clutch mechanism 234 opens and the clutch elements 273 of the clutch member 270 are disengaged from the clutch elements 336 of the dosing member 330. Therefore, the dosing member 330 and the driver 350 are free to rotate with respect to the dose setting member 290, the clutch member 270 and the nut 250.

Proximal movement of the dose setting member 290 with respect to the dose selector member 310 at the same time causes a second part 236 of the clutch mechanism 234 to close and to rotationally lock the nut 250 with respect to the piston rod 240 and the housing 210. The second part 236 of the clutch mechanism 234 acts between the dose selector member 310 and the dose setting member 290 and is further described in connection with FIG. 12 and FIG. 13 below.

Further pushing the dose setting member 290 in the proximal direction then causes the dose selector member 310 to linearly move back into the housing 210. The dose selector member 310 thereby pushes against the dosing member 330, which causes the dosing member 330 to rotate due to its threaded engagement with the housing 210. Rotation of the dosing member 330 is transferred to the driver 350, which therefore also moves into the proximal direction due to its threaded engagement with the housing 210.

The difference in the pitches of the threaded connection between the dosing member 330 and the housing 210 and the threaded connection between the driver 350 and the housing 210 thereby causes a mechanical advantage that translates a first axial force exerted by the user and acting on the dosing member 330 into a second axial force exerted by the driver 350. With the dose delivery device 200, the second axial force is larger than the first axial force.

When moving in the proximal direction during dose delivery, the driver 350 pushes axially against the nut 250 and thereby advances the nut 250 in the proximal direction. Since the nut 250 is blocked from rotation with respect to the piston rod 240 during dose delivery due to its connection to the housing 210 via the clutch member 270, the dose setting member 290 and the dose selector member 310, the threaded connection between the nut 250 and the piston rod 240 axially fixes the nut 250 and the piston rod 240 with respect to each other during dose delivery. Therefore, the axially moving nut 250 urges the piston rod 240 to also move in the proximal direction and to thereby advance the plunger 9 to expel the drug from the drug compartment 81.

The housing 250, the dosing member 330, which is threadedly engaged with the housing 250 and rotationally respect to the driver 350, the driver 350, which is also threadedly engaged with the housing 250, and the nut 250, which is pushed in the proximal direction by the driver 350 during dose delivery, form an advancement mechanism of the drug delivery device 200. The advancement mechanism is configured to translate axial movement of the dosing member into axial advancement of the piston rod during dose delivery. Thereby, the advancement mechanism comprises a gearing mechanism provided by the differently pitched threaded connections between the housing 250 and the dosing member 330 on the one hand and between the housing 250 and the driver 350 on the other hand.

Closing of the second part 236 of the clutch mechanism 234 upon dose delivery also rotationally locks the dose setting member 290 to the housing 210 during dose delivery. This ensures that the dose setting member 290 does not rotate during dose delivery and therefore avoids the user being disturbed by a rotation of the dose setting member 290 when the user presses the dose setting member 290 to effect dose delivery. The drug delivery device 200 does not comprise any component that would be accessible by a user from the outside of the device 200 and that rotates during dose delivery. This helps to ensure a safe delivery of the drug during injection.

FIG. 11 shows the dosing mechanism 230 after the dose has been delivered. The nut 250, the driver 350 and the dosing member 330 have returned to their initial positions while the piston rod 240 has been advanced in the proximal direction by the third distance z. Since the piston rod 240 presses against the plunger 9 via the plunger disc 242, the plunger 9 has also been moved by the third distance z in the proximal direction.

Figure 12:
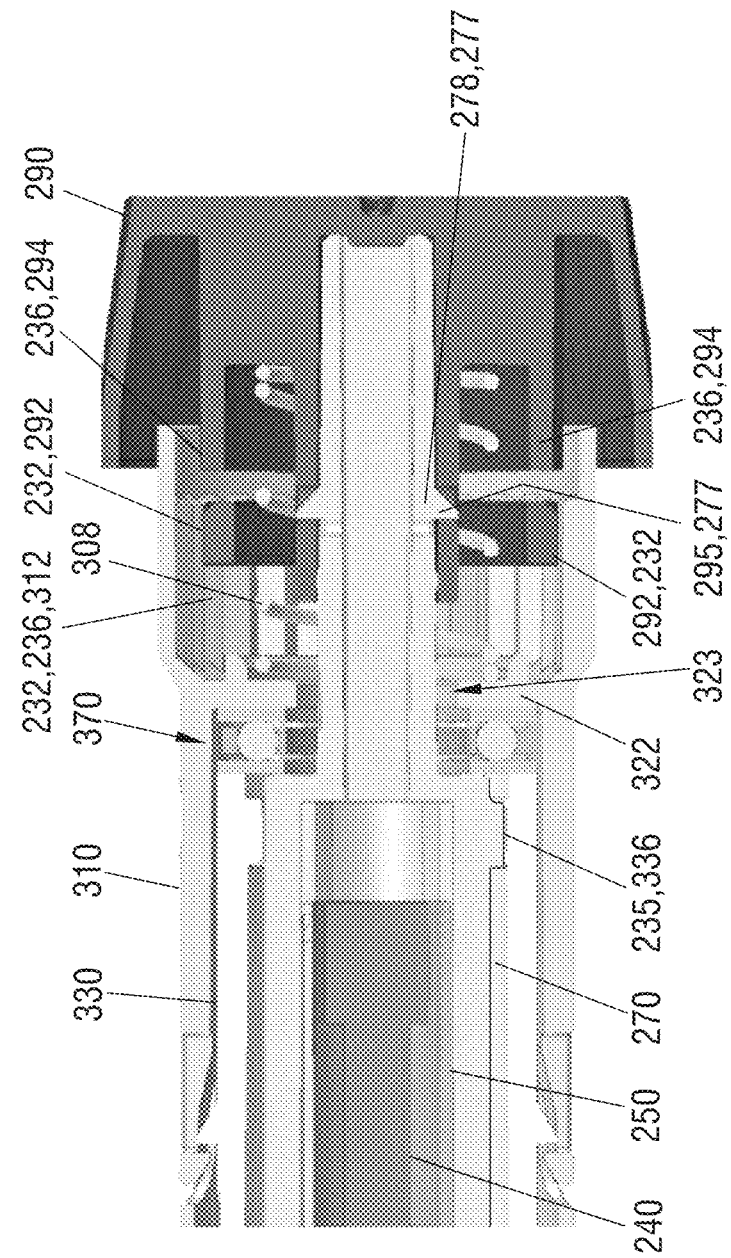
FIG. 12 is a clutch mechanism of the dosing mechanism in a dose setting state.
Figure 13:
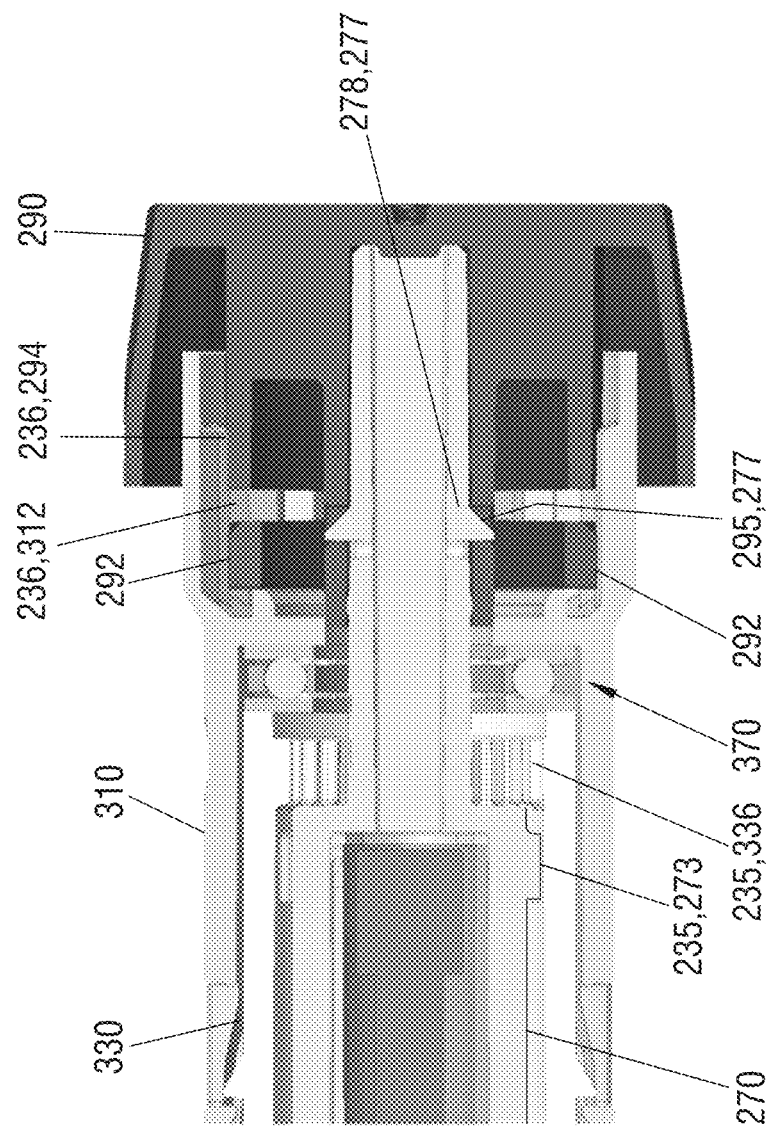
FIG. 13 is the clutch mechanism in a dose delivery state.

FIG. 12 shows the clutch mechanism 234 of the dosing mechanism 230 in the dose setting state and FIG. 13 shows the clutch mechanism 234 in the dose delivery state.

In the dose setting state shown in FIG. 12, the dose setting member 290 and the clutch member 270 are in their distal position with respect to the dose selector member 310. The first part 235 of the clutch mechanism 234 is closed and rotationally fixes the clutch member 270 to the dosing member 330.

The second part 236 of the clutch mechanism 234 is configured to rotationally fix the dose setting member 290 to the dose selector member 310 during dose delivery. The second part 236 comprises clutch elements 294 (see also FIG. 15) that are provided at the dose setting member 290. As can be seen from FIG. 13, moving the dose setting member 290 into the proximal position brings the clutch elements 294 into engagement with teeth 312 of the dose selector member 311, thereby rotationally locking the dose setting member 290 to the dose selector member 311. The teeth 312 are disposed on the inner surface of the distal part 311 of the dose selector member 310. The teeth 312 constitute clutch elements of the dose selector member 310. As can also be seen from FIG. 13, pressing the dose setting member 290 into the proximal position disengages the clutch elements 273 of the clutch member 270 from the clutch elements 336 of the dosing member 330.

Generally speaking, the clutch mechanism 234 rotationally locks the nut 250 to the dosing member 330 and to the driver 350 during dose setting, while it rotationally locks the nut 250 to the piston rod 240 and to the housing 210 during dose delivery. Furthermore, the clutch mechanism 234 rotationally locks the dose setting member 290 to the dosing member 330 during dose setting and to the housing 210 during dose delivery.

The dosing mechanism 230 of the drug delivery device 200 further comprises a dose definition mechanism 232 that acts between two members of the dosing mechanism 230 that are rotationally movable with respect to each other during dose setting. The dose definition mechanism 232 defines distinct rotational positions of the dose setting member 290 with respect to the housing 210 that correspond to individual settable doses of the drug to be ejected by the dosing mechanism 230.

With the drug delivery device 200, the dose definition mechanism 232 acts between the dose selector member 310 and the dose setting member 290, as can be seen from FIGS. 12 and 13. Thereby, the dose definition mechanism 232 is realized by direct engagement between the dose setting member 290 and the dose selector member 310. With other embodiments of dose delivery devices according to the present disclosure, the dose definition mechanism 232 can also act between the dose selector member 310 and the dose setting member 290 via additional elements that are located between the dose selector member 310 and the dose setting member 290. Such an additional element could be, for example, the clutch member 270 and/or the dosing member 330.

As can also be seen from FIG. 12, the dose definition mechanism 232 comprises at least one element 292 that engages with at least one corresponding functional feature, namely with the one of the teeth 312, when the dose setting member 290 reaches a rotational position with respect to the housing 210 that corresponds to a respective dose defined by the functional feature 312. Engagement between the element 292 and the functional feature 312 then provides audible and/or tactile feedback to the user of the drug delivery device 200. As can be seen from FIG. 12, the element 292 is provided at the dose setting member 290. In particular, it is configured as an integral element of the dose setting member 290.

At least one of the element 292 and the functional feature 312 are configured as a flexible element that deflects in a radial direction upon engagement between the element 292 and the functional feature 312. With the drug delivery device 200, the element 292 is configured as such a flexible element.

With the teeth 312, the drug delivery device 200 comprises several functional features 312 that are circumferentially distributed around the longitudinal axis 207 to define a multitude of settable doses. Furthermore, the dose definition mechanism 232 of the drug delivery device 200 comprises a multitude of elements 292, namely four elements 292, that are distributed around the longitudinal axis 207. A relative position between the individual functional features 312 and the individual elements 292 is chosen in a way that at each rotational position of the dose setting member 290 with respect to the housing 210, which correspond to a settable dose, all elements 292 engage with a respective one of the functional features 312. Other embodiments of the drug delivery device 200 can also comprise other numbers of elements 292, for example a single element 292.

With the drug delivery device 200, the functional features 312 are located on an inner surface of the dose selector member 310 and the elements 292 are located on an outer surface of the dose setting member 290. Furthermore, the element 292 and the three further elements 292 are configured as flexible arms. They constitute integral parts of the dose setting member 290 and are provided at a proximal end of the dose setting member 290.

The teeth 312 disposed on the dose selector member 310 constitute both clutch elements of the second part 236 of the clutch mechanism 234 and functional features, that is dose stops, of the dose definition mechanism 232.

Figure 14:
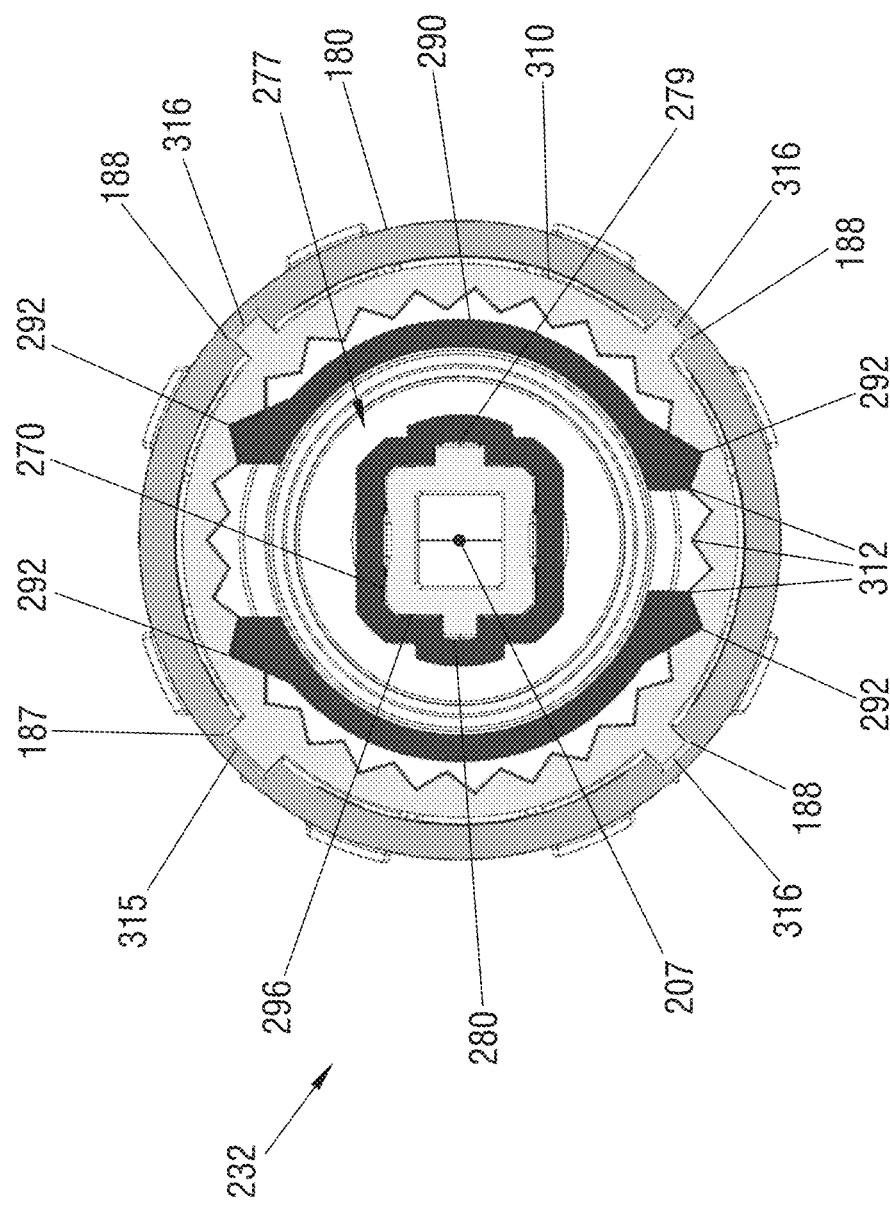
FIG. 14 is a radial cross sectional view of a dose definition mechanism of the drug delivery device.
Figure 15:
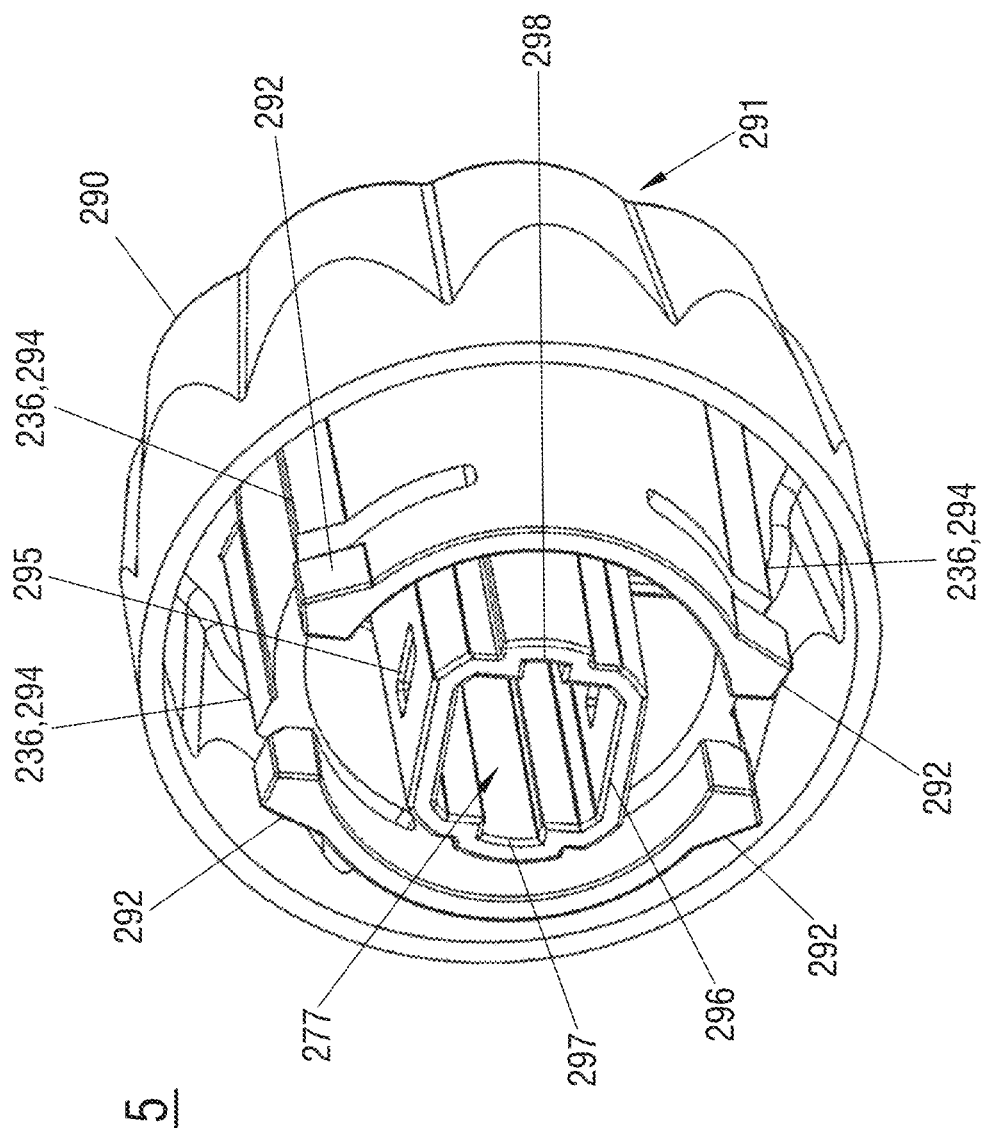
FIG. 15 is a perspective view of a proximal side of a dose setting member of the drug delivery device.
Figure 16:
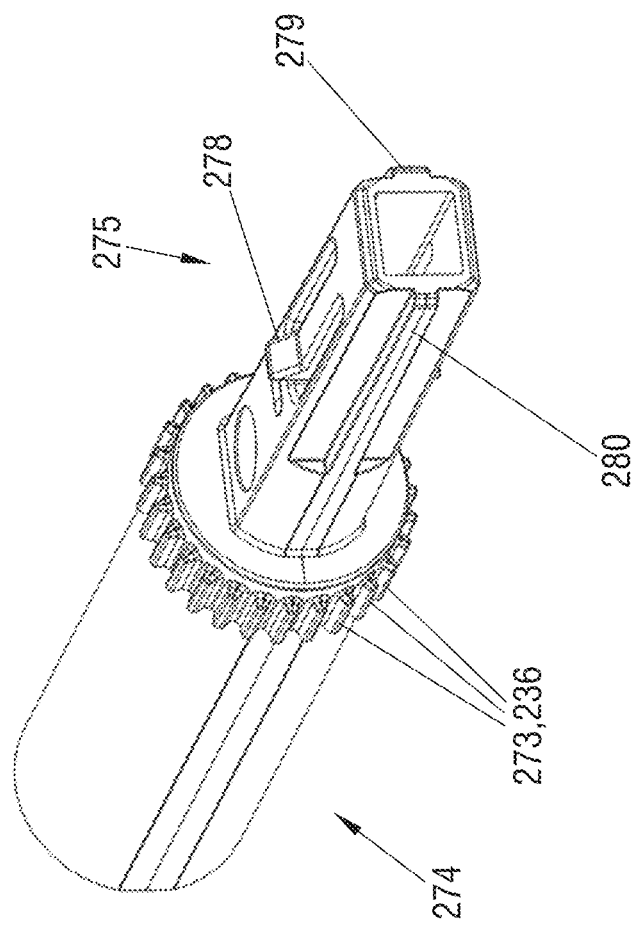
FIG. 16 is a perspective view of a distal side of a clutch member of the drug delivery device.

FIG. 14 shows a radial cross sectional view of the dose definition mechanism 232 perpendicular to the longitudinal axis 207. FIG. 15 shows a perspective view of a proximal side of the dose setting member 290 of the drug delivery device and FIG. 16 shows a perspective view of a distal side of the clutch member 270.

As can be seen from FIG. 14, the dose definition mechanism 232 defines an uneven number of distinct rotational positions of the dose setting member 290 with respect to the housing 210 that correspond to settable doses, namely 27 rotational positions/settable doses. To ensure correct rotational alignment between the first part 235 and the second part 236 of the clutch mechanism 234, the dose setting member 290 is connected to the clutch member 270 by a connection 277 having a coding feature that only allows a single relative rotational orientation between the clutch member 270 and the dose setting member 290.

The connection 277 comprises a non-circular, namely rectangular, opening 296 within the dose setting member 290, the opening 296 receiving the non-circular, namely rectangular, distal part 275 of the clutch member 270. The coding feature then comprises a first longitudinal ridge 279 and a second longitudinal ridge 280, whereby the longitudinal ridges 279, 280 radially extend from opposite sides of the distal part 275 of the clutch member 270. The first ridge 279 is received in a corresponding first longitudinal groove 297 located within the opening 296 of the dose setting member 290 and the second ridge 280 is received within a corresponding second longitudinal groove 298 of the dose setting member 290. The first ridge 279 and the first groove 297 have a width that differs from the respective widths of the second ridge 280 and the second groove 298. With other embodiments of the drug delivery device 200, the coding feature of the connection 277 could also be realized in a different way for example by ridges disposed on the dose setting member 290 and corresponding grooves disposed on at the clutch member 270.

To permanently and non-releasably couple the dose setting member 290 to the clutch member 270 during assembly of the drug delivery device 200, the clutch member 270 is locked to the dose setting member 290 by a snap-fit connection 277. As can be seen, for example, in FIG. 15 and FIG. 16, this snap-fit connection 277 comprises two flexible snap hooks 278 that are located at opposing sides of the distal part 275 of the clutch member 270. Upon insertion of the distal part 275 into the opening 296 of the dose setting member 290, the snap hooks 278 engage with corresponding recesses 295 disposed in the side surfaces of the opening 296. With other embodiments, the non-releasable connection 277 can also be provided in different ways, for example by at least one snap-hook located at the dose setting member 290 and at least one corresponding recess located on the clutch member 270.

As it will be described in further detail below, axial positions of the dosing member 330 that correspond to a minimum and a maximum settable dose are defined by interaction between the dosing member 330 and the inner housing 180. A connection between the dose selector member 310 and the inner housing 180 is therefore configured in a way that these axial positions correspond to settable doses defined by the dose definition mechanism 232.

With the drug delivery device 200, such a connection, which is shown in FIG. 14, is achieved by restricting a relative rotational orientation between the dose selector member 310 and the inner housing 180 to a single orientation. The connection is established by a first longitudinal ridge 315, which is disposed on the outer surface of the dose selector member 310 and which is received in a corresponding first longitudinal groove 187 disposed on an inner surface of the inner housing 180. The first longitudinal ridge 315 has a width that is different than the width of three further longitudinal ridges 316 that are distributed over the remaining outer surface of the dose selector member 310. The further longitudinal ridges 316 engage with corresponding further longitudinal grooves 188 that are distributed over the remaining inner surface of the inner housing 180 and have corresponding widths that are different from the width of the first longitudinal groove 187.

In general, the first longitudinal ridge 315 and the first longitudinal groove 187 form a first longitudinal splined connection and the further longitudinal ridges 316 and the further longitudinal grooves 188 form at least a second longitudinal splined connection, the first longitudinal splined connection having a different transverse width than the second longitudinal splined connection. With other embodiments, the connection between the dose selector member 310 and the inner housing 180 could also be achieved in different ways, for example by splined connections having grooves located on the dose selector member 310 and ridges located on the inner housing 180.

Figure 17:
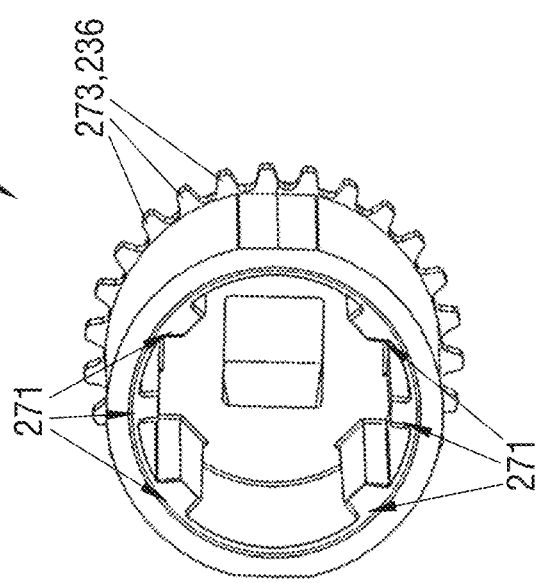
FIG. 17 is a perspective view of a proximal side of the clutch member of the drug delivery device.

FIG. 17 shows a perspective view of a proximal side of the clutch member 270 of the drug delivery device 200. On the inner surface of its proximal part 274, the clutch member 270 has the longitudinal ridges 271 that engage with the longitudinal grooves 254 of the nut 250 to rotationally lock the clutch member 270 with respect to the nut 250 while at the same time allowing relative axial movement. Generally speaking, the longitudinal ridges 271 and the corresponding longitudinal grooves 254 form a splined connection between the clutch member 270 and the nut 250. With other embodiments, a rotationally fixed and axially movable connection between the clutch member 270 and the nut 250 could also be achieved by other means, for example, by longitudinal ridges disposed on the nut 250 and corresponding grooves disposed on the clutch member 270.

Figure 18:
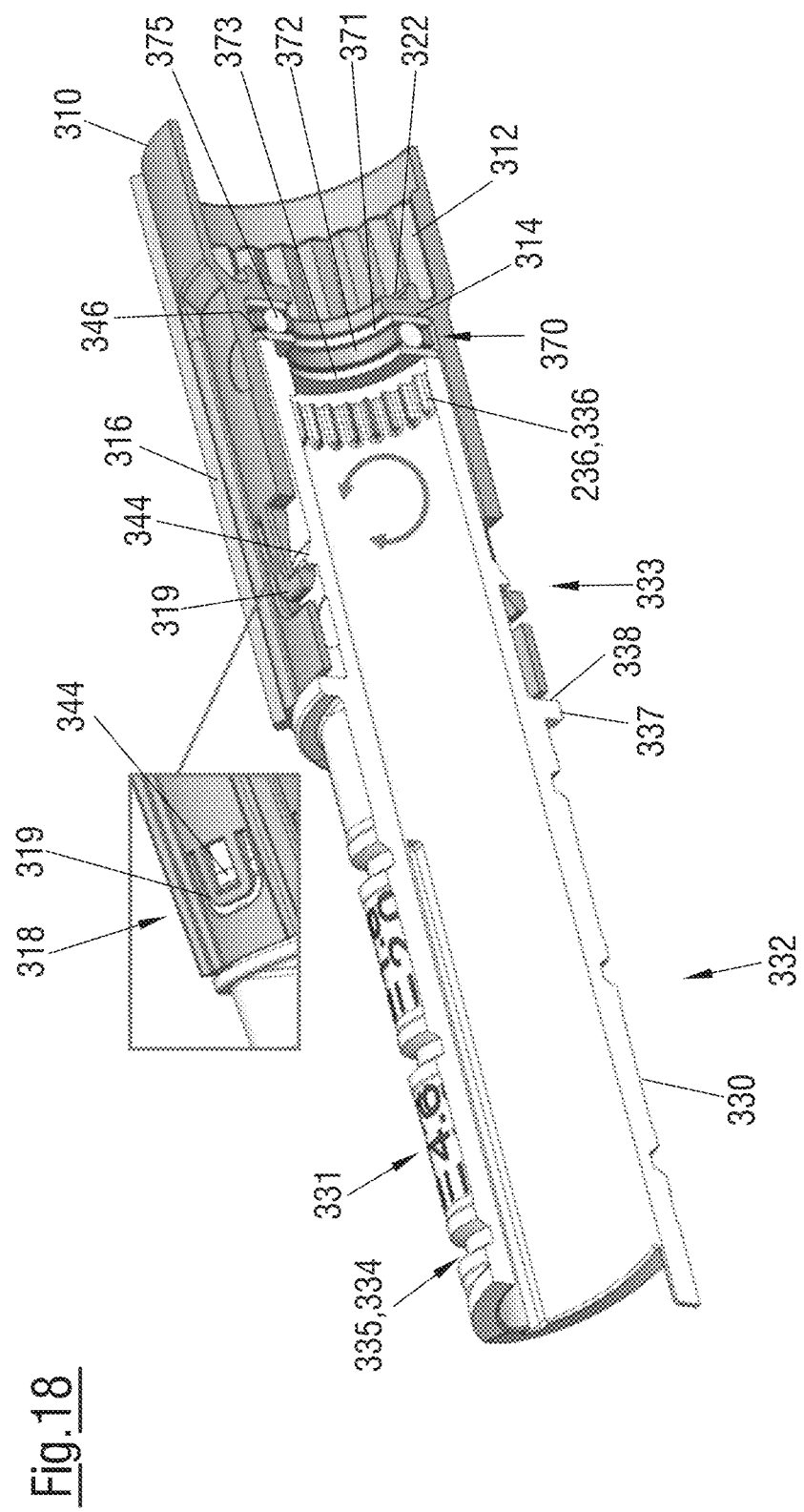
FIG. 18 is a longitudinal cross sectional view of a dosing member and a dose selector member of the drug delivery device with a first friction reduction mechanism.

FIG. 18 shows a longitudinal cross sectional view of the dosing member 330 and the dose selector member 310 of the drug delivery device 200. The drug delivery device 200 comprises a friction reduction mechanism that acts between the dosing member 330 and the dose selector member 310. The friction reduction mechanism is configured to reduce friction upon relative rotational movement between the dosing member 330 and the dose selector member 310.

The friction reduction mechanism comprises a ball bearing 370 which is disposed between a distal surface 346 of the dosing member 330 and a contact surface 314 of the dose selector member 310. The contact surface 314 is thereby provided by the proximal front surface of the radial inner wall 322 of the dose selector member 310. The distal surface 346 generally is a distally facing surface of the dosing member 330. With the drug delivery device 200, the distal surface 346 is a distal end surface of the dosing member 330. With other embodiments, the distal surface 346 could also be located at a different position of the dosing member 330.

When increasing the dose during dose setting, a distally directed axial force is transferred from the dosing member 330 via the ball bearing 370 to the dose selector member 310. When pushing the dose selector member 310 in the proximal direction during injection, a proximally directed axial force is transferred from the dose selector member 310 via the ball bearing 370 to the dosing member 330.

The ball bearing 370 comprises several balls 375 that are sandwiched between a distal disc 371 touching the contact surface 314 of the dose selector member 310 and a proximal disc 372 contacting the distal surface 346 of the dosing member 330. Furthermore, the ball bearing 370 comprises a holder 372, which is sandwiched between the distal disc 371 and the proximal disc 372. The holder 372 surrounds the balls 375 in the radial direction and holds them into place.

The dose selector member 310 is axially fixed to the dosing member 330. Distal movement of the dose selector member 310 with respect to the dosing member 330 is prevented by a snap-fit connection. The snap-fit connection comprises a circumferential annular ridge 344 on an outer surface of the dosing member 330 and at least one, namely four, flexible members 319 formed on the dose selector member 310. When moving the dose selector member 310 in the proximal direction over the dosing member 330, the flexible members 319 snap over the annular ridge 344 and engage with a proximal front surface of the annular ridge 344. With other embodiments, distal movement of the dose selector member 310 can also be achieved by a different connection, for example, by flexible members of the dosing member 330 engaging with an annular ridge of the dose selector member 310. Proximal movement of the dose selector member 310 with respect to the dosing member 330 is prevented by the contact surface 314 of the dose selector member 310 resting via the ball bearing 370 against the distal end surface 346 of the dosing member 330.

With other embodiments of the drug delivery device 200, the bearing element 370 can also be configured in other ways. For example, the bearing element 370 can also be configured as a disc bearing, such as a single annular disc made from a low-friction material, such as PTFE.

Figure 19:
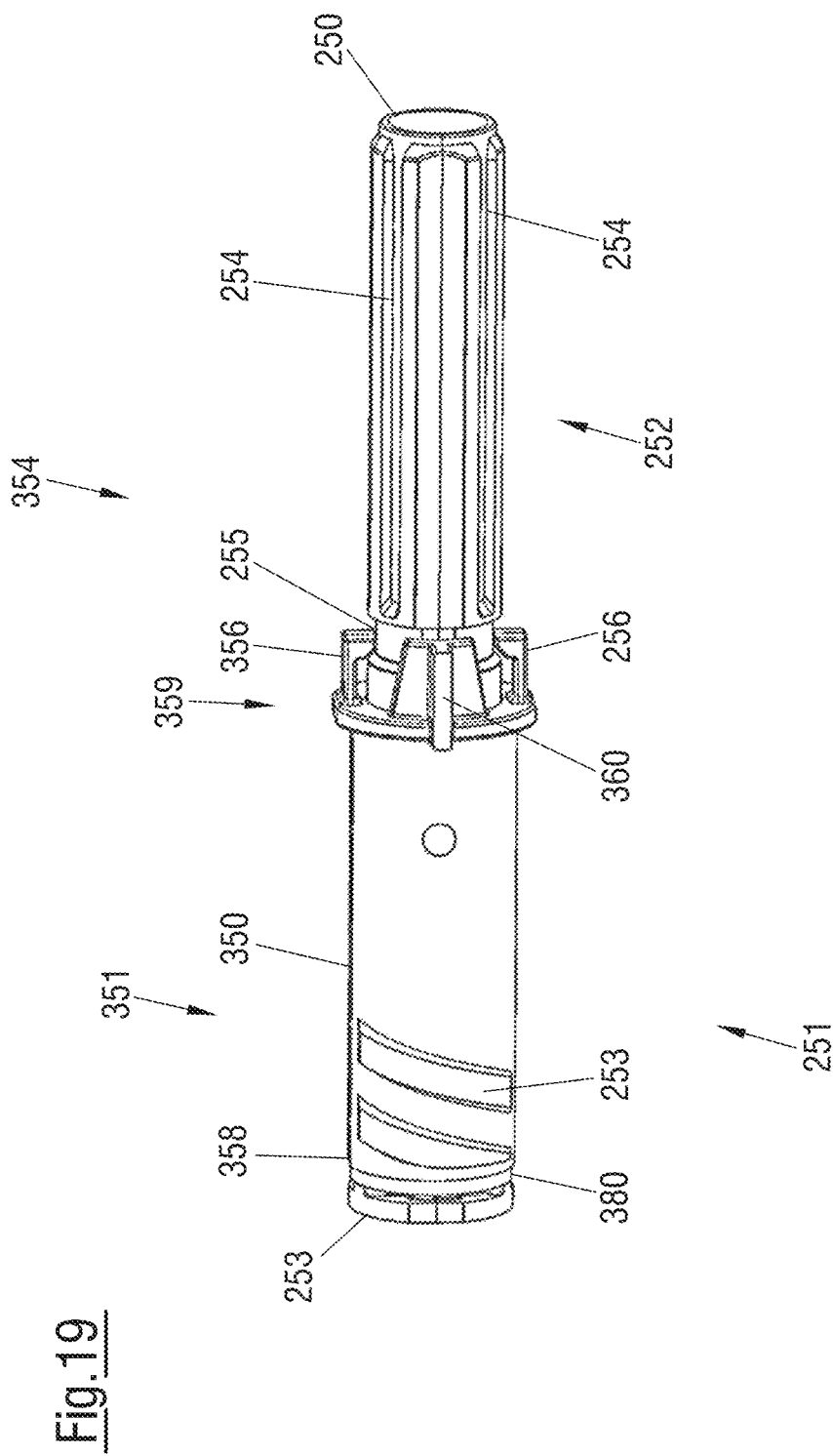
FIG. 19 is a perspective view of a connection between a nut and a driver of the drug delivery device with a second friction reduction mechanism.

FIG. 19 shows a perspective view of a connection 354 between the nut 250 and the driver 350 of the drug delivery device 200. The connection 354 is configured to axially restrain the driver 350 with respect to the nut 250 and to allow relative rotational movement between the nut 250 and the driver 350.

The connection 354 comprises two flexible arms 356 that are formed at a distal end of the driver 350 and that radially protrude inwardly to engage with an annular detent 255 between the proximal and distal parts 251, 252 of the nut 250. When moving the driver 350 distally with respect to the nut 250, the flexible arms 356 abut against the distal side surface of the annular detent 255. A clearance is disposed between the distal side surface and the flexible arm 356 to allow the nut 250 and the driver 350 to travel different distances into the distal direction during dose setting.

The drug delivery device 200 comprises a further friction reduction mechanism that is configured to reduce friction between the nut 250 and the driver 350 upon relative rotational movement with respect to each other during dose delivery. The further friction reduction mechanism comprises a bearing element 380 that is positioned between the driver 350 and the nut 250.

The bearing element 380 is located between a proximal front surface 358 of the driver 350 and a protrusion 253 located at the proximal end of the nut 250. The proximal protrusion 253 defines a rim that radially extends from the nut 250. When rotating into the inner sleeve 183 of the inner housing 180 during dose delivery, the proximal front surface 358 of the driver 350 pushes via the further bearing element 380 against the protrusion 253 and thereby also pushes the nut 250 in the proximal direction.

The bearing element 380 is configured as a bearing disc made from a low-friction material, such as PTFE. With other embodiments, the bearing element 380 could also be configured as a different type of bearing, for example as a ball bearing.

With the drug delivery device 200, the driver 350 is in general configured to axially advance the nut 250 during dose delivery by indirectly transferring an axial force to the nut 250, that is by transferring the axial force to the nut via 250 via one or more intermediate members, namely the bearing element 380.

The piston rod 240 is rotationally fixed with respect to the housing 210 at least during dose delivery and the nut 350 and the piston rod 240 are rotationally fixed with respect to each other during dose delivery so that the threaded connection 241, 256 between nut 250 and piston rod 240 axially locks the nut 250 with the piston rod 240 during dose delivery. Therefore, the nut 250 and the piston rod 240 are configured to simultaneously move axially during dose delivery as if they were a single member.

During dose setting, the nut 250 is configured to rotate with respect to the piston rod 240. Thereby, the piston rod 240 is rotationally locked to the housing 210 also during dose setting and the nut 250 is configured to rotated with respect to the housing 210 during dose setting. Rotation of the nut 250 then axially advances the nut 250 with respect to the piston rod 240 during dose setting due to the threaded connection 241, 256 between nut 250 and piston rod 240. Axial advancement of the nut 250 with respect to the piston rod 240 and/or with respect to the housing 210 then also defines the axial advancement of the piston rod 240 with respect to the housing 210 during dose delivery.

Figure 20:
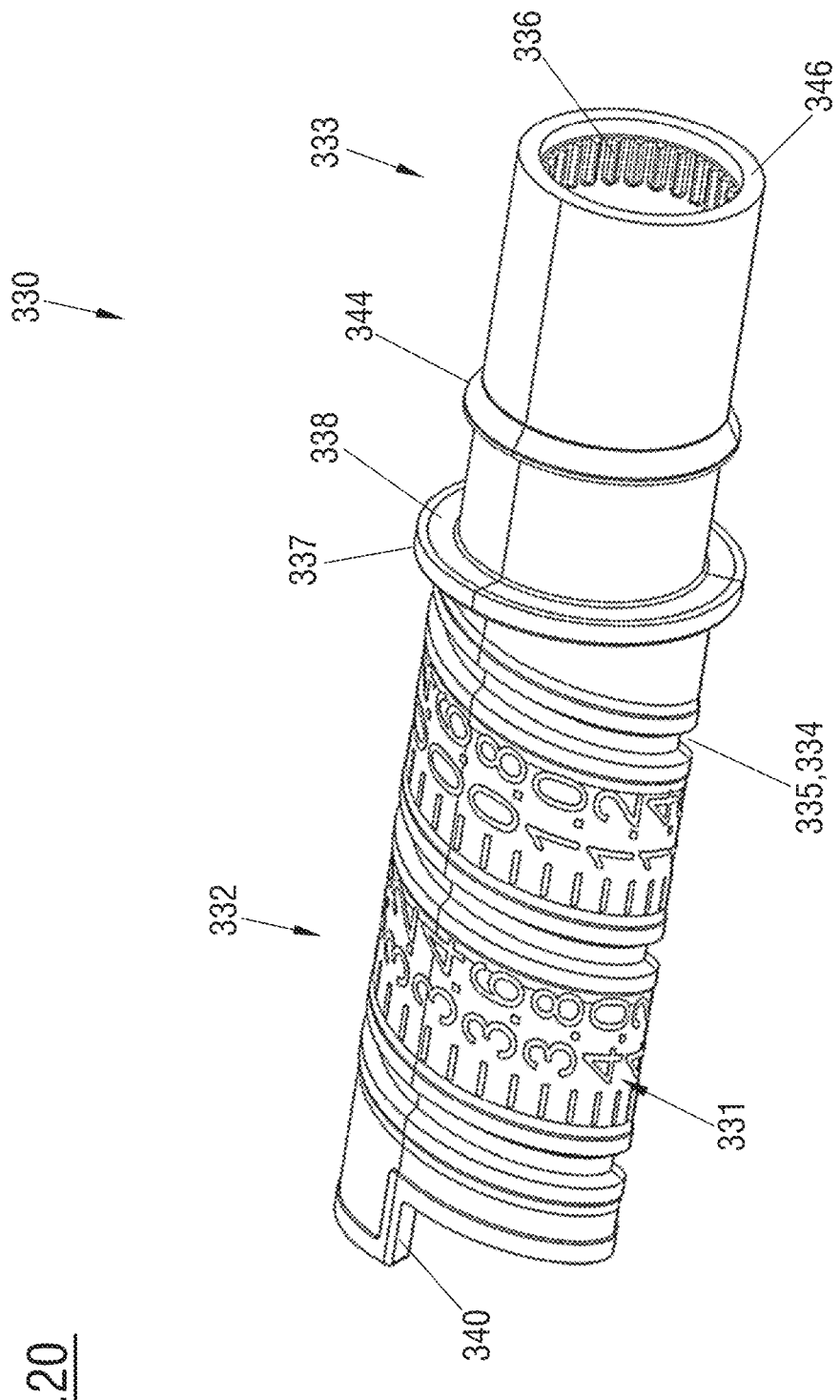
FIG. 20 is a perspective view of a dosing member of the drug delivery device.

FIG. 20 shows a perspective view of the dosing member 330 of the drug delivery device 200. The dosing member 330 comprises a maximum dose stop 337 that is configured to engage with the inner housing 180 upon setting a maximum dose. Engagement of the maximum dose stop 337 with the inner housing 180 thereby limits further axial movement of the dosing member 330 in the distal direction and defines the axial and rotational position of the dosing member 330 that corresponds to the maximum dose settable by the dosing mechanism 230.

Figure 21:
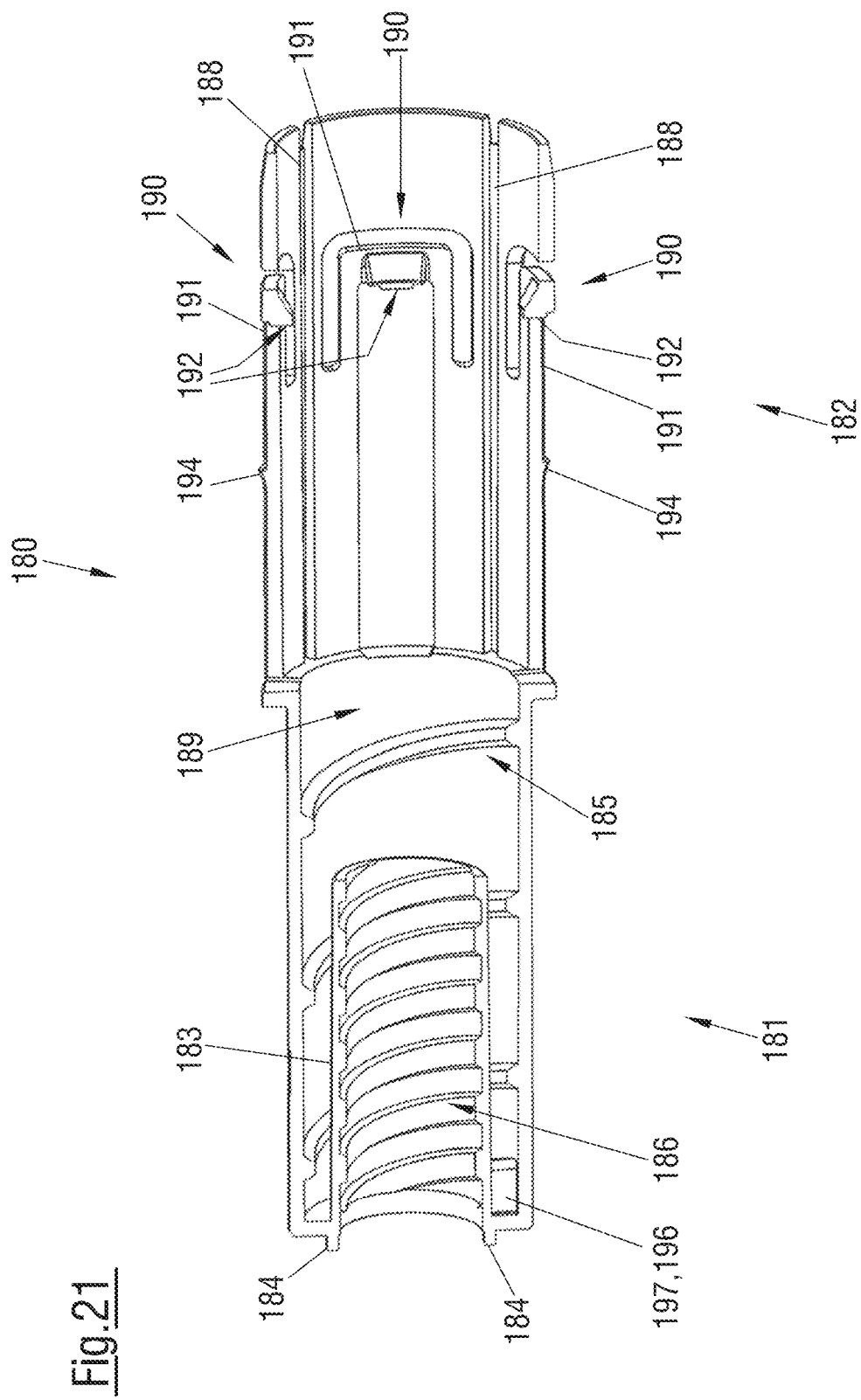
FIG. 21 is a longitudinal partial cross sectional view of an inner housing of the drug delivery device.

As can be seen from FIG. 21, which shows the inner housing 180 in a longitudinal cut through the longitudinal axis 207, the inner housing 180 comprises at least one maximum stop feature 190, namely four maximum stop features 190. The maximum stop features 190 are formed as integral parts of the inner housing 180. They each comprise a flexible hook 191 that radially protrudes inwardly into a housing cavity 189 of the inner housing 180 that receives the dosing member 330. The flexible hooks 191 each comprise a limiting surface 192 that is orientated perpendicular to the longitudinal axis 207 and faces into the proximal direction.

Upon insertion of the dosing member 330 into the housing cavity 189, the flexible hooks 191 snap over the maximum dose stop 337 to subsequently limit axial movement of the dosing member 330 into the distal direction. When setting the maximum dose, a distal stopping surface 338 of the maximum dose stop 337 abuts against the limiting surfaces 192 of the maximum stop features 190. The distal stopping surface 338 is configured as a side surface of the maximum dose stop 337 and is orientated perpendicular to the longitudinal axis 207.

As can be seen from FIG. 20, the dosing member 330 also comprises a zero dose stop 340 that defines the rotational and axial position of the dosing member 330 that corresponds to a zero dose or no set dose. The zero dose stop 340 is located at the proximal end of the dosing member 330. It is configured as a limiting surface that is orientated parallel to the longitudinal axis 207. The limiting surface forms a side surface of a cut-out at the proximal end of the dosing member 330.

When reaching the zero-dose position, the zero dose stop 340 engages with a zero stop feature 196 of the inner housing 180, which is shown in FIG. 21. The zero stop feature 196 is located at the proximal end of the housing cavity 189. Like the zero dose stop 340, the zero stop feature 196 is also configured as a limiting surface that is orientated parallel to the longitudinal axis 207. Furthermore, the limiting surface of the zero stop feature 196 is orientated parallel to the limiting surface of the zero dose stop 340.

The zero dose stop 340 engages with the zero stop feature 196 in a contact plane that is angled with respect to a radial plane orientated perpendicular to the longitudinal axis 207. With the present embodiment, the contact plane is orientated parallel to the limiting surfaces that are provided by the zero dose stop 340 and the zero stop feature 196.

Figure 22:
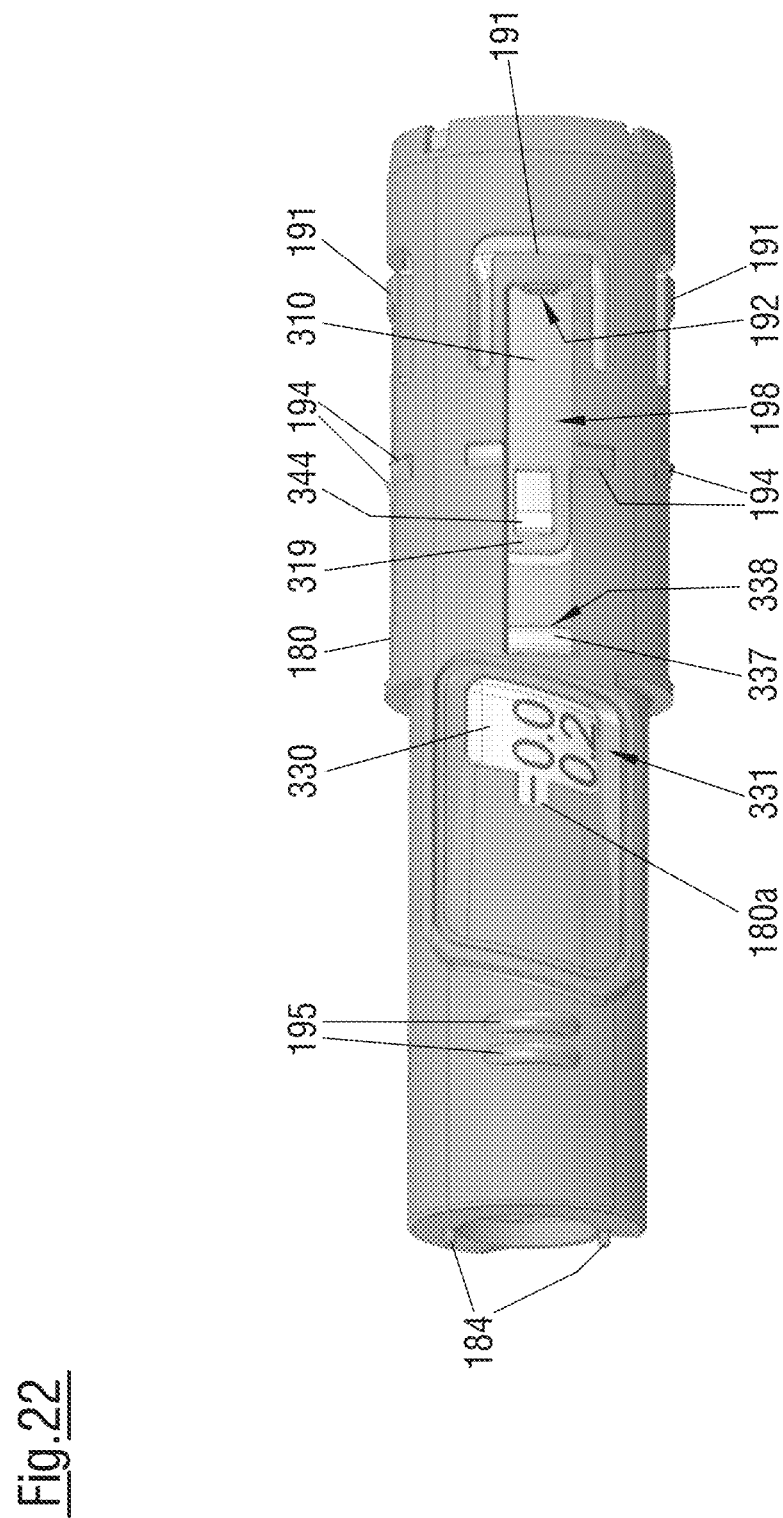
FIG. 22 is a perspective view of the inner housing with the dosing member in a zero-dose position.
Figure 23:
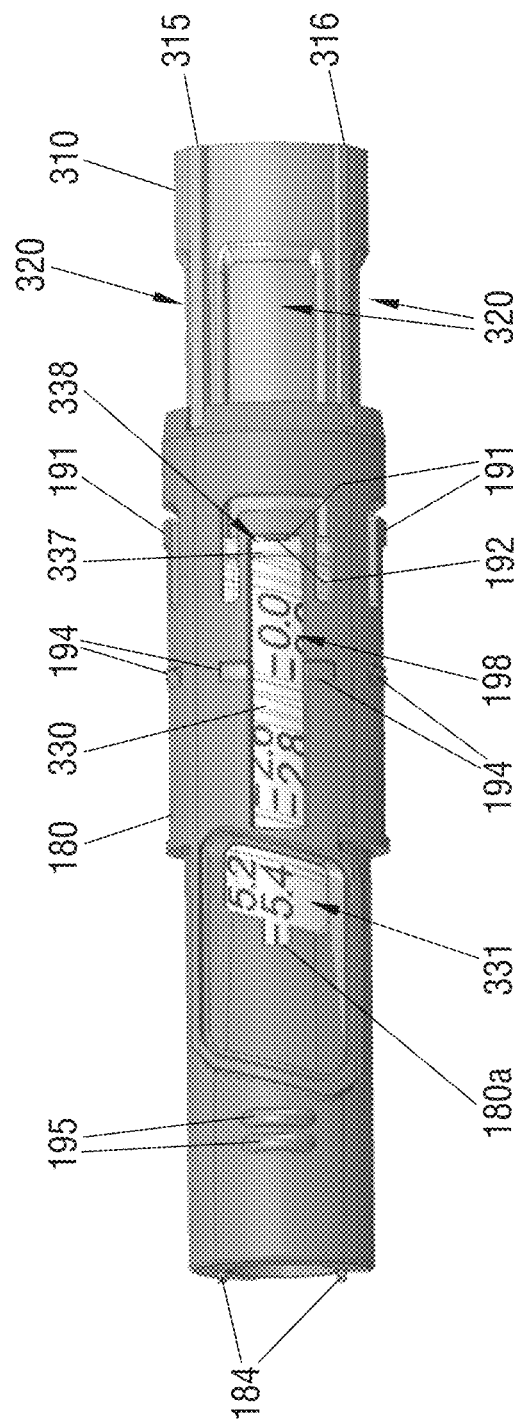
FIG. 23 is a perspective view of the inner housing with the dosing member in a maximum dose position.

FIG. 22 shows a perspective view of the inner housing 180 with the dosing member 330 in the zero-dose position and FIG. 23 shows a perspective view of the inner housing 180 with the dosing member 330 in a maximum dose position.

The dosing member 330 is configured to perform two full rotations about the longitudinal axis 207 when moving from the zero-dose position to the maximum dose position. In the zero-dose position, a minimum dose marker is visible in the window 188a of the inner housing 180 indicating a set dose of 0.0, and in the maximum dose position, a maximum dose marker is visible in the window 188a indicating a set dose of 5.4.

With other embodiments of the drug delivery device 200, the dosing member 330 can be configured to perform less or more than two full rotations about the longitudinal axis 207 when moving from the zero-dose position to the maximum dose position. In particular, the drug delivery device 200 can be configured to perform a non-integer rotation that deviates from a full rotation or an integer multiple of a full rotation. Likewise, the maximum dose marker can indicate any other dose that deviates from a set dose of 5.4, for example a set dose of 1.8 or 3.6.

The inwardly protruding maximum stop features 190 of the inner housing 180 are located inside longitudinal detents 320 of the dose selector member 310. This allows the limiting surfaces 192 to engage with the stopping surface 338 despite the dose selector member 310 surrounding the dosing member 330 in its distal part 333.

The inner housing 180 is both axially and rotationally locked with respect to the outer housing 211. As can be seen from FIG. 22 and FIG. 23, the inner housing 180 comprises protrusions 194 that are circumferentially distributed around the outer surface of the distal part 182 of the inner housing 180. Furthermore, the inner housing 180 comprises radial protrusions 195 that are located on the outer surface of the proximal part 181 of the inner housing 180. With the embodiments shown in FIG. 22 and FIG. 23, two radial protrusions 195 are placed next to each other parallel to the longitudinal axis 207. The two protrusions 195 are both placed at the same circumferential position on the outer surface of the inner housing 180.

Figure 24:
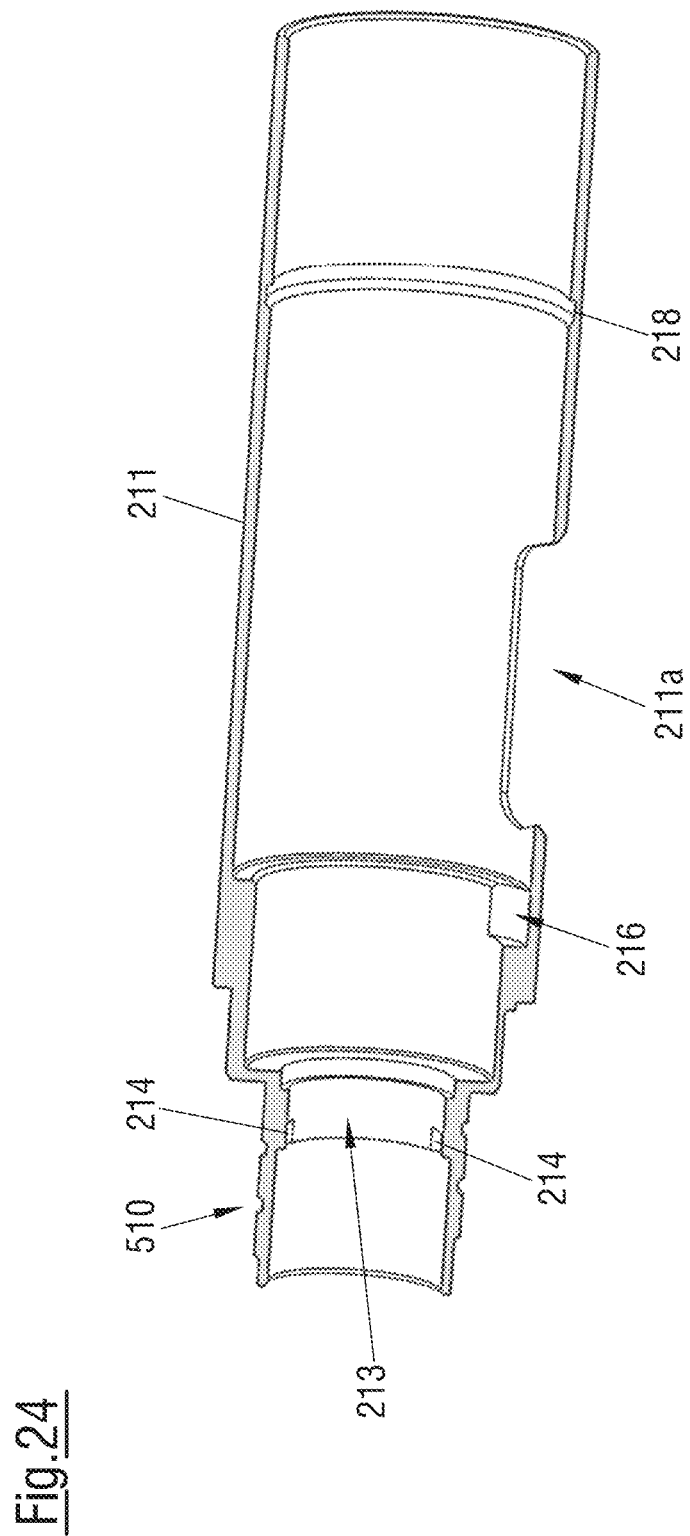
FIG. 24 is a longitudinal partial cross sectional view of an outer housing of the drug delivery device.

As can be seen from FIG. 24, which shows a longitudinal cut through the outer housing 211 of the drug delivery device 200, the outer housing 211 comprises, on its inner surface, a circumferential groove 218, which is located in the distal part of the outer housing 211. Furthermore, the outer housing 211 comprises a detent 216 in a proximal part of its inner surface.

Figure 25:
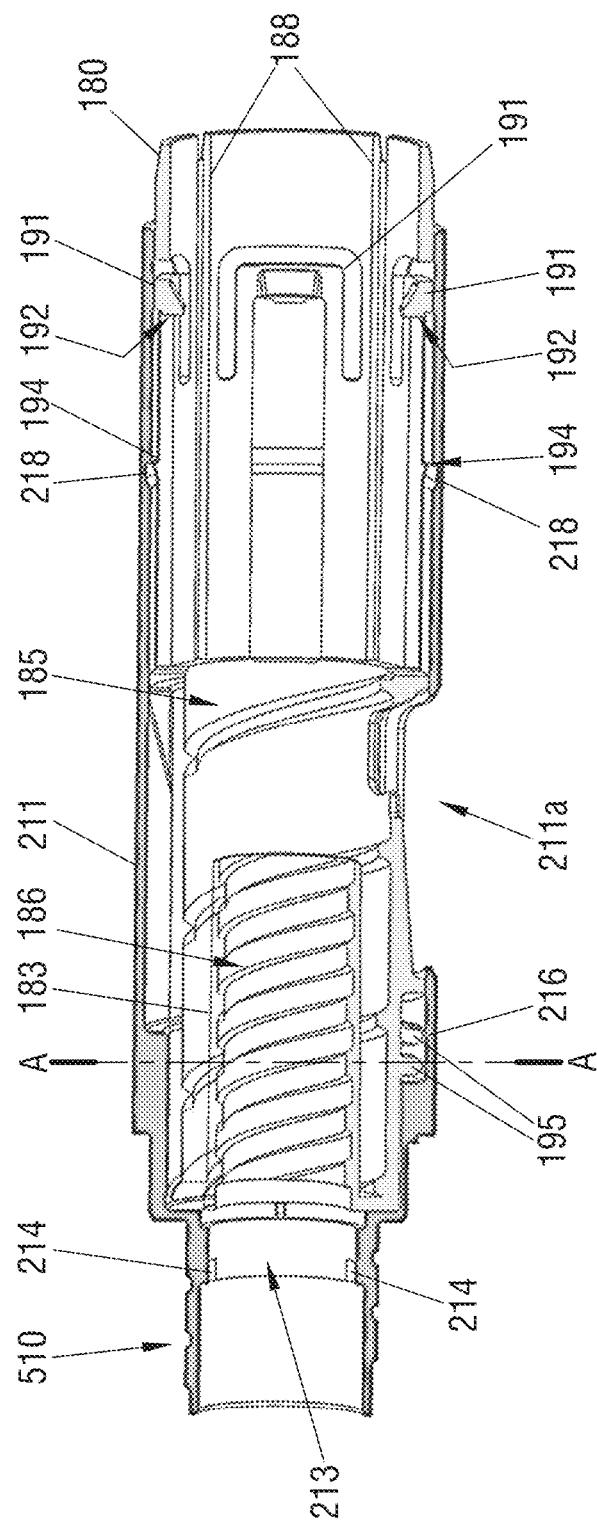
FIG. 25 is a longitudinal cross sectional view of the inner housing mounted within the outer housing of the drug delivery device.

FIG. 25 shows longitudinal cut of the inner housing 180 mounted within the outer housing 211 of the drug delivery device 200. The protrusions 194 in the distal part 182 of the inner housing 180 are configured to prevent axial movement of the inner housing 180 with respect to the outer housing 211 in the distal direction. They snap into the circumferential groove 218 when mounting the inner housing 180 inside the outer housing 211 by inserting the inner housing 180 into the outer housing 211 from its distal end. When pushing the inner housing 180 in the distal direction after full insertion, the protrusions 194 engage with the distal end surface of the circumferential groove 218 and thereby prevent axial movement. In the proximal direction, the inner housing 180 abuts against a step within the inner surface of the outer housing 211, which step is limiting proximal movement of the inner housing.

With other embodiments of the drug delivery device 200, axial movement of the inner housing 180 with respect to the other housing 211 can also be prevented by other means. For example, the outer housing 211 can comprise flexible elements that engage with grooves positioned on the outer surface of the inner housing 180.

Figure 26:
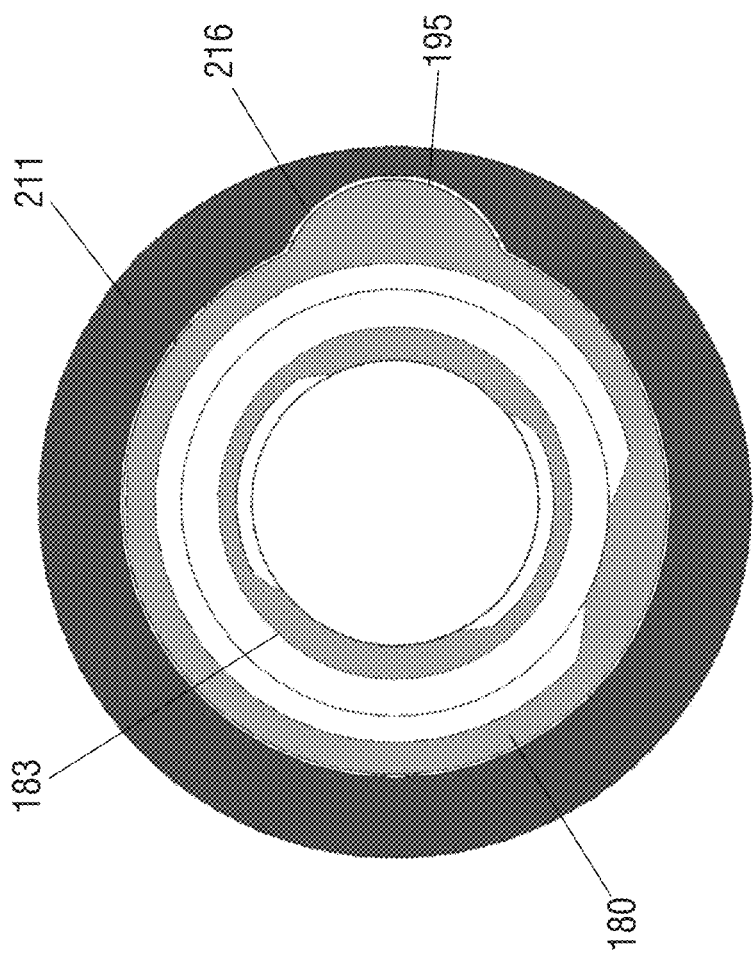
FIG. 26 is a radial cross sectional view of the outer and inner housing of the drug delivery device.

The radial protrusions 195 in the proximal part of the inner housing 180 are configured to prevent rotational movement of the inner housing 180 with respect to the outer housing 211. They engage with the detent 216 in the proximal part of the inner surface of the outer housing 211. This is further illustrated in FIG. 26, which shows a radial cut through the outer and inner housing 211, 180 of the drug delivery device 200 through the line A-A shown in FIG. 25. With other embodiments of the drug delivery device 200, rotational movement of the inner housing 180 with respect to the other housing 211 can also be prevented by other means. For example, the outer housing 211 can comprise protrusions that engage with detents positioned on the outer surface of the inner housing 180.

Upon assembly of the drug delivery device 200, the dose selector member 310 and the dosing member 330 are first assembled to each other and inserted into the inner housing 180. The inner housing 180 is only then inserted into the outer housing 211. After insertion into the outer housing 211, the flexible hooks 191 rest against the inner surface of the outer housing 211 thus preventing outward bending of the flexible hooks 191. This prevents disengagement of the hooks 191 from the maximum dose stop 337 upon setting the maximum dose.

The drug delivery device 200 is configured to deliver a multitude of individual doses from the cartridge 8 attached to the device 200 via the cartridge holder 412. Furthermore, the drug delivery device 200 is configured as a reusable drug delivery device, which allows a user to replace an empty cartridge 8 by a new cartridge 8 after the last dose has been delivered from a given cartridge 8.

Figure 27:
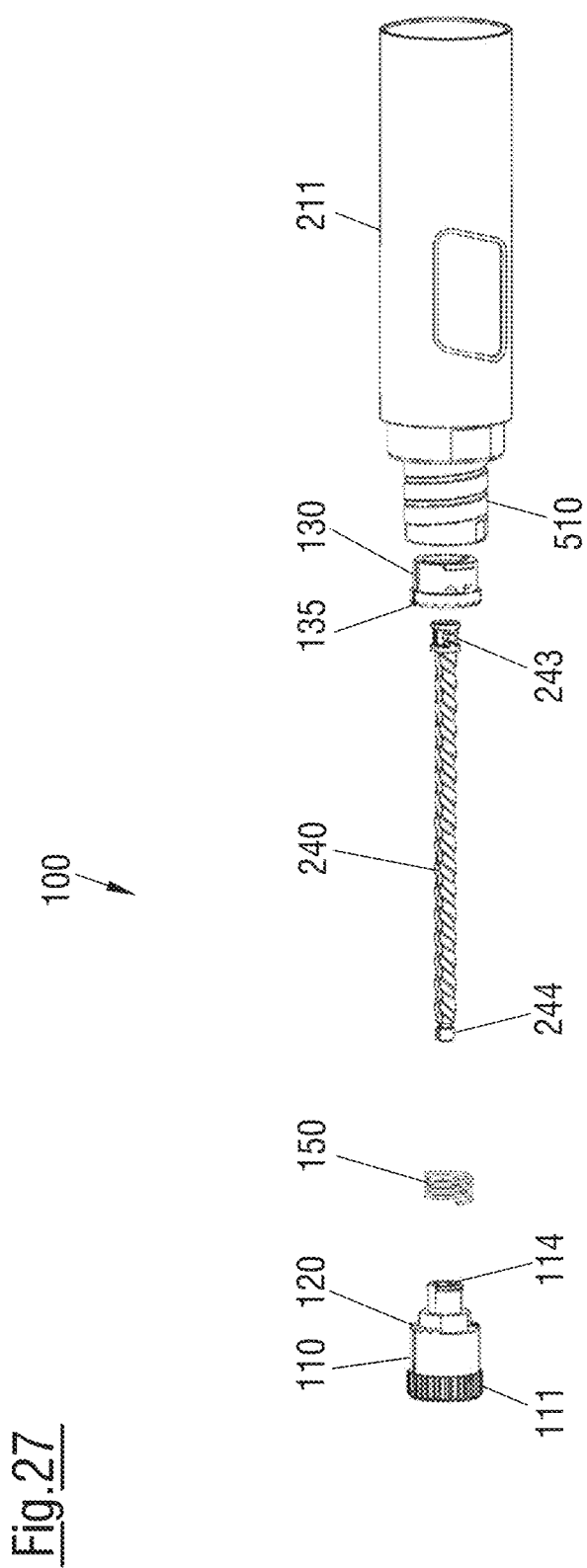
FIG. 27 is an exploded partial view of a resetting mechanism of the drug delivery device.

The resetting mechanism 100, which is shown in an exploded partial view in FIG. 27, thereby allows to move the piston rod 240 back into the housing 210 after delivery of the last dose and disengagement of the cartridge holder 412 from the housing 210.

The resetting element 110 of the resetting mechanism 100, which guides the piston rod 240 in the non-circular opening 114, is mounted to the housing 210, namely the outer housing 211. Connection between the resetting element 110 and the housing 210 is achieved by a coupling part 130, which is both rotationally and axially fixed with respect to the housing 210. The coupling part 130 is configured as an insert received within the housing 210, namely within the outer housing 211.

According to embodiments of the present disclosure, the housing 210 comprises all members that are permanently rotationally and axially fixed with respect to the outer housing 211 during intended use of the drug delivery device 200. As such, the insert 130 can also be considered as being part of the housing 210.

A biasing element 150, which is configured as a compression spring, is mounted between the coupling part 130 and the resetting element 110 and therefore also between the housing 210 and the resetting element 110. The biasing element 150 biases the resetting element 110 in the proximal direction into a proximal position with respect to the housing 210 and the coupling part 130.

Figure 28:
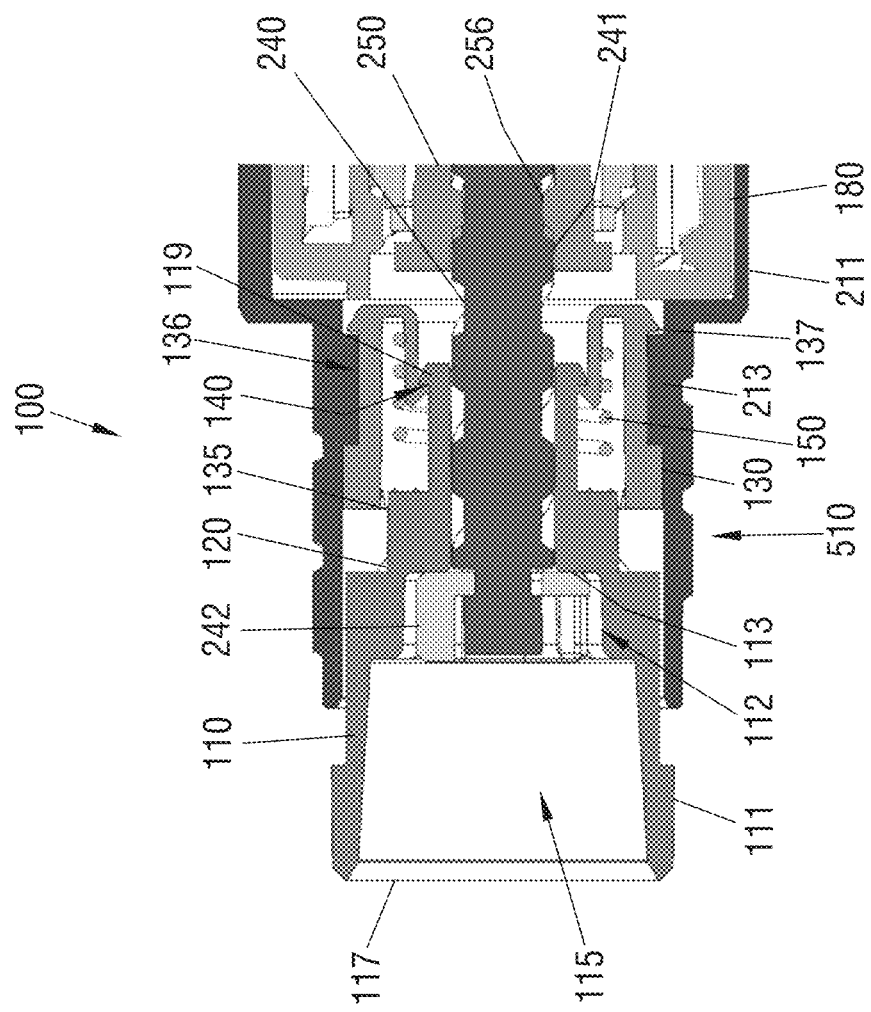
FIG. 28 is a longitudinal cross sectional view of the resetting mechanism of the drug delivery device with a resetting element in a proximal position.

FIG. 28 shows a longitudinal cut through the resetting mechanism 100 of the drug delivery device 200 with the resetting element 110 in the proximal position. In this configuration, the resetting element 110 is rotationally movable with respect to the housing 210. The resetting element 110 comprises a gripping zone 111 at its proximal end, which can be gripped by the user of the device 200 to rotate the resetting element 110. Within the gripping zone 111, the resetting element 110 as a rough outer surface, such as an undulated outer surface.

Due to the rotationally fixed connection between the resetting element 110 and the piston rod 240, the piston rod 240 is forced to rotate together with the resetting element 110 when the user rotates the resetting element 110. Engagement between the thread 241 of the piston rod 240 and the thread 256 of the nut 250 then forces the piston rod 240 to travel into the distal direction back into the housing 210 upon rotating the resetting element 110 in a resetting direction. In this way, the resetting element 110 is configured to move the piston rod 240 back into the housing 210 upon rotation by the user.

After disengagement of the cartridge holder 412 from the housing 210, the piston rod 240 is accessible to a user of the device 200. The connection 354 that axially restrains the driver 350 with respect to the nut 250 serves to prevent unwanted movement of the piston rod 240 that could be caused by the piston rod 240 being directly pushed or pulled by the user without simultaneous rotation of the resetting element 110.

For example, if the user sets a dose while the cartridge holder 412 is detached from the housing 210, the nut 250 and the driver 350 move together in the distal direction. Without the connection 354, the nut 250 would not be prevented from moving proximally again if a user then pulls the piston rod 240 and the user would be able to pull the piston rod 240 out of the housing 210. This could lead to the impression that the device 200 is broken.

With the connection 354, pulling the piston rod 240 out of the housing 210 by the user without simultaneous rotation of the piston rod 240 is prevented. Axial movement of the piston rod 240 without rotation would namely require the nut 250 to move axially. Due to the connection 354 between nut 250 and driver 350 and due to the threaded connection 352 between the driver 350 and the inner housing 180, the driver 350 would also have to move axially and rotate with respect to the housing 210. However, due to the gearing that is caused by the different pitches of the threaded connection 352 between the driver 350 and the inner housing 180 and of the threaded connection 334 between the dosing member 330 and the inner housing 180, the forces that a user is typically able to exert by pulling or pushing the piston rod 240 are not large enough to overcome the resistance required to cause a rotation of the dosing member 330, the clutch member 270 and the dose setting member 290 by directly forcing the driver 350 to rotate. Therefore, the driver 350 and, via the connection 354, also the nut 250 are essentially rotationally and axially locked when the dose setting member 290 is not being actuated.

Figure 30:
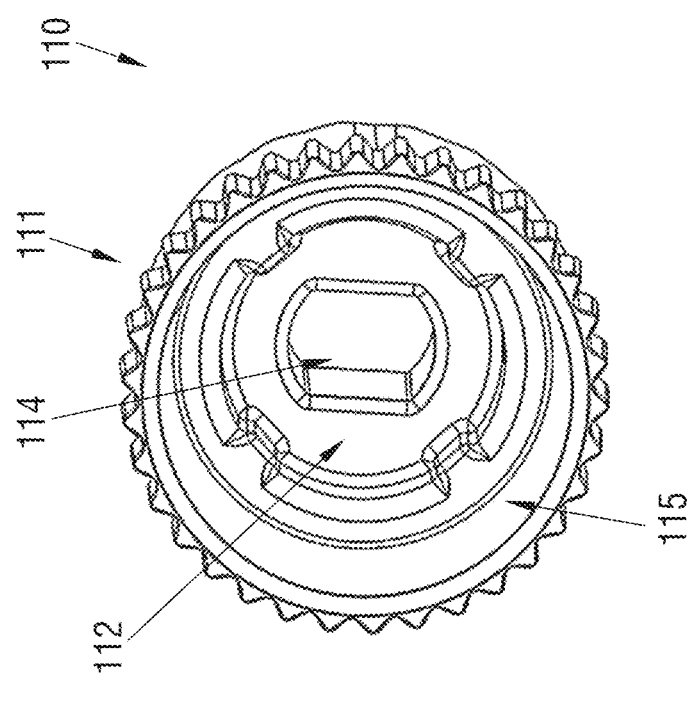
FIG. 30 is a proximal perspective view of the resetting element.
Figure 29:
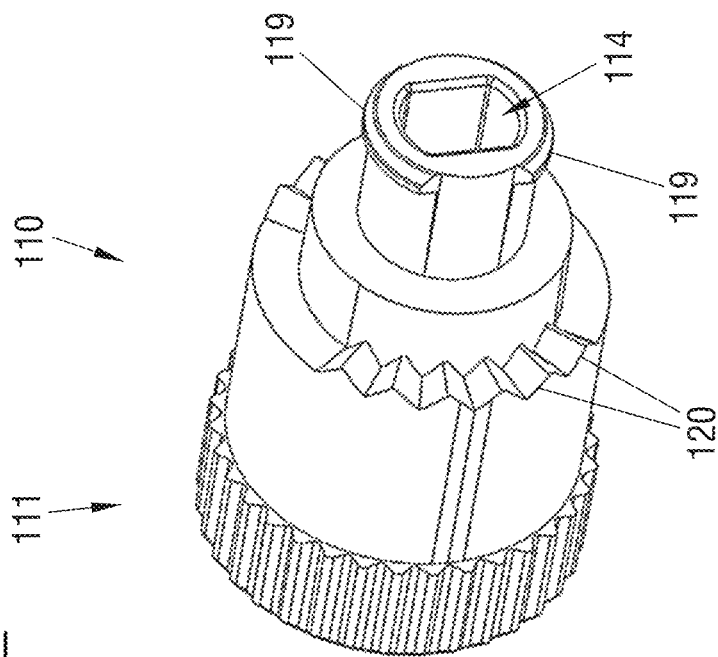
FIG. 29 is a distal perspective view of the resetting element of the resetting mechanism.
Figure 31:
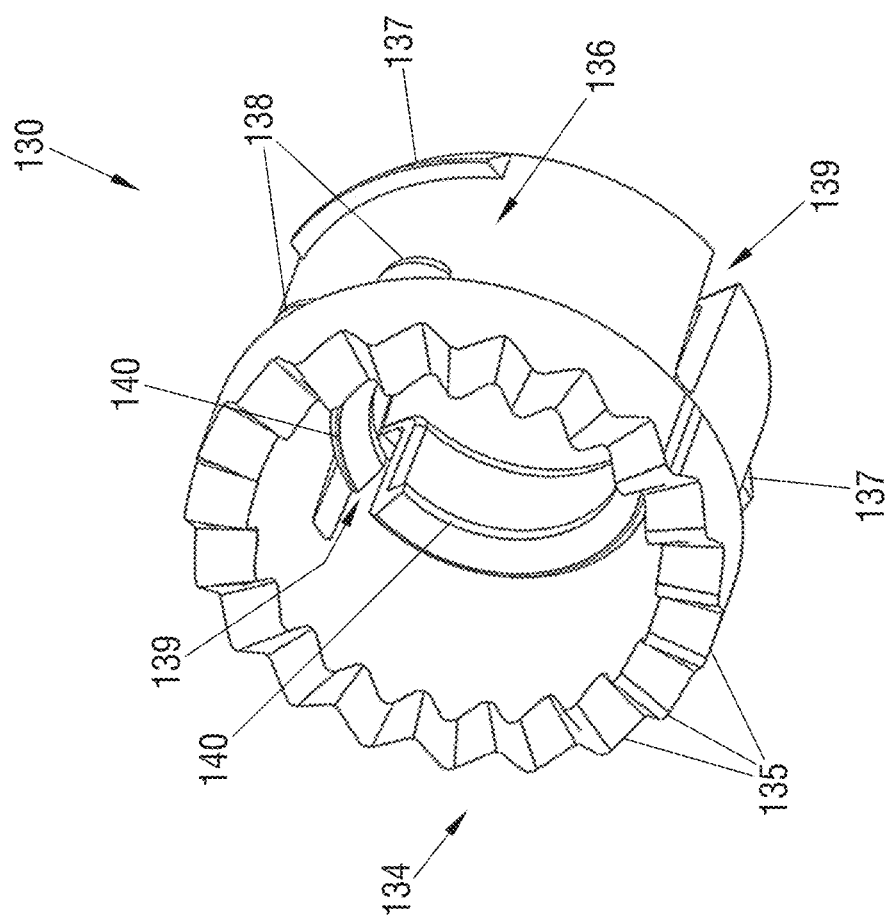
FIG. 31 is a proximal perspective view of a coupling part of the resetting mechanism.

FIG. 29 shows a distal perspective view of the resetting element 110, FIG. 30 shows a proximal perspective view of the resetting element 110 and FIG. 31 shows a proximal perspective view of the coupling part 130 of the resetting mechanism 110.

As can be seen from FIG. 28, a distal part of the resetting element 110 is received within the coupling part 130. In the proximal position shown in FIG. 28, further proximal movement of the resetting element 110 under the action of the biasing member 150 within the coupling part 130 is prevented by the resetting element 110 engaging with the coupling part 130. Thereby, a radial stop 119 located at the distal end of the resetting element 110 engages with a corresponding stop feature 140 on an inner surface of the coupling part 130. With other embodiments, further proximal movement of the resetting element 110 can also be prevented in other ways.

As can also be seen from FIG. 28, the coupling part 130 is axially locked with respect to the housing 210 by an annular notch 136 that is located on the outer surface of the coupling part 130, whereby the annular notch 136 is received in a corresponding collar 213 on an inner surface of the outer housing 211. The notch 136 is distally limited by a locking structure 137 that radially protrudes from the outer surface of the coupling part 130. Upon inserting the coupling part 130 into the outer housing 211 in the distal direction, the locking structure 137 flexes radially inwardly and snaps over the annular collar 213 of the outer housing 211. In this way, the coupling part 130 is axially fixed with respect to the housing 210 by a snap-fit connection. With other embodiments, axial movement between the coupling part 130 and the housing 210 can also be prevented with other means, for example by a notch located on the housing 210 and a collar or protrusion located at the coupling part 130.

To rotationally lock the coupling part 130 with respect to the housing 210, the coupling part 130 comprises protrusions 138 that are located within the notch 136. The protrusions 138 engage with corresponding detents 214 in the annular collar 213. These detents 214 are shown, inter alia, in FIG. 24. With other embodiments, rotation between the coupling part 130 and the housing 210 can also be prevented by other means, for example by protrusions disposed on the housing 210 and corresponding detents provided at the coupling part 130.

The locking structure 137 of the coupling part 130 comprises two portions that are separated by longitudinal slots 139. This allows the portions of the locking structure 137 to radially bend inwardly when mounting the coupling part 130 to the outer housing 211. After mounting the coupling part 130 and after mounting the inner housing 180 to the outer housing 211, the portions of the locking structure 137 are prevented from bending inwardly by engagement with the inner housing 180. When assembling the device 200, the coupling part 130 and the resetting element 110 are first snapped to the outer housing 211 and only then the inner housing 180 is inserted into the outer housing 211.

Figure 32:
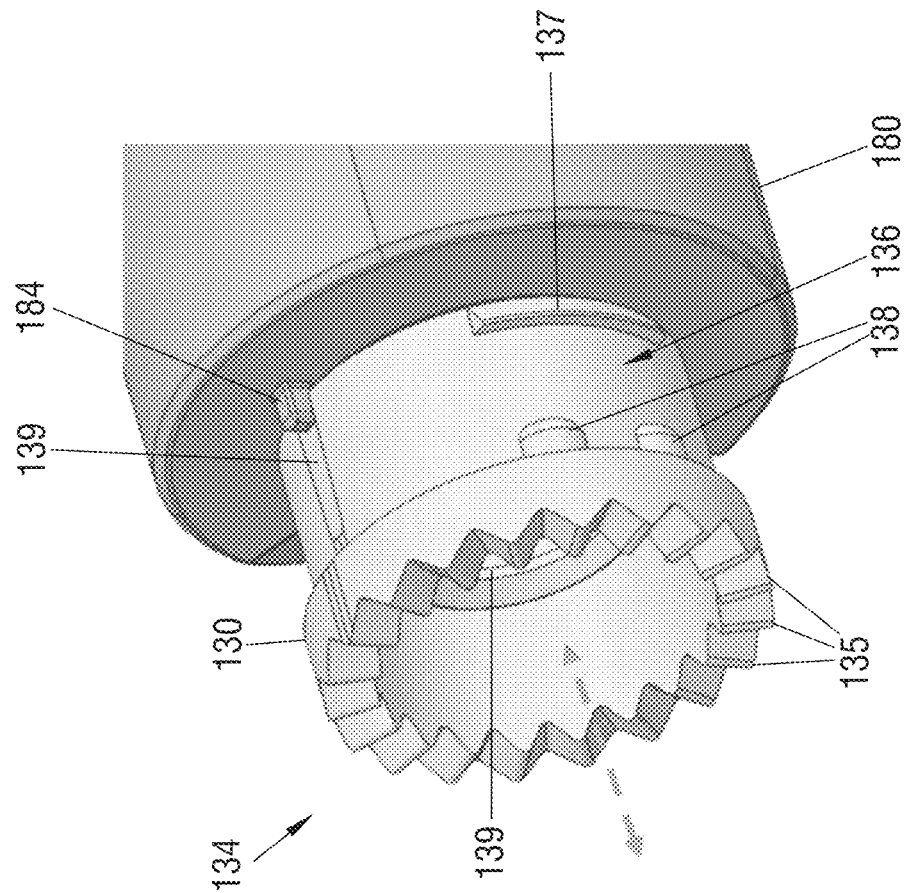
FIG. 32 is a perspective view of the coupling part and the inner housing.

FIG. 32 shows a perspective view of the coupling part 130 and the inner housing 180. The inner housing 180 comprises at its front surface two longitudinally protruding tappets 184, which are also visible, for example, in FIG. 23. The tappets 184 are received within the longitudinal slots 139 and thereby block the portions of the locking structure 137 from radially bending inwardly.

Figure 33:
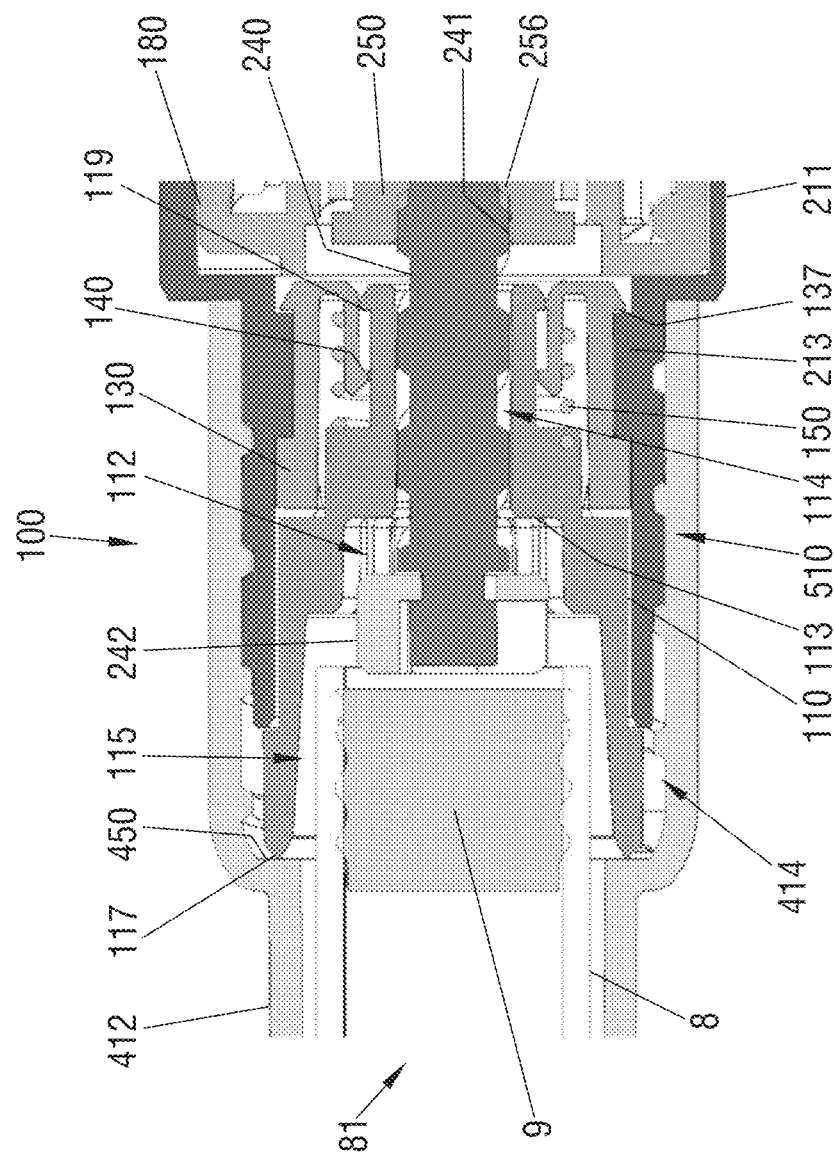
FIG. 33 is a longitudinal cross sectional view of the resetting mechanism with the dispensing unit attached to the drug delivery device and the resetting element located in a distal position.

FIG. 33 shows a longitudinal cut through the resetting mechanism 100 with the dispensing unit 410 attached the drug delivery device 200. When attaching the dispensing unit 410, the inner thread of the connection device 414 of the dispensing unit 410 is screwed onto the outer thread of the connection means 510 of the outer housing 211 until the distal end of the cartridge holder 412 rests against a step formed on the outer surface of the outer housing 211.

During mounting of the dispensing unit 410, the resetting element 110 is moved into the distal direction into its distal position to rotationally lock the resetting element 110 with respect to the housing 210. When being in its distal position, engagement features 120 of the resetting element 110 engage with corresponding engagement features 135 of the coupling part 130 and thereby rotationally lock the resetting element 110 with respect to the coupling part 130 and the housing 210.

The engagement feature 120 of the resetting element 110 are configured as distally facing teeth. The engagement features 135 of the coupling part 130 are located at a coupling site, which is formed by a front surface of the coupling part 130. The engagement features 135 are configured as proximally facing teeth that match between the distally facing teeth of the engagement feature 120 of the resetting element 110.

In the embodiment shown in FIG. 27 and FIG. 33 the engagement features 120, 135 are configured as symmetric teeth that have circumferential side surfaces that have the same slope. With other embodiments, the teeth of the engagement features 120, 135 can also be configured as asymmetric teeth. For example, the asymmetric teeth can have circumferential side surfaces with different slopes. Thereby, one side surface of the individual teeth can be orientated, for example, parallel to the longitudinal axis 207 and the respective other side surface can be inclined with respect to the longitudinal axis 207. Such asymmetric teeth can, for example, provide a saw-tooth profile.

With asymmetric engagement features 120, 135, side surfaces of the individual engagement features 120, 135 having a steeper slope than the respective other side surfaces can be configured to press against each other when the resetting element 110 is rotated in a circumferential direction that would screw the piston rod 240 back into the housing 210. This efficiently prevents a counter-rotation of the piston rod 240 with respect to the nut 250 during dose delivery or when overturning the dose setting member 290 and the nut 250 after the thread 256 of the nut 250 has engaged the stop feature 243 of the piston rod 240 upon increasing the dose during dose setting.

As can be seen from FIG. 33, the cartridge holder 412 of the dispensing unit 410 directly engages with the resetting element 110 to push the resetting element 110 into the distal direction upon mounting the dispensing unit 410 onto the housing 210. Thereby, a proximally facing contact structure 117 of the resetting element 110 rests against a distally facing contact feature 450 of the cartridge holder 412. The proximally facing contact structure 117 is exemplarily configured as a proximal circumferential edge of the resetting member 110. The distally facing contact feature 450 is exemplarily provided as a distally facing annular surface located at an inwardly protruding step of the cartridge holder 412.

The proximal position of the resetting element 110 is a resetting position of the resetting element 110 and the distal position of the resetting element 110 is a locking position of the resetting element 110. A locking distance between the resetting position and the locking position may, for example, be smaller than 2 mm, 1.5 mm, 1.25 mm, 1.1 mm or 1 mm and/or larger than 0.5 mm, 0.7 mm or 0.8 mm. It may, for example, amount to 0.8 mm, 0.9 mm, 1.0 mm or 1.1 mm.

With the cartridge holder 412 mounted to the housing 210, the cartridge 8 does not contact the resetting element 110. Therefore, the resetting element 110 is moved in the distal direction solely by its contact with the cartridge holder 412. The distal end of the cartridge 8 is received inside a cartridge cavity 115 of the resetting element 110, the cartridge cavity 115 being accessible from the proximal side of the resetting element 110.

The direct engagement between the cartridge holder 412 and the resetting element 110 allows, compared to an engagement between the cartridge 8 and the resetting element 110, to configure the engagement features 120, 135 with tighter axial tolerances and a smaller axial height. Typically, the individual cartridges 8 are made from glass and have larger variation in their longitudinal extent then individual cartridge holders 412, which are typically made from a plastic material. Therefore, the engagement features 120, 135 would have to have a comparably large axial height to provide a secure rotational locking between the resetting element 110 and the coupling part 130 irrespective of possible variations in the length of individual cartridges 8 due to manufacturing tolerances.

When being fully retracted into the housing 210, the plunger disc 242 of the piston rod 240 is located within a reception area 112 of the resetting element 110. The reception area 112 is configured as a further cavity that is accessible from the proximal side of the resetting element 110. Furthermore, the reception area 112 is located at and accessible from the distal end of the cartridge cavity 115. In its fully retracted position, the plunger disc 242 of the piston rod 240 rests against an inner surface 113 of the reception area 112. This inner surface 113 forms the distal end surface of the reception area 112 and surrounds the opening 114 of the resetting element 110 that guides the piston rod 240.

Figure 34:
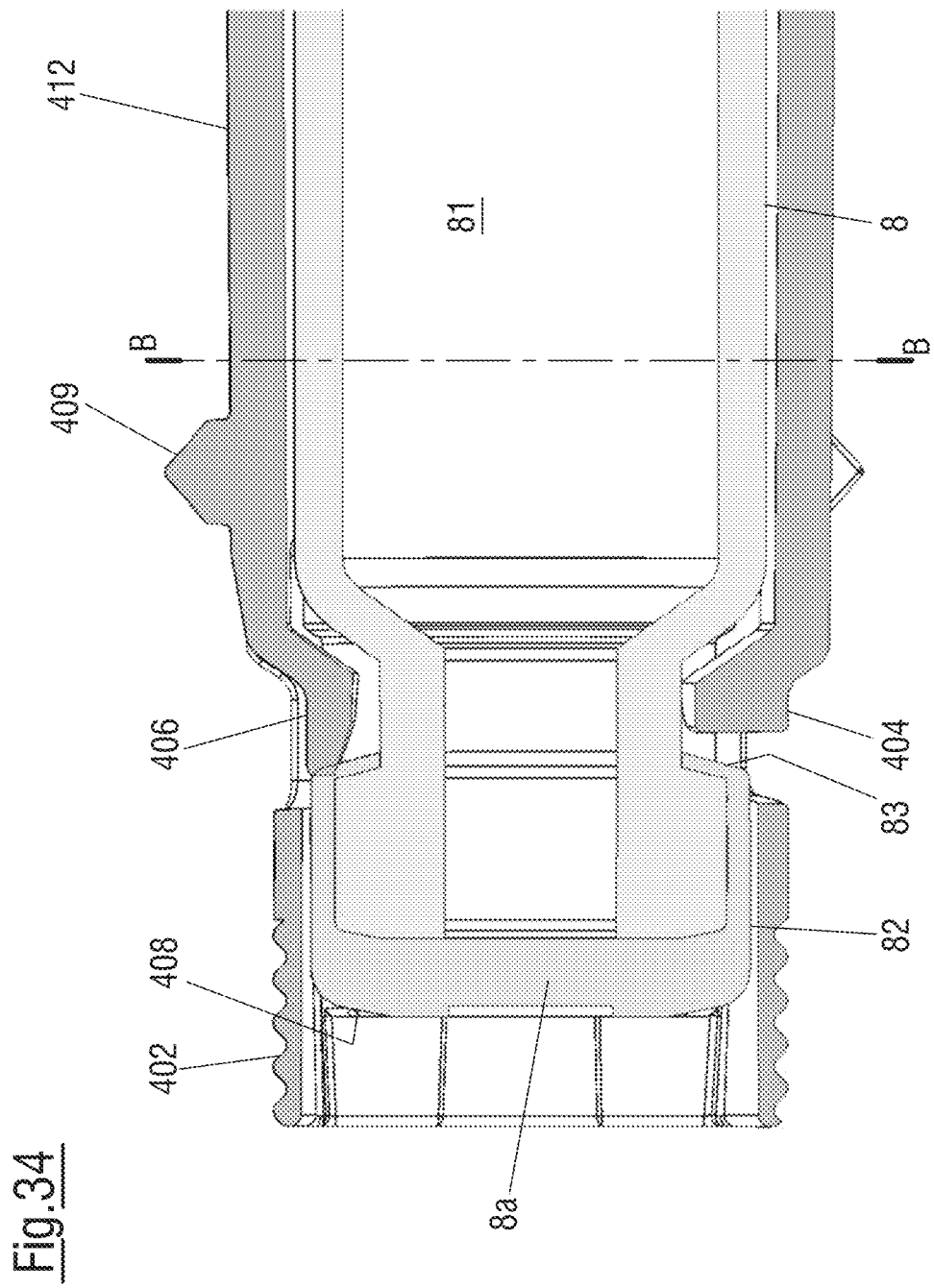
FIG. 34 is a longitudinal cross sectional view of a proximal end of a cartridge holder attachable to the drug delivery device.
Figure 35:
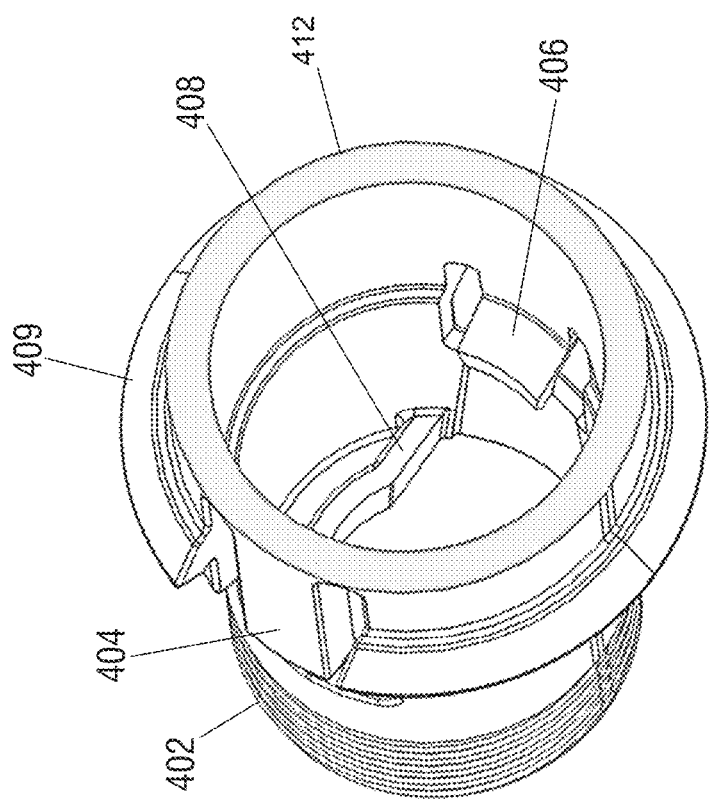
FIG. 35 is a perspective distal view of a radial cut through a proximal part of the cartridge holder.

FIG. 34 shows a longitudinal cut through a proximal end of the cartridge holder 412 attachable to the drug delivery device 200 with the cartridge 8 inserted into the cartridge holder 412. FIG. 35 shows a perspective distal view of a radial cut through the proximal part of the cartridge holder 412. Inside the cartridge holder 412, the cartridge 8 is pushed against the stop 408 by a push element 406. The push element 406 engages with the distal surface 83 of the annular rim 82 of the cartridge 8. It is configured as a flexible member that snaps over the annular rim 82 when the cartridge 8 is inserted into the cartridge holder 412. The push feature 406 is configured as an integral part of the cartridge holder 412.

The proximal part of the cartridge holder 412 furthermore comprises an annular ridge 409 that radially extends from the outer surface of the cartridge holder 412. The annular ridge 409 is configured to be engaged by a locking arm of the cap 209, which is disposed on an inner surface of the cap 209. Engagement between the locking arm and the annular ridge 409 releasably locks the cap 209 to the drug delivery device 200 after attachment.

According to embodiments of the present disclosure, the drug delivery device 200 can be part of a set of several drug delivery devices and the dispensing unit 410 can be part of a set of several dispensing units, whereby each drug delivery device comprises connection means that only allow attachment of a dedicated dispensing unit and prevents attachment of all other dispensing units of the set and vice versa. The connection devices are thereby configured as keyed connectors, which provide a one-to-one assignment between the individual dispensing units and the individual drug delivery devices.

The set of drug delivery devices can comprise further variants of the drug delivery device 200 that have at least one mutual member that is identical among the drug delivery device 200 and the further variants. The set can also comprise different types of drug delivery devices that do not share such a mutual member with the drug delivery device 200.

FIGS. 36A-36C and FIGS. 37A-37C show a set of three drug delivery devices and a set of three corresponding dispensing units according to the present disclosure. Each drug delivery device is connected to its corresponding dispensing unit by a keyed connection that prevents the respective drug delivery device from connecting to the other dispensing units and which, vice versa, prevents the corresponding dispensing unit from connecting to the other drug delivery devices.

Figure 36A:
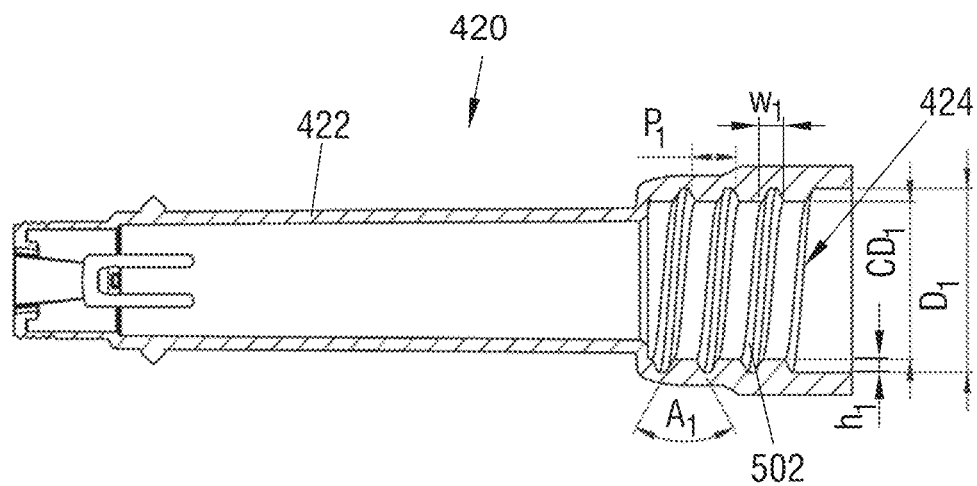
FIGS. 36A-36C illustrate a longitudinal cross sectional view of a first dispensing unit attachable to a first drug delivery device, a longitudinal cross sectional view of a second dispensing unit attachable to a second drug delivery device, and a longitudinal cross sectional view of a third dispensing unit attachable to a third drug delivery device.
Figure 36B:
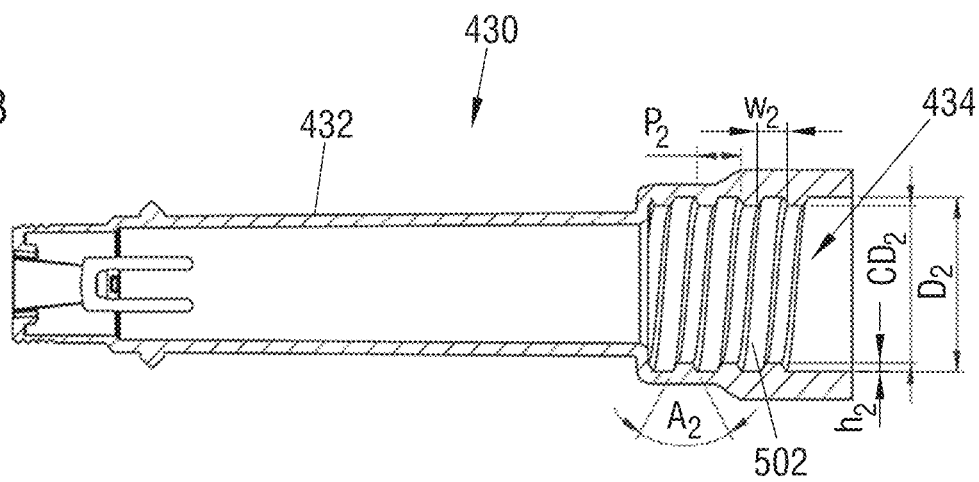
Figure 36C:
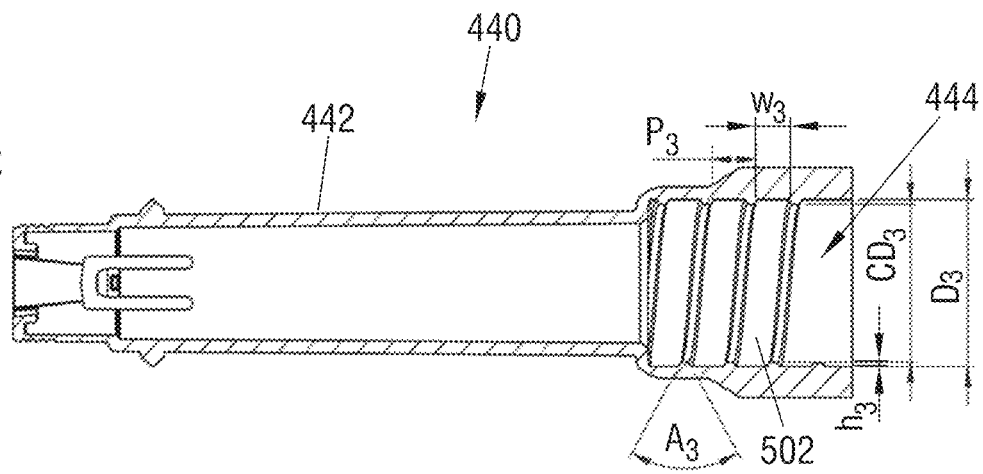
Figure 37A:
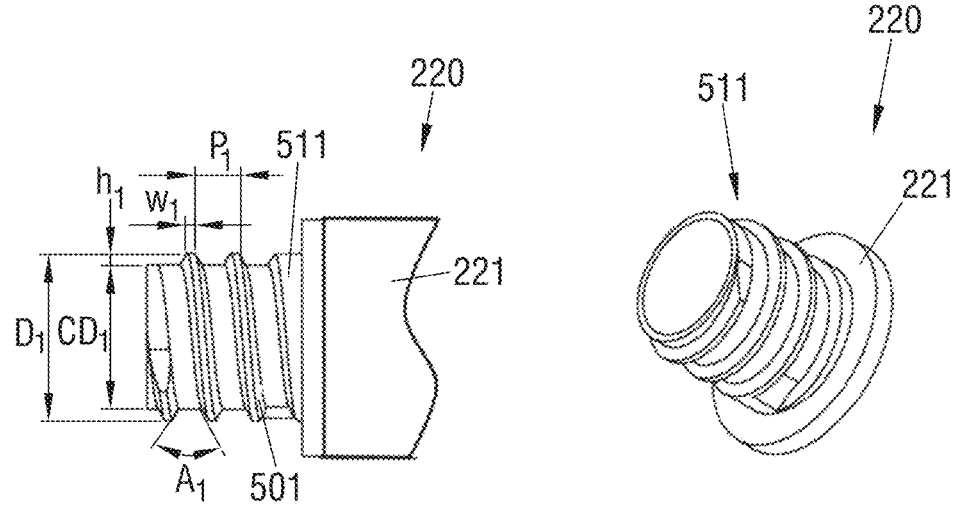
FIGS. 37A-37C illustrate a longitudinal view of a first connection device of the first drug delivery device and a perspective view of the first connection device, a longitudinal view of a second connection device of the second drug delivery device and a perspective view of the second connection device, and a longitudinal view of a third connection device of the third drug delivery device and a perspective view of the third connection device.
Figure 37B:
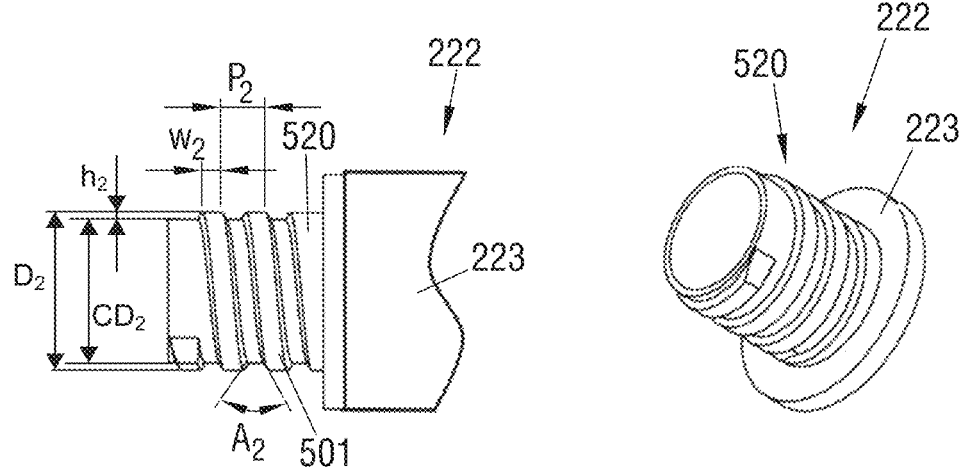
Figure 37C:
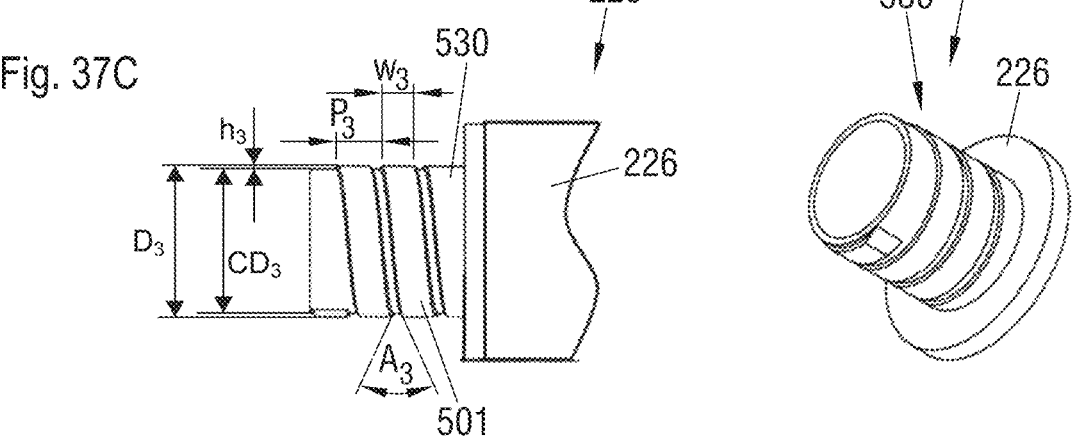

Thereby, FIGS. 36A-36C a longitudinal cut through a first dispensing unit 420 attachable to a first housing 221 of a first drug delivery device 220 via a first connection device or means 424 of a first cartridge holder 422, a longitudinal cross sectional view of a second dispensing unit 430 attachable to a second housing 223 of a second drug delivery device 222 via a second connection device or means 434 of a second cartridge holder 432 of the second dispensing unit 430 and a longitudinal cross sectional view of a third dispensing unit 440 attachable to a third housing 226 of a third drug delivery device 225 via a third connection device means 444 of a third cartridge holder 442 of the third dispensing unit 440. FIGS. 37A-37C show side views and perspective views of the first connection device 511 of the first housing 221 of the first drug delivery device 220, of the second connection device 520 of the second housing 223 of the second drug delivery device 222 and of the third connection device 530 of the third housing 226 of the third drug delivery device 225.

The connection devices 424, 434, 444 of the cartridge holders 422, 432, 442 and the corresponding connection devices 511, 520, 530 of the drug delivery devices 220, 222, 225 form keyed connectors according to embodiments of the present disclosure. Thereby, the connection devices 424, 434, 444 are of the same type and the connection devices 511, 520, 530 are also of the same type.

The individual connection devices 424, 434, 444 of the cartridge holders 422, 432, 442 each form female parts of the connections and the individual connection devices 511, 520, 530 of the drug delivery devices 220, 222, 225 form corresponding male parts. All connection devices 424, 434, 444, 511, 520, 530 are configured as threads, whereby the connection devices 424, 434, 444 of the cartridge holders 422, 432, 442 form inner threads and the connection devices 511, 520, 530 of the drug delivery devices 220, 222, 225 form outer threads.

The geometries of the threads 424, 434, 444, 511, 520, 530 are defined by several thread dimensions. The thread dimensions comprise a core diameter or minor diameter that specifies the minimum inner diameter of the female part of the connections, an outer diameter or major diameter that specifies the maximum inner diameter of the female part of the connections, a pitch that specifies a distance between adjacent ridges 501 or valleys 502 of the threads, a width of the ridges 501 disposed on the male part of the threads, which corresponds to a width of the valleys 502 disposed on the female part of the threads and an opening angle between sidewalls of adjacent ridges 501 of the male parts. A height of the ridges 501 of the male parts and a corresponding height of the valleys 502 of the female parts is given by the difference between the outer diameter and the core diameter.

Unless stated otherwise, the term "ridges" used in the present disclosure always refers to the ridges 501 of the male thread of a given threaded connection, irrespective of whether the part being described actually comprises a male thread or a female thread.

Keying is achieved by at least one of the thread dimensions, such as at least one of the core diameter, the outer diameter, the pitch, the width of the ridges 501 and the opening angle, being mutually different among the individual pairs of corresponding connection means 424, 434, 444, 511, 520, 530 of the cartridge holders 422, 432, 442 and drug delivery devices 220, 222, 225.

With the embodiments shown in FIGS. 36A-36C and FIGS. 37A-37C, the only thread dimensions that differ among the individual dispensing units 420, 430, 440 and therefore also among the individual drug delivery devices 220, 222, 225 are the width and the height of the individual ridges 501 of the male parts and the corresponding widths and heights of the valleys 502 of the female parts. Thereby, the ridges 501 of the first connection device 511 have a first width $w_1$, the ridges 501 of the second connection device 520 have a second width $w_2$, and the ridges 501 of the third connection device 530 have a third width $w_3$. The first width $w_1$ is smaller than the second width $w_2$, and the second width $w_2$ is smaller than the third width $w_3$. Exemplarily, the second width $w_2$ is twice the first width $w_1$ and the third width $w_3$ is three times the first width $w_1$.

Furthermore, the ridges 501 of the first connection device 511 have a first height $h_1$, the ridges 501 of the second connection device 520 have a second height $h_2$, and the ridges 501 of the third connection device 530 have a third height $h_3$. The first height $h_1$ is larger than the second height $h_2$, and the second height $h_2$ is larger than the third height $h_3$. Thereby, the second height $h_2$ is twice the third height $h_3$ and the first height $h_1$ is three times the third height $h_3$.

The aforementioned differences in the heights $h_1$, $h_2$, $h_3$, combined with the aforementioned differences in the widths $w_1$, $w_2$, $w_3$ reliably prevent mounting of the individual dispensing units 420, 430, 440 to other than their corresponding drug delivery device 220, 222, 225 with the matching connection devices 511, 520, 530.

The different heights $h_1$, $h_2$, $h_3$ result from different outer diameters with a first outer diameter $D_1$ of the first connection devices 424, 511 being larger than a second outer diameter $D_2$ of the second connection devices 434, 520 and the second outer diameter $D_2$ of the second connection devices 434, 520 being larger than a third outer diameter $D_3$ of the third connection devices 444, 530. The first connection devices 424, 511 have a first core diameter $CD_1$, the second connection means 434, 520 have a second core diameter $CD_2$, and the third connection devices 444, 530 have a third core diameter $CD_3$ and all core diameters $CD_1$, $CD_2$, $CD_3$ are equal.

With other embodiments, the different heights $h_1$, $h_2$, $h_3$ can also result from differing core diameters $CD_1$, $CD_2$, $CD_3$ and, optionally, also differing outer diameters $D_1$, $D_2$, $D_3$. According to still another embodiment, the core diameters $CD_1$, $CD_2$, $CD_3$ can be chosen to be mutually identical and also the outer diameters $D_1$, $D_2$, $D_3$ can be chosen to be mutually identical for all connections such that all devices 220, 222, 225 comprise threads 511, 520, 530 with ridges 501 of the same height.

With the embodiments shown in FIGS. 36A-36C and FIGS. 37A-37C, a first pitch $P_1$ of the first connection devices 424, 511, a second pitch $P_2$ of the second connection devices 434, 520 and a third pitch $P_3$ of the third connection devices 444, 530 are the same. Furthermore, a first angle $A_1$ of the first connection means 424, 511, a second angle $A_2$ of the second connection means 434, 520 and a third angle $A_3$ of the third connection means 444, 530 are also the same.

With the exemplary embodiments shown in FIGS. 36A-36C and FIGS. 37A-37C, the individual thread dimensions can be the following: $CD_1=CD_2=CD_3=12.60$ mm, $D_1=14.70$ mm, $D_2=14.00$ mm, $D_3=13.30$ mm, $h_1=2.10$ mm, $h_2=1.40$ mm, $h_3=0.70$ mm, $w_1=0.65$ mm, $w_2=1.30$ mm, $w_3=1.95$ mm, $A_1=A_2=A_3=60°$. The pitches of the individual threads can thereby all amount to $P_1=P_2=P_3=3.80$ mm.

The thread dimensions can also be the following: $CD_1=CD_2=CD_3=12.60$ mm, $D_1=14.70$ mm, $D_2=14.00$ mm, $D_3=13.30$ mm, $h_1=1.05$ mm, $h_2=0.70$ mm, $h_3=0.35$ mm, $w_1=0.65$ mm, $w_2=1.30$ mm, $w_3=1.95$ mm, $A_1=A_2=A_3=60°$. The pitches of the individual threads can all amount to $P_1=P_2=P_3=3.80$ mm.

Alternatively, the aforementioned dimensions of the width of the ridges of the male threads can apply to the widths g of the valleys of the male threads instead of to the width w of the ridges of the male threads. The widths g of the valleys of the individual male threads can thereby be defined as the bottom sections of the grooves of the male threads that are located at the core diameter and that extend between the angled side surfaces that delimit the ridges of the male thread, as depicted in FIGS. 58 and 59.

Figure 58A:
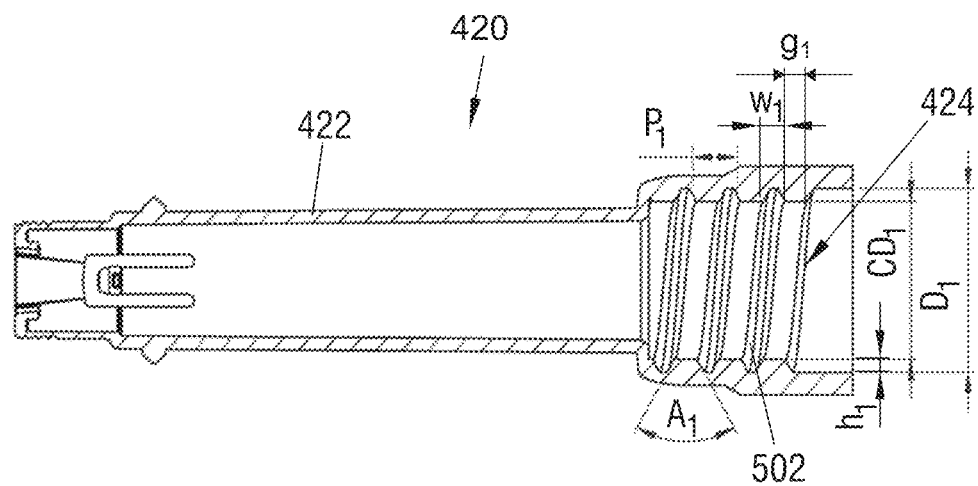
FIGS. 58A-58C illustrate longitudinal cross sectional views of the first, second and third dispensing unit showing additional dimensions.
Figure 58B:
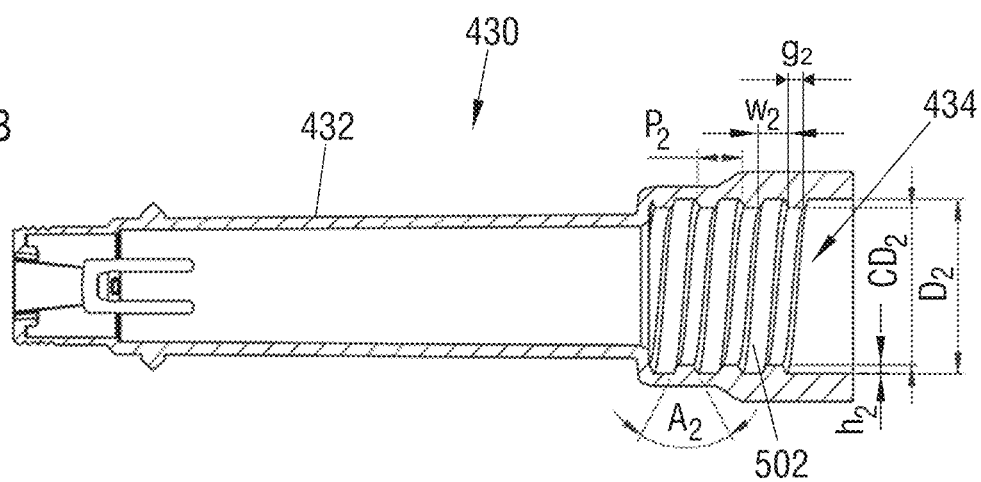
Figure 58C:
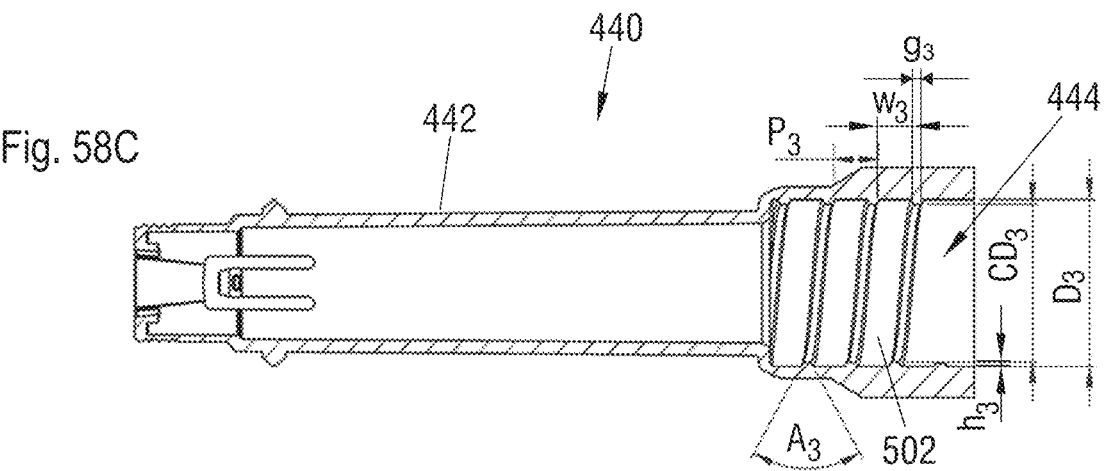
Figure 59A:
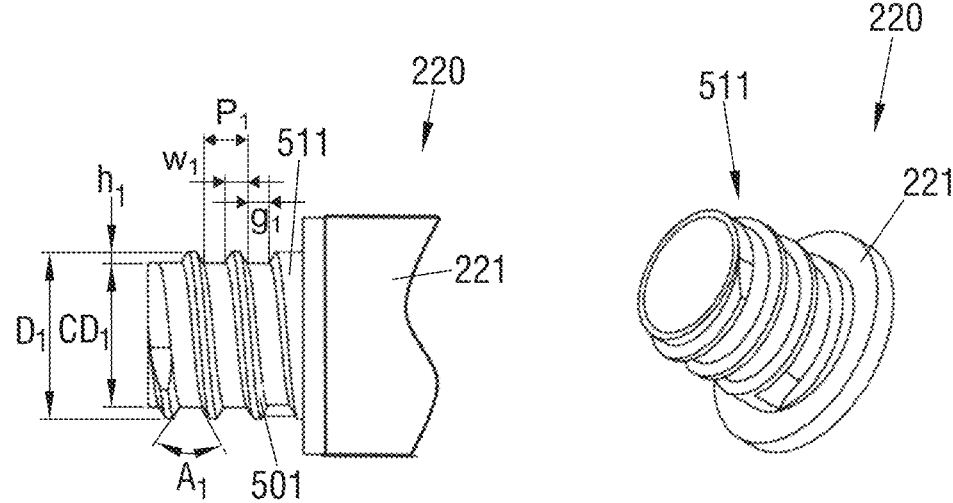
FIGS. 59A-59C illustrate longitudinal cross sectional views of the first, second and third connections devices of the first, second and third drug delivery device showing additional dimensions.
Figure 59B:
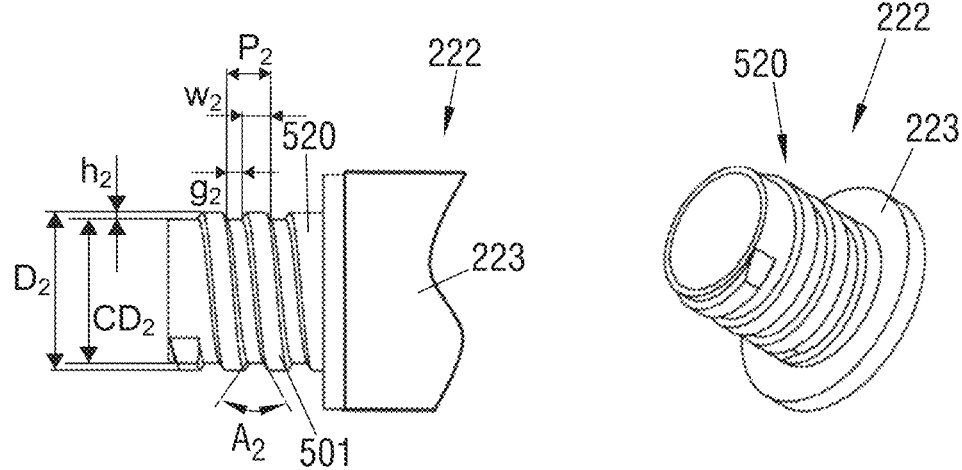
Figure 59C:
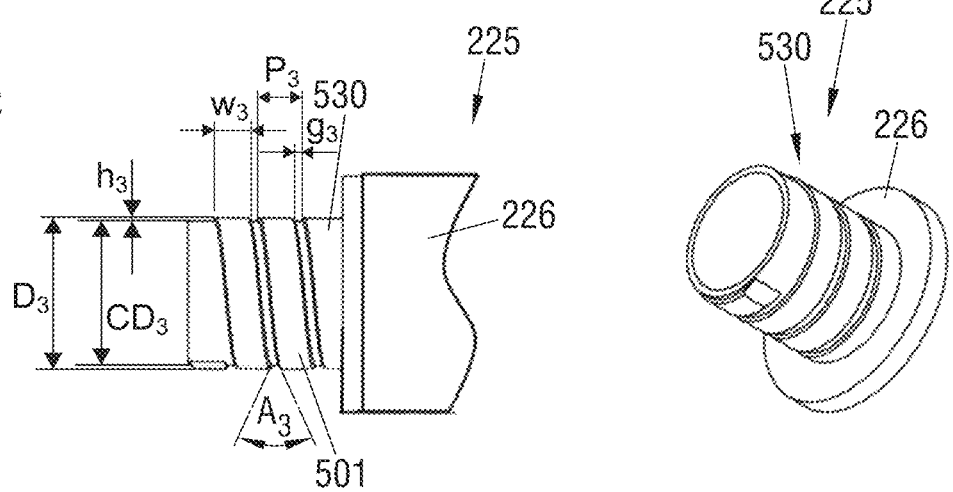

The thread dimensions can then be the following: $CD_1=CD_2=CD_3=12.60$ mm, $D_1=14.70$ mm, $D_2=14.00$ mm, $D_3=13.30$ mm, $h_1=1.05$ mm, $h_2=0.70$ mm, $h_3=0.35$ mm, $g_1=1.95$ mm, $g_2=1.30$ mm, $g_3=0.65$ mm, $A_1=A_2=A_3=60°$ and $P_1=P_2=P_3=3.80$ mm. With this embodiment, the widths w of the ridges of the male threads can amount to: $w_1=1.84$ mm, $w_2=2.50$ mm, $w_3=3.15$ mm. The widths w of the ridges are thereby defined as the widths including the top surfaces that define the outer diameter D and both angled side surfaces that connect the individual top surfaces to neighbouring valleys. Therefore, the widths w amount to $w=P-g$. These dimensions are shown in FIGS. 58A-58C, which shows the dispensing units 420, 430, 440, and in FIGS. 59A-59C, which shows the corresponding connection devices 511, 520, 530 of the dispensing units 220, 222, 225.

In general, among a set of N drug delivery devices 200, the N-th device can have a thread with ridges that have a width that is N-times the width of the ridges of the thread of the first device and the first device can have a thread with ridges that have a height that is N-times the height of the ridges of the N-th device. The m-th device (with $1 \leq m \leq N$) can then have a thread that has ridges with a width that is m-times the width of the ridges of the thread of the first device and with a height that is $(N-m+1)$-times the height of the ridges of the thread of the N-th device.

Alternatively, the aforementioned relation can analogously apply to the widths g of the valleys of the male threads instead of the widths w of the ridges of the male threads. Thereby, the first device can have a thread with valleys that have a width g that is N-times the width g of the valleys of the thread of the N-th device and the first device can have a thread with ridges that have a height that is N-times the height of the ridges of the N-th device. The m-th device (with $1 \leq m \leq N$) can then have a thread that has valleys with a width g that is $(N-m+1)$-times the width g of the valleys of the thread of the N-th device and with a height that is $(N-m+1)$-times the height of the ridges of the thread of the N-th device.

In one embodiment, the first, second and third drug delivery device 220, 222, 225 each are a variant of the drug delivery device 200 disclosed in connection with FIG. 1 to FIG. 35. As far as no differences are described or apparent from the Figures, the first, second and third drug delivery device 220, 222, 225 are then configured as it is disclosed in connection with the drug delivery device 200 and vice versa. Furthermore, the first, second and third dispensing unit 420, 430, 440 each are a variant of the dispensing unit 410 disclosed in connection with FIG. 1 to FIG. 35. As far as no differences are described or apparent from the Figures, the first, second and third dispensing unit 420, 430, 440 are then configured as it is disclosed in connection with the dispensing unit 410 and vice versa.

The second drug delivery device 222 and the first drug delivery device 220 share at least one mutual member that is identical among the first and second drug delivery device 220, 222 and the third drug delivery device 225 and the first drug delivery device 220 share at least one further mutual member that is identical among the first and third drug delivery device 220, 225. Thereby, the mutual member and the further mutual member are identical. With other embodiments, the mutual member and the further mutual member can also be different. Mutual members are thereby both mechanically identical, that is identical in shape, and identical in their appearance, such as in their color and printing.

The second drug delivery device 222 and the first drug delivery device 220 each comprise at least one distinguishing member that is different among the first and second drug delivery device 220, 222 and the third drug delivery device 225 and the first drug delivery device 220 each comprise at least one further distinguishing member that is different among the first and third drug delivery device 220, 225. Thereby, the distinguishing member and the further distinguishing member are the same functional member and therefore perform the same function during use of the dosing mechanism. With other embodiments, the mutual member and the further mutual member can also be different functional members.

Distinguishing members are at least different in their appearance, such as color and printing. Additionally, they can also be mechanically different, that is they can be different in shape. Despite being different in appearance and, optionally shape, the individual distinguishing members perform the same function during dose setting and dose delivery and thus constitute the same functional member among the individual drug delivery devices 220, 222, 225. The individual distinguishing elements are therefore designated by the same term in all drug delivery devices 200, 220, 222, 225.

The functional members constitute the individual parts of which the drug delivery devices 220, 225, 225 are assembled. While the individual parts can differ in their exact shape and appearance, for example to provide different dose increments among the individual drug delivery devices 220, 225, 225, they perform the same function and are located at the same positions within the dosing mechanisms 230 of the individual drug delivery devices 220, 225, 225. Furthermore, they interact and engage with the same further functional members of the dosing mechanism 230 among all drug delivery devices 220, 225, 225 of the set. Functional members can be composed of several sub-parts that are rigidly connected to each other to form a single mechanical part. With one embodiment of the present disclosure, a dosing member may, for example, constitute a functional member that is composed of two sub-parts, namely a dose sleeve and a snap element.

The first and second drug delivery device 220, 222 form a first set of drug delivery devices that mechanically differ only by their outer housings 221, 223, which carry the keyed connection means 510, 520. All other functional members of the drug delivery devices 220, 222 of the first set are mechanically identical. Therefore, the dosing mechanisms 240 and the dose definition mechanisms 232 of the two drug delivery devices 220, 222 are also the same. The two drug delivery devices 220, 222 are therefore configured to define identical rotational dose positions of the dose setting member 290 and to expel the same amount of liquid per settable dose increment.

One of the first set of drug delivery devices 220, 222 is configured to be used with its corresponding dispensing unit 420, 430 containing a drug having an active pharmaceutical ingredient in a first concentration and the other one of the first set of drug delivery devices 220, 222 is configured to be used with its corresponding dispensing unit 420, 430 containing the drug having the active pharmaceutical ingredient in a second concentration that is different from the first concentration.

Among the drug delivery devices 220, 222 of the first set, the piston rods 240, the plunger discs 242, the drivers 350, the nuts 250, the dose setting members 290, the first and second bearing elements 370, 380, the biasing members 308, the inner housings 180 and all elements of the resetting mechanism 110, namely the resetting elements 110, the coupling parts 130 and the biasing members 150, each form mutual members that are mutually identical both in appearance and shape among the two drug delivery devices 220, 222.

The dosing members 330 of the two drug delivery devices 220, 222 of the first set form a distinguishing member that differs in appearance but not in shape among the two drug delivery devices 220, 222. The difference in appearance thereby includes different numerals of the visual indicators 331, whereby the individual indicators 331 are located at the same positions on the dosing members 330 of the respective two drug delivery devices 220, 222.

The outer housings 211 of the two drug delivery devices 220, 222 of the first set form distinguishing elements that differ in shape due to the differences of their connection means 511, 520. Furthermore, the outer housings 211 differ in appearance, such as in color and/or labelling, to allow a user to clearly distinguish between the two devices 220, 222.

The dose selector members 310 and the caps 209 of the two drug delivery devices 220, 222 of the first set also form distinguishing members that differ in appearance but not in shape among the two drug delivery devices 220, 222. The difference in appearance thereby include different labelling on the dose selector member 310 and the cap 209. Furthermore, the caps 209 differ in color to match the colors of the respective body of their drug delivery device 220, 222. With other embodiments, the dose selector member 310 and/or the caps 209 can also be configured as mutual members. Furthermore, the caps 209 could also differ only in color and not in labelling or vice versa.

Each one of the first and second drug delivery device 220, 222 forms together with the third drug delivery device 225 a second set of drug delivery devices 200, 220, 225 that mechanically differ not only by their outer housings 211 but also by functional members of their dose definition mechanisms 232.

The dosing mechanism 230 of the third drug delivery device 225 is configured to provide a dialling resolution that is different from the dialling resolution of the first and second drug delivery device 220, 222. While the dosing mechanisms 230 of the first and second drug delivery device 220, 222 comprise the dose selector member 310 and the dose setting member 290 described in connection with FIG. 1 to FIG. 35, which are configured to define 27 settable dose positions, the third drug delivery device 225 comprises embodiments of the dose selector member 310 and the dose setting member 290 that are configured to define 18 settable dose positions.

The dose selector member 310 of the third drug delivery device 225 comprises 18 functional features 312 that are distributed around its inner surface. A position of the elastic elements 292 of the dose setting member 290 is thereby adapted to the larger distance between the individual functional features 312 to allow for reliable engagement between the elastic elements 292 and the functional features 312.

Since the dose definition mechanisms 332 of the third drug delivery device 225 define an even number of settable doses, the connection 277 between the clutch member 270 and the dose setting member 290 is configured to connect the clutch member 270 and the dose setting member 290 in two different relative rotational orientations that differ from each other by 180°. To achieve this, the first and second longitudinal grooves 297 and 298 of the dose setting member 290 and the corresponding first and second ridge 279, 280 of the clutch member 270 each have the same widths.

The clutch member 270 of the third drug delivery device 225 comprises 18 clutch elements 273, the circumferential positions of which are adapted to the circumferential positions of the functional features 312 of the dose selector member 310. Therefore, the number and circumferential positions of the clutch elements 273 of the clutch member 270 of the third drug delivery device 225 differs from the number and circumferential positions of the clutch elements 273 of the clutch member 270 of the first and second drug delivery device 220, 222.

The clutch members 270 of, on the one hand, the first and second drug delivery devices 220, 222 and of, on the other hand, the third drug delivery device 225 form distinguishing members that differ in shape among the second sets of drug delivery devices 220, 222 225. Likewise, the dose setting members 290 of, on the one hand, the first and second drug delivery devices 220, 222 and of, on the other hand, the third drug delivery device 225 also form distinguishing members that differ in shape among the second sets of drug delivery devices 220, 222 225.

The dosing member 330 of the third drug delivery device 225 comprises 18 clutch elements 336, the circumferential positions of which are adapted to the circumferential positions of the clutch elements 273 of the clutch member 270. Therefore, the dosing member 330 of the third drug delivery device 225 and each one of the dosing members 330 of the first and second drug delivery device 220, 222 form distinguishing members that differ in shape among the second sets of drug delivery devices 220, 222 225.

With all drug delivery devices 200, 220, 222, 225, the clutch elements 273 of the clutch member 270, the clutch elements 336 of the dosing member 330, the clutch elements 312 of the dose selector member 310 and the clutch elements 294 of the dose setting member 290 are rotationally aligned with respect to each other in a way that in each rotational position of the dose setting member 290, in which the clutch elements 273 of the clutch member 270 and the clutch members 336 of the dosing member 360 are aligned with each other to allow mutual engagement, also the clutch elements 294 of the dose setting member 290 and the clutch elements 312 of the dose selector member 310 are aligned with each other to allow mutual engagement.

The dosing member 330 of the third drug delivery device 225 furthermore differs from the dosing member 330 of the first and second drug delivery device 220, 222 in appearance, as the positions of the optical markers 331 on the dosing member 330 of the third drug delivery device 225 differ from the positions of the optical markers 331 on the dosing members 330 of the first and second drug delivery devices 220, 222 to reflect the different number of doses settable per revolution of the dose setting member 290.

The numbering of the individual optical markers 331 on the dosing member 330 of the first drug delivery device 220 differs from the numbering of the individual optical markers 331 on the dosing member 330 of the third drug delivery device 225. This allows the first drug delivery device 220 to be used with a drug that has a first concentration of an active pharmaceutical ingredient and the third drug delivery device 225 to be used with a drug having a third concentration of an active pharmaceutical ingredient, whereby the product of the first concentration with the amount of liquid that is expelled by the first drug delivery device 220 per dose increment differs from the product of the third concentration with the amount of liquid that is expelled by the third drug delivery device 225 per dose increment.

The numbering of the individual optical markers 331 on the dosing member 330 of the second drug delivery device 222 equals the numbering of the individual optical markers 331 on the dosing member 330 of the third drug delivery device 225. This enables the second drug delivery device 220 to be used with a drug that has a second concentration of an active pharmaceutical ingredient and the third drug delivery device 225 to be used with a drug having a third concentration of an active pharmaceutical ingredient, whereby the product of the second concentration with the amount of liquid that is expelled by the second drug delivery device 222 per dose increment is equal to the product of the third concentration with the amount of liquid that is expelled by the third drug delivery device 225 per dose increment.

Due to the differences in shape and appearance, the dosing member 330 constitutes a distinguishing member among the second sets of drug delivery devices 220, 222, 225.

In total, mutual members of the second sets of drug delivery devices 220, 222, 225 are the piston rod 240, the plunger disc 242, the nut 250, the driver 350, the bearing elements 370, 380, the biasing member 308, the inner housing 180 and all elements of the resetting mechanism 110, namely the resetting element 110, the coupling part 130 and the biasing member 150.

Distinguishing members that only differ in appearance but not in shape among the second sets of drug delivery devices 220, 222, 225 are the caps 209, each of which has a different color. Distinguishing members that differ both in appearance and in shape among the second sets of drug delivery devices 220, 222, 225 are the outer housings 211, each of which has a different color and a differently shaped connection means 511, 520, 530, the dosing members 330, each of which has a different position and/or number and/or labelling of their optical markers 331 and differently shaped clutch elements 336, the dose selector members 310, each of which has a different labelling and differently shaped functional features 312, the clutch members 270, which differ in the shapes of their clutch elements 273 and hence also in their appearance, and the dose setting members 290, which differ in the positions of their elastic elements 292 and their clutch elements 294 and hence also in their appearance.

The first drug delivery device 220 is configured to be used with a drug containing the active pharmaceutical ingredient in a concentration of 5 mg/1.5 ml, the second drug delivery device 222 is configured to be used with drug containing the active pharmaceutical ingredient in a concentration of 10 mg/1.5 ml and the third drug delivery device 225 is configured to be used with a drug containing the active pharmaceutical ingredient in a concentration of 15 mg/1.5 ml. Both the first and second drug delivery device 220, 222 have a dialing resolution of 0.015 ml per dose increment and the third drug delivery device 225 has a dialing resolution of 0.010 ml per dose increment.

The optical markers 331 on the dosing member 330 of the first drug delivery device 220 then display dose increments of 0.05 mg and the optical markers 331 on the dosing members 330 of the second and third drug delivery device 222, 225 then each display dose increments of 0.10 mg. All drug delivery devices 220, 222, 225 allow for two full rotations of the dose setting member 290 during dose setting. With 27 dose increments per revolution of the dose setting member 290, the first drug delivery device 220 is configured to expel a maximum dose of the active pharmaceutical ingredient of 1.80 mg and the second drug delivery device 222 is configured to expel a maximum dose of the active pharmaceutical ingredient of 3.60 mg. Since the third drug delivery device 225 provides 18 dose increments per revolution of the dose setting member 290, it is configured to deliver a maximum dose of the active pharmaceutical ingredient of 5.40 mg.

The dose stops according to the present disclosure are also applicable with other drug delivery devices, for example, injection devices. A further possible injection device is the pen-type further drug delivery device 10 illustrated in FIG. 38 to FIG. 40. As far as no differences are described or apparent from the Figures, the further drug delivery device 10 is configured as it is disclosed in connection with the drug delivery device 200 and vice versa. The further drug delivery device 10 is also described in more detail in international applications WO2020/015980A1 and WO2019/011394A1, the disclosure of each of which is incorporated into this disclosure in its respective entirety by reference.

The further drug delivery device 10 has an outer housing 3 connected to a dispensing unit 410 with a cartridge holder 2 holding a cartridge 8. The cartridge holder 2 has a needle connector 402. The injection device 10 has a dosing mechanism 30 and is illustrated in the zero-dose state as indicated by an optical marker 40 showing a zero through a window 3a of the outer housing 3. The outer housing 3 terminates at its proximal end in a keyed connection means 510, which has a thread form.

Figure 40:
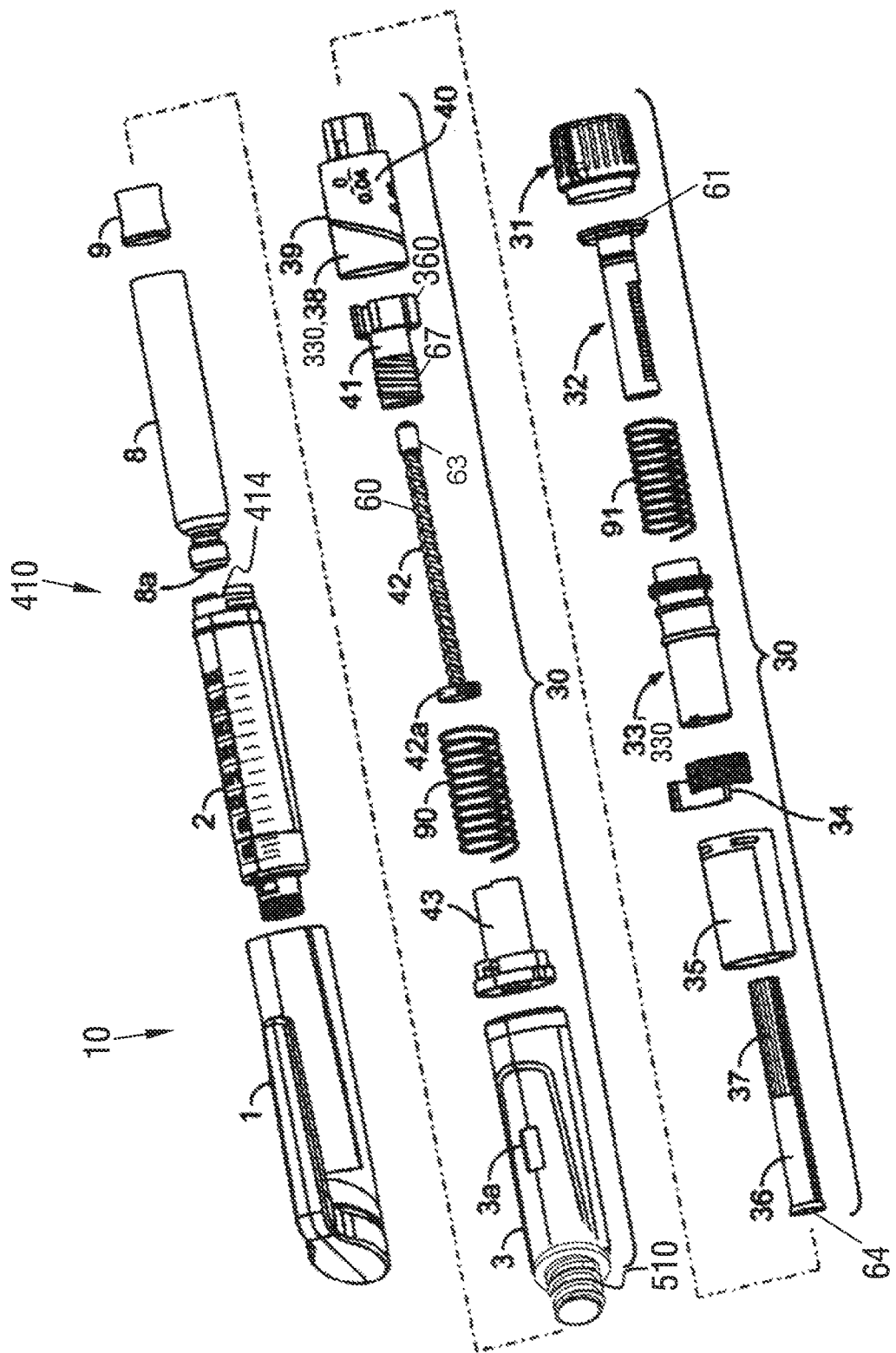
FIG. 40 is an exploded view of the further drug delivery device.

FIG. 40 schematically shows a simplified exploded view of the device 10 with a cap 1 removed to expose the cartridge holder 2 and the proximal needle connector 402. The needle 4 is typically attached to the needle connector 402 through a snap fit, thread, Luer-Lok, or other secure attachment with hub 5 such that a double ended needle cannula 6 can achieve a fluid communication with a drug contained in the cartridge 8 positioned within cartridge holder 2.

The particular design of the device 10 allows for setting of one or more of predetermined fixed doses through the interaction of a snap element 33 with a dose selector member 35. A rotation of a dose setting member 31 and the snap element 33 occurs during dose setting and is relative to outer housing 3. During the initiation of the dose delivery procedure the dose setting member 31 is pressed in the proximal direction causing it and the dose selector member 35 to move axially relative to the snap element 33. Like with the drug delivery device 200, the dose selector member 35 is axially movable and rotationally fixed with respect to the outer housing 3 of the further drug delivery device 10.

Part of the dosing mechanisms of most pen-type injectors, including device 10, is a piston rod 42 as illustrated in FIG. 40. Such piston rods usually have a non-circular cross-section and have two flat surfaces that are designed to prevent the piston rod 42 from rotating with respect to the outer housing 3 but allowing it to move linearly in the proximal direction. A nut 36 and a clutch member 32 are permanently splined to each other during assembly of the dosing mechanism 30 through a splined connection 37. The splined connection 37 ensures that the clutch member 32 and the nut 36 are always rotationally fixed to each other during both dose setting and dose delivery. This splined connection 37 also allows the clutch member 32 and the nut 36 to move axially relative to each other during both dose setting and dose delivery.

The proximal end of the nut 36 has an internal thread that matches a corresponding outer thread 60 of the piston rod 42. The distal end of the clutch member 32 is configured as a dose button 61 and is permanently attached to the distal end of the dose setting member 31 through engagement of connectors, which can be configured as snap locks, an adhesive and/or a sonic weld. This connection ensures that the clutch member 32 is both rotationally and axially fixed to the dose setting member 31 during both dose setting and dose delivery. Alternatively, the clutch member 32 and the dose setting member 31 could also be configured as a single member.

At the terminal proximal end of the piston rod 42 is a connector, which is configured as a snap fit, that connects with a plunger disc or foot 42a. At the distal end of the piston rod 42 is a stop feature 63 of the dosing mechanism 30, illustrated as an enlarged section. This enlarged section 63 is designed to stop the rotation of the nut 36 about the thread 60 when the amount of medicament remaining in the cartridge 8 is less than the next highest predetermined dose setting. In other words, if the user tries to set one of the predetermined fixed dose settings that exceeds the amount of medicament remaining in the cartridge 8, then the enlarged section 63 will act as a hard stop preventing the nut 36 from further rotation along the thread 60 as the user attempts to reach the desired predetermined fixed dose setting. With the drug delivery device 200, the stop feature 243 interacts with the nut 250 in the same way and therefore also prevents setting of a dose larger than the remaining dose within the cartridge 8.

The piston rod 42 is held in a non-rotational state relative to the outer housing 3 during both dose setting and dose delivery by a piston rod guide 43. The piston rod guide 43 is both rotationally and axially fixed to the outer housing 3. Therefore, it forms part of a housing of the device 10. This fixation can be achieved when the piston rod guide 43 is a separate component from the outer housing 3 as illustrated or the piston rod guide 43 could be made integral with the outer housing 3, analogous to the inner sleeve 183 of the inner housing 180 of the drug delivery device 200. Although not shown in the Figures, the piston rod guide 43 is configured as a resetting mechanism that, like the resetting mechanism 100 of the drug delivery device 200, prevents rotation of the piston rod 42 with respect to the housing 3 when the dispensing unit 410 is attached to the housing 3 of the drug delivery device 10 and that allows rotational movement of the piston rod 42 with respect to the housing 3 when the dispensing unit 410 is disengaged from the housing 3.

The resetting mechanism of the further drug delivery device 10 can be configured as it is disclosed in connection with the resetting mechanism 100 of the drug delivery device 200. In particular, the resetting mechanism of the further drug delivery device 10 can comprise the resetting element 110, the coupling part 130 and the biasing element 150.

The piston rod guide 43 also engages the proximal end of a rotational biasing member 90, shown as a torsion spring, the function of which will be explained below. This connection of the rotational biasing member 90 to the piston rod guide 43 anchors one end of the rotational biasing member 90 in a rotationally fixed position relative to the outer housing 3.

The distal end of the rotational biasing member 90 is connected to a driver 41. The driver 41 is connected to and rotationally fixed with respect to an inner surface of a dosing member 330 through a splined connection on the distal outer surface of the driver 41. This splined connection comprises at least one, such as two longitudinal ridges that are located on the outer diameter of the driver 41 and that engage with corresponding grooves on the inner surface of the dosing member 330. On the proximal end of the driver 41 on the outer surface is a thread 67 that is engaged with a matching thread on the inner distal surface of the piston rod guide 43.

The dosing member 330 comprises two parts that are rotationally and axially fixed to each other, for example by a snap-fit connection. One part forms a dose sleeve 38 that is connected to the driver 41 through the splined connection, the other part forms the snap element 33. As such, the dosing member 330 forms a single functional member.

The dosing member 330, namely the dose sleeve 38 is threadedly engaged with the body 3 by a helical groove 39 located on the outer surface of the dosing member 330 that engages with a corresponding helical ridge located on the inner surface of the body 3. The thread between the driver 41 and the piston guide 43 has a significantly different pitch than the thread between the dosing member 330 and the outer housing 3. The axially sliding connection between the nut 36 and the clutch member 32 allows to compensate for the differences in the pitch of the thread between the inner surface of the nut 36 and the outer surface of the piston rod 42 and the pitch of the thread between the dosing member 330 and the body 3. The thread between the driver 41 and the piston guide 43 has basically the same pitch as the thread between the piston rod 42 and the nut 36.

The nut 36 and the driver 41 rotate together both during dose setting and dose cancellation and, as such, they perform essentially the same axial movement. However, these movements are independent from each other, i.e., the nut 36 is turned by the clutch member 32 and performs an axial movement due to the thread to the piston rod 42, while the driver 41 is rotated by the dosing member 330 and performs an axial movement due to the thread to the piston guide 43. The driver 41 is rotating during injection also, and so it actively moves in the proximal direction during injection. But, the nut 36 does not rotate during injection and as such does not perform an active axial movement. The nut 36 is only moving in the proximal direction during injection because it is being pushed axially by the driver 41, which surrounds the nut 36 and abuts against a protrusion 64 located at the proximal end of the nut 36. The rotating driver 41 pushing the non-rotating nut 36 causes the injection because the piston rod 42 is pushed forward due to the threaded engagement with the nut 36.

Because the torsion spring 90 is attached to the driver 41 and the driver 41 is rotationally fixed to the dosing member 330, rotation of the dosing member 330 in a first direction during dose setting will wind the torsion spring 90 such that it exerts a counter rotational force on the dosing member 330 in an opposite second direction. This counter rotational force biases the dosing member 330 to rotate in a dose canceling direction.

The function of the complete further drug delivery device 10 and the dosing mechanism 30 will now be described. The further drug delivery device 10 is provided to a user as reusable or semi-reusable device. A semi-reusable device means that only the dosing mechanism 30 housed in the outer housing 3 is reused each time a new dispensing unit 410 having a cartridge holder 2 containing a new cartridge 8 of medicament is connected to the outer housing 3. A reusable device would allow reattachment of an old or previously used cartridge holder 2 where the user has inserted a new full cartridge 8 of medicament. In one configuration according to the present disclosure, the device 10 has the semi-reusable design where each time the medicament in the cartridge 8 is expelled or emptied, the user would be required to disconnect the cartridge holder 2 containing the empty cartridge 8 that is not removable from the cartridge holder 2. As such, the user would dispose of both the cartridge holder 2 and the empty cartridge 8 together. A new cartridge holder 2 and cartridge 8 assembly would be connected to the outer housing 3 provided that the keyed connection device 510 on the outer housing 3 matches a keyed connection device 414 provided on the distal end of the cartridge holder 2.

With the further drug delivery device 10, the dose sleeve 38 and the snap element 33 are axially and rotationally fixed with each other via a snap-fit connection. Therefore, the dose sleeve 38 and the snap element 33 constitute a single functional element, namely the dosing member 330. With other embodiments of the further drug delivery device 10, the dosing member 330 could also be configured as a single component or member.

A housing of the further drug delivery device 10 comprises the outer housing 3 and the piston guide 43, which are rotationally and axially fixed with respect to each other.

Like the drug delivery device 200, the further drug delivery device 10 comprises a clutch mechanism 237. During dose setting, the clutch mechanism 237 rotationally fixes the nut 36 with respect to the driver 41 and the dosing member 330 and enables rotation of the nut 36 with respect to the housing 3, 43. During dose delivery, the clutch mechanism 237 rotationally fixes the nut 36 with respect to the dose selector member 35 and the housing 3, 43 and allows relative rotation between the nut 36 on the one hand and the driver 41 and the dosing member 330 on the other hand.

Figure 41:
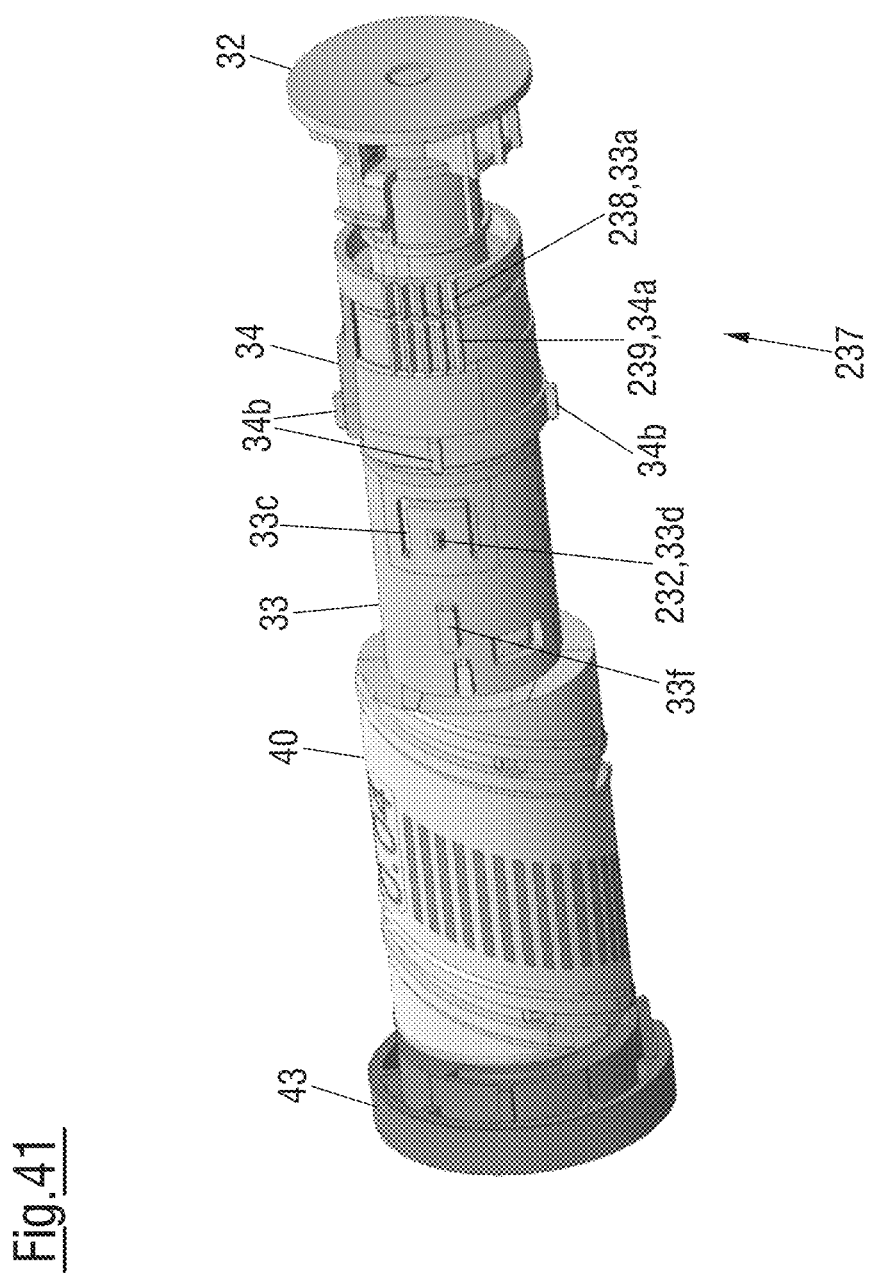
FIG. 41 is a clutch mechanism of the further drug delivery device.
Figure 42:
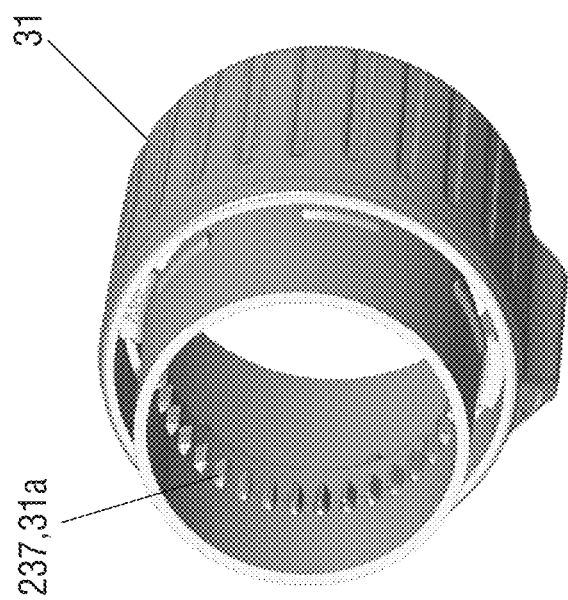
FIG. 42 is a dose setting member of the further drug delivery device.

As can be seen from FIG. 41 and FIG. 42, a first part 238 of the clutch mechanism 237 comprises clutch elements 33a that are configured as radially extending teeth and that are disposed on an outer surface at a distal end of the snap element 33 of the dosing member 330. A second part 239 of the clutch mechanism 237 comprises clutch elements 34a that are configured as radially extending teeth and that are disposed on an outer surface at a distal end of a connector 34.

The connector 34 is located within an annular recess of the dosing member 330 and is thereby rotationally movable and axially fixed with respect to the dosing member 330. The connector 34 is axially movable and rotationally fixed with respect to the dose selector member 35. This is exemplarily achieved by radially protruding ridges 34b of the connector 34 that are received in corresponding longitudinal grooves on an inner surface of the dose selector member 35. The rotationally fixed connection to the dose selector member 35 also rotationally fixes the connector 34 to the housing 3, 34 of the further drug delivery device 10.

The dosing member 330 surrounds the clutch member 32 and the clutch member 32, together with the dose setting member 31 and the dose selector member 35, is axially movable with respect to the dosing member 330. Thereby, the dose setting member 31 and the clutch member 32 are biased into the distal direction by a compression spring 91 (shown in FIG. 40) that acts between the dosing member 330 and the clutch member 32. Axial movement of the clutch member 32 and the dose setting member 31 is allowed until the dose setting member 31 abuts the dosing member 330 via the dose selector member 35.

During dose setting, the clutch member 32 and the dose setting member 31 are in their distal position with respect to the dosing member 330. In this position, the dose setting member 31 is rotationally coupled to the dosing member 330 via the first part 238 of the clutch mechanism 237 that comprises the clutch elements 33a at the distal end of the snap element 33 of the dosing member 330 and corresponding clutch elements 31a on an inner surface of the dose setting member 31, which are shown in FIG. 42. When rotating the dose setting member 31 during dose setting, the dosing member 330 is also rotated via the closed first part 238 of the clutch mechanism 237 between the dose setting member 31 and the dosing member 330 and screwed out of the outer housing 3. This forces the dose selector member 35 and the dose setting member 31 to also move in the distal direction. Rotation of the dosing member 330 also forces a corresponding rotation of the driver 41, which is therefore also screwed out of the piston guide 43.

Since the nut 36 is rotationally fixed with respect to the clutch member 32, rotation of the dose setting member 31 also causes rotation of the nut 36 during dose setting. Thereby, the nut 36 is screwed along the piston rod 42 and also moves into the distal direction. The pitches of the threads of the piston rod 42 and the driver 41 are adapted so that the nut 36 and the driver 41 essentially move the same axial distance upon rotation. Thereby, the nominal pitch of the connection between the driver 41 and the piston guide 43 is slightly higher than the nominal pitch of the thread between the piston rod 42 and the nut 36 to prevent mutual blocking of the nut 36 and driver 41 irrespective of manufacturing tolerances.

To eject a set dose, the dose setting member 31, the clutch member 32 and the dose selector member 35 are moved into their proximal position with respect to the dosing member 330. This releases the first part 238 of the clutch mechanism 237 between the snap element 33 of the dosing member 330 and the dose setting member 31 and engages the second part 239 of the clutch mechanism 237, which is realized between the dose setting member 31 and the connector 34 that surrounds the dosing member 330. Upon engagement of the second part 239 of the clutch mechanism 237, the clutch elements 31a of the dose setting member 31 engage with the clutch elements 34a of the connector 34.

Engagement of the second part 239 of the clutch mechanism 237 rotationally locks the dose setting member 31 and the clutch member 32 to the connector 34 and, via the ridge 34b of the connector 34, also to the dose selector member 35 and the housing 3, 43. Therefore, the nut 36 is rotationally locked with respect to the housing 3, 43 and the piston rod 42 during dose delivery. This locking is achieved via the nut 36, the clutch member 32, the dose setting member 31, the connector 34 and the dose selector member 35.

Disengagement of the first part 238 of the clutch mechanism 237 allows rotational movement between the nut 36 and the driver 41 during dose delivery.

When further pushing the dose setting member 31 into the proximal direction, the dose selector member 35 abuts against the dosing member 330 and forces the dosing member 330 to move into the proximal direction. Due to the threaded connection between the dosing member 330 and the outer housing 3, the dosing member 330 rotates when moving into the proximal direction. This rotation is transferred to the driver 41, which is screwed into the proximal direction into the piston guide 43 and therefore also moves axially in the proximal direction. The driver 41 thereby abuts and advances the nut 36, which is now rotationally fixed to the outer housing 3 and the piston rod 42 via the clutch member 32, the dose setting member 31, the connector 34 and the dose selector member 35. Therefore, both the piston rod 42 and the nut 36 are rotationally fixed with respect to each other and axial advancement of the nut 36 causes a corresponding axial advancement of the piston rod 42, thus expelling the set dose.

Like the drug delivery device 200, also the further drug delivery device 10 can comprise one or more friction reduction mechanisms that reduce friction within the dosing mechanism 30 during delivery of a set dose. These friction reduction mechanisms mac be configured in the same way as it is disclosed in connection with the drug delivery device 200.

For example, the first friction reduction mechanism can be disposed between the dose selector member 35 and the dosing member 330. When pushing the dose setting member 31 in the proximal direction, the dose selector member 35, for example the proximal end of the dose selector member 35, can abut against the dose sleeve 38, for example against the distal end of the dose sleeve 38. The first friction reduction mechanism, such as the ball bearing 370 can then be disposed between the dose selector member 35 and the dose sleeve 38, for example between the proximal end of the dose selector member 35 and the distal end of the dose sleeve 38.

Additionally or alternatively, the second friction reduction mechanism can be disposed between the driver 41 and the nut 36 in the same ways as it is disclosed in connection with the second friction reduction mechanism, such as the disc bearing 380, of the drug delivery device 200.

Figure 43:
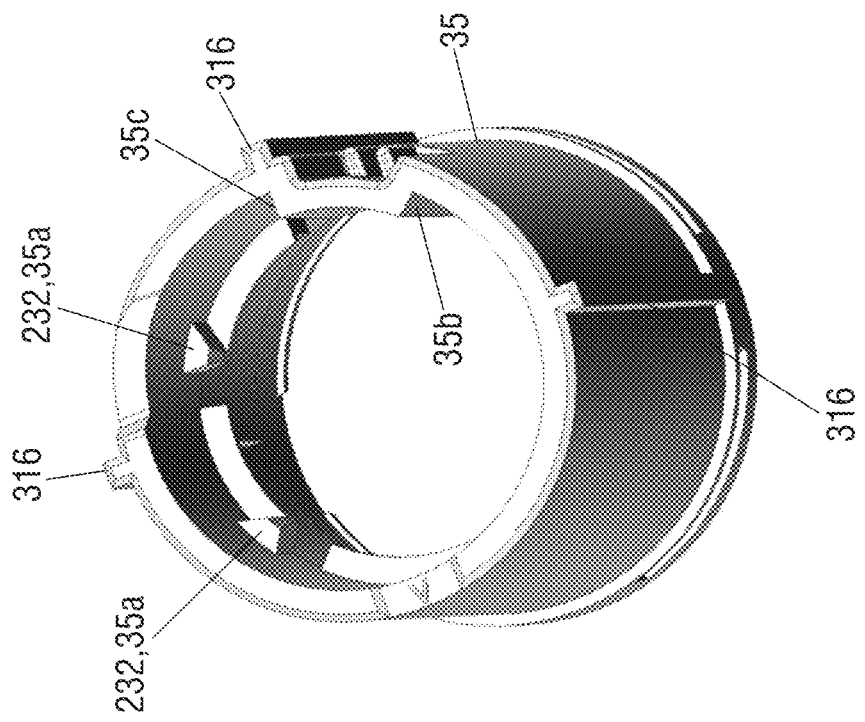
FIG. 43 is a dose selector member of the further drug delivery device.

The further drug delivery device 10 comprises a dose definition mechanism 232 that acts between the snap element 33 of the dosing member 330 and the dose selector member 35. During dose setting, the dosing member 330 rotates with respect to the dose selector member 35. As can be seen from FIG. 41, the dosing member 330 has, on its outer surface, a flexible arm 33c with a radial protrusion 33d, which forms an elastic element and engages with dose stops 35a on the inner surface of the dose selector 35. The dose stops 35a, which are shown in FIG. 43, form functional features of the dose definition mechanism 232.

The circumferential positions of the individual dose stops 35a thereby define individual relative rotational positions between the dose setting member 31 and the housing 3, 43 that correspond to settable doses. To prevent the dialing of intermediate doses in between the individual dose stops 35a, the torsion spring 90 is disposed between the piston guide 43 and the driver 41. This torsion spring 90 is loaded when increasing the set dose and causes the dosing member 330 to rotate back to the last set dose in cases where the dose setting member 31 is released while the protrusion 33d on the dosing member 330 is positioned in between two dose stops 35a.

With the further drug delivery device 10, the dose setting member 31 is limited to perform less than one full rotation upon dose setting. The further drug delivery device 10 comprises a stop mechanism that defines a maximum and minimum rotational position of the dose setting member 31 during dose setting.

The stop mechanism acts between the snap element 33 of the dosing member 330 and the dose selector member 35. It comprises a further protrusion 33f that is located on the outer surface of the dosing member 330 and that radially protrudes towards the dose selector member 35. The dose selector member 35 comprises a maximum stop feature 35b that is located on an inner surface of the dose selector member 33 and that is configured as a side surface of a step located on the inner surface. Furthermore, the dose selector member 35 comprises a zero stop feature 35c that is located also on the inner surface of the dose selector member 33. The zero stop feature 35c is exemplarily configured as a side surface of the step that opposes the side surface forming the maximum stop feature 35b.

The further protrusion 33f of the dosing member 330 is configured to abut the maximum stop feature 35b upon rotation of the dose setting member 31 into a rotational position that corresponds to or exceeds a maximum settable dose and thereby prevents further rotation of the dose setting member 31. Likewise, the further protrusion 33f of the dosing member 330 is configured to abut the zero stop feature 35c upon rotation of the dose setting member 31 into a rotational position that corresponds to a zero dose setting and thereby prevents further rotation of the dose setting member 31.

The further drug delivery device 10 can also comprise an alternative embodiment of the stop mechanism that defines a maximum dose position and/or a zero dose position of the dosing member 330 with respect to the housing 3, 43. The alternative embodiment disposed be configured like the stop mechanism of the drug delivery device 200. Thereby, a maximum dose stop can be provided at the dosing member 330, such as at the dose sleeve 38 or the snap element 33, and a corresponding maximum stop feature can be provided at the housing 3, 43. The maximum dose stop and/or the maximum stop feature disposed be configured as it is described in connection with the maximum dose stop 337 and the maximum stop feature 190 of the drug delivery device 200.

Likewise, the alternative embodiments of the stop mechanism of the further drug delivery device 10 disposed comprise a zero dose stop that is provided at the dosing member 330, such as at the dose sleeve 38 or the snap element 33, and a corresponding zero stop feature that is provided at the housing 3, 43, for example at the piston guide 43. The zero dose stop and/or the zero stop feature disposed be configured as it is described in connection with the maximum dose stop 337 and the maximum stop feature 190 of the drug delivery device 200.

Like the drug delivery device 200, the further dose delivery device 10 can be provided in several variants that are distinguished by their connection device 510 to be configured to only connect to a dedicated variant of the dispensing unit 410. The connection device 510 can thereby be configured as it is disclosed in connection with FIGS. 36A-36C and FIGS. 37A-37C.

In one embodiment, the several variants of the further drug delivery device 10 comprise as distinguishing members the outer housing 3, the cap 1, the dose sleeve 38 and the dose selector member 35. The outer housings 3 differ in shape due to the differences in the connection means 510 and also in appearance due to different colors and/or labeling. The dose selector members 35 differ in shape due to different numbers and/or different positions of the dose stops 35a, which allows to realize different dialing resolutions or settable doses. Alternatively or additionally, the dose selector members 35 can also differ in the position of the maximum stop feature 35c. The dose sleeves 38 are mechanically identical among the individual variants but differ in appearance due to different positions and/or numbering of their optical markers. The caps 1 are identical in shape but differ in their appearance, like color and/or labelling. With other embodiments, the caps 1 could also be configured as mutual members.

Mutual members of the variants of the further drug delivery devices 10 then can be all other elements of the dosing mechanism 30.

With both types of drug delivery devices 10, 200 the mechanical advantage of the dosing mechanisms 230 during dose dispensing can be different among devices of the individual sets. For example, a set can comprise one device having a higher mechanical advantage than another device of the respective set. Among these devices, the driver 41, 350 and the part of the housing 210 that is threadedly connected to the driver 41, 350, like the inner housing 180 and the piston guide 43, can be distinguishing members that mechanically differ from each other due to different pitches of their threads 67, 186, 353. Additionally or alternatively, the dosing member 330, in particular the dose sleeve 38, and the part of the housing 210 that is threadedly connected to the dosing member 330, like the inner housing 180 and the housing 3, can be distinguishing members that mechanically differ from each other due to different pitches of their threads 39, 185, 335. All sets of drug delivery devices 10, 200 described in the present disclosure can comprise drug delivery devices 10, 200 that differ by the mechanical advantage of their dosing mechanisms 230 during dose dispensing.

Figure 44:
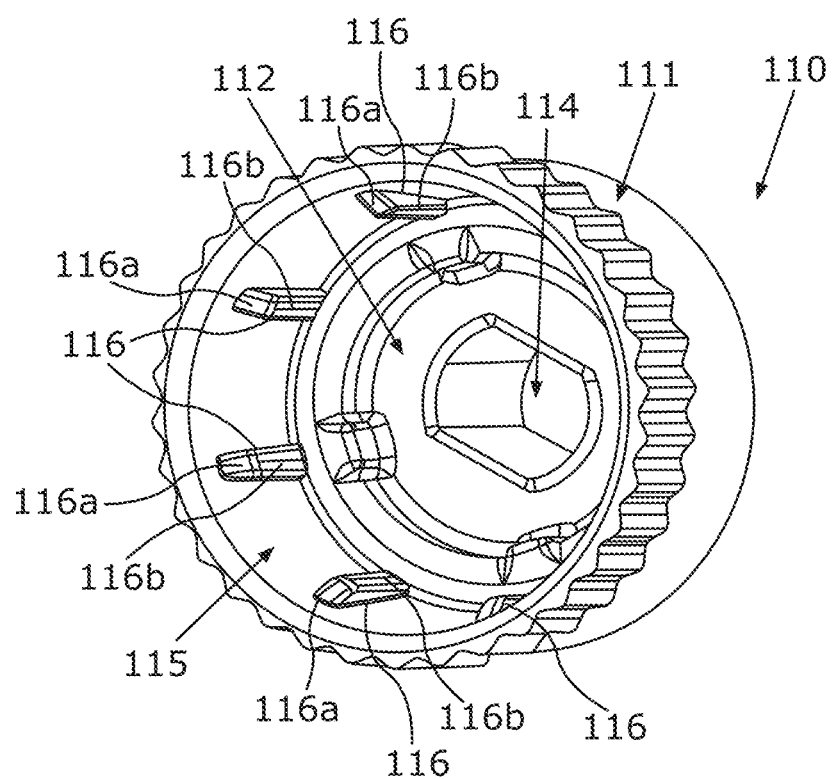
FIG. 44 is an alternative embodiment of the resetting element of the drug delivery device.
Figure 45:
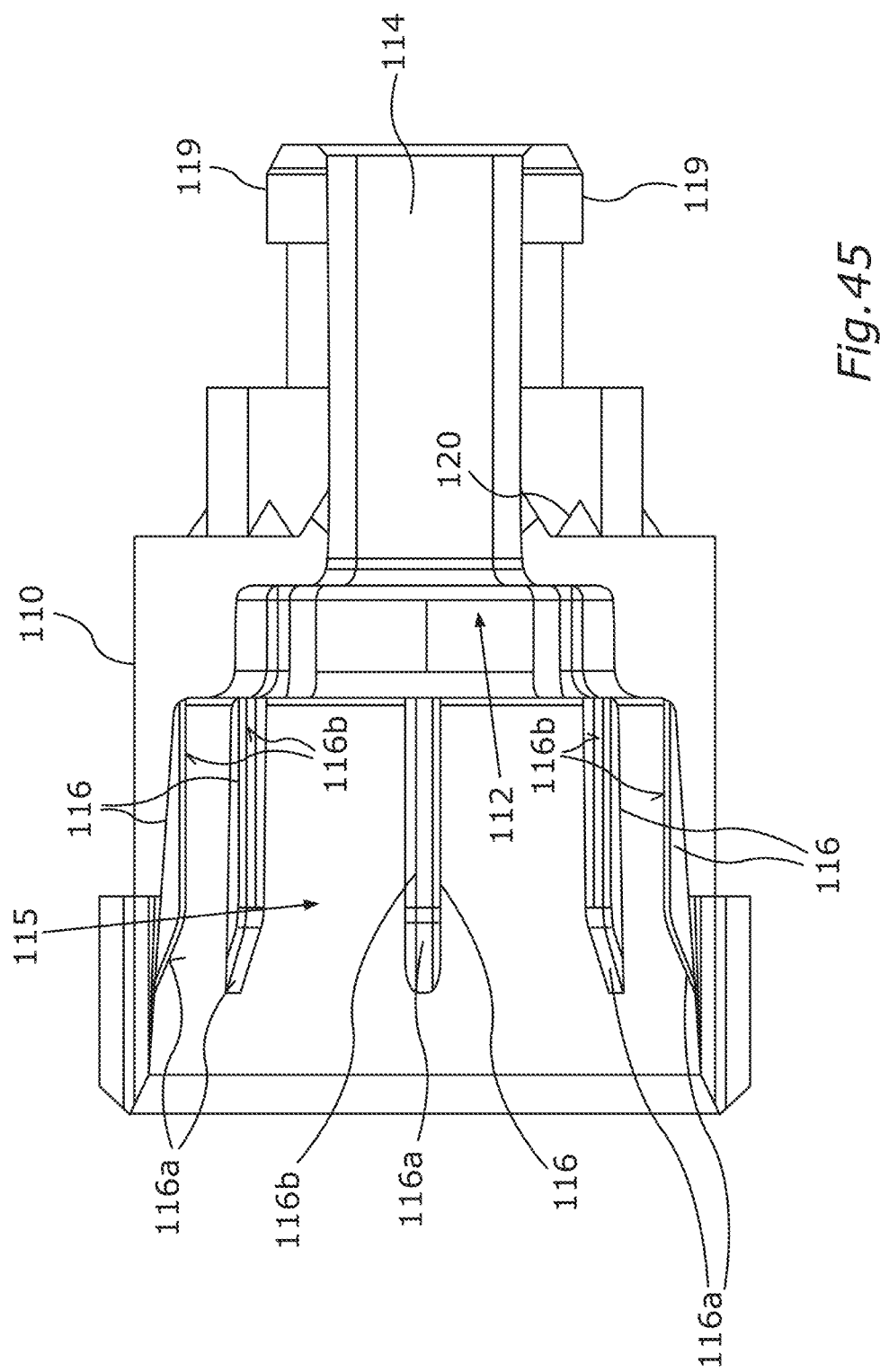
FIG. 45 is a longitudinal cross sectional view of the alternative embodiment of the resetting element.

FIG. 44 and FIG. 45 show an alternative embodiment of the resetting element 110 of the drug delivery device 200. As far as no differences are described or apparent from the Figures, the resetting element 110 according to the alternative embodiment is configured as it is described above in connection with the resetting element 110 of the drug delivery device 200 and vice versa.

The resetting element 110 comprises guiding structures 116 that are located within the cartridge cavity 115. The guiding structures 116 have an elongated shape and extend parallel to the longitudinal axis 207. They are placed on the circumferential side wall of the cartridge cavity 115. The guising structures 116 are thereby equally spaced apart from each other. With the embodiment shown in FIGS. 44 and 45, the resetting element 110 exemplarily comprises eight of the guiding structures 116. With other embodiments, the resetting element 110 can comprise more or less guiding structures 116.

The guiding structures 116 are configured to center the distal end of the cartridge 8 with respect to the longitudinal axis 207 when the dispensing unit 410 is attached to the drug delivery device 200. The guiding structures 116 radially touch a cartridge 8 that is inserted into the cartridge holder 412. As such, they only define the lateral position of the cartridge 8 with respect to the longitudinal axis 207 but not the axial position of the distal end of the cartridge 8. Furthermore, the axial position of the distal end of the cartridge 8 also does not define the axial position of the resetting element 110.

The guiding structures 116 are configured to not be pushed upon by the cartridge 8 during attachment of the dispensing unit 410 to the drug delivery device 200. The guiding structures 116 comprise an inclined front surface 116a that faces in the proximal direction. The inclined front surface 116a centers the cartridge 8 but prevents the resetting element 110 from receiving an axial force via the cartridge 8 that would axially displace the resetting element 110. The guiding structures 116 also comprise an inclined back surface 116b that faces in the distal direction.

Both the front surfaces 116a and the back surfaces 116b can have an angle with the longitudinal axis 207 that is at most 45°, for example at most 30°, 20° or 10°. For example, the front surfaces 116a can have an angle with the longitudinal axis 207 that is larger than 5°, larger than 10° or larger than 15° and/or smaller than 45°, smaller than 30°, or smaller than 25°. The angle may, for example, equal 20°. The back surfaces 116b can have, for example, an angle with the longitudinal axis 207 that is larger than 0° or larger than 0.5° and/or smaller than 10°, smaller than 5°, or smaller than 2.5°. The angle may, for example, equal 1°.

Figure 46:
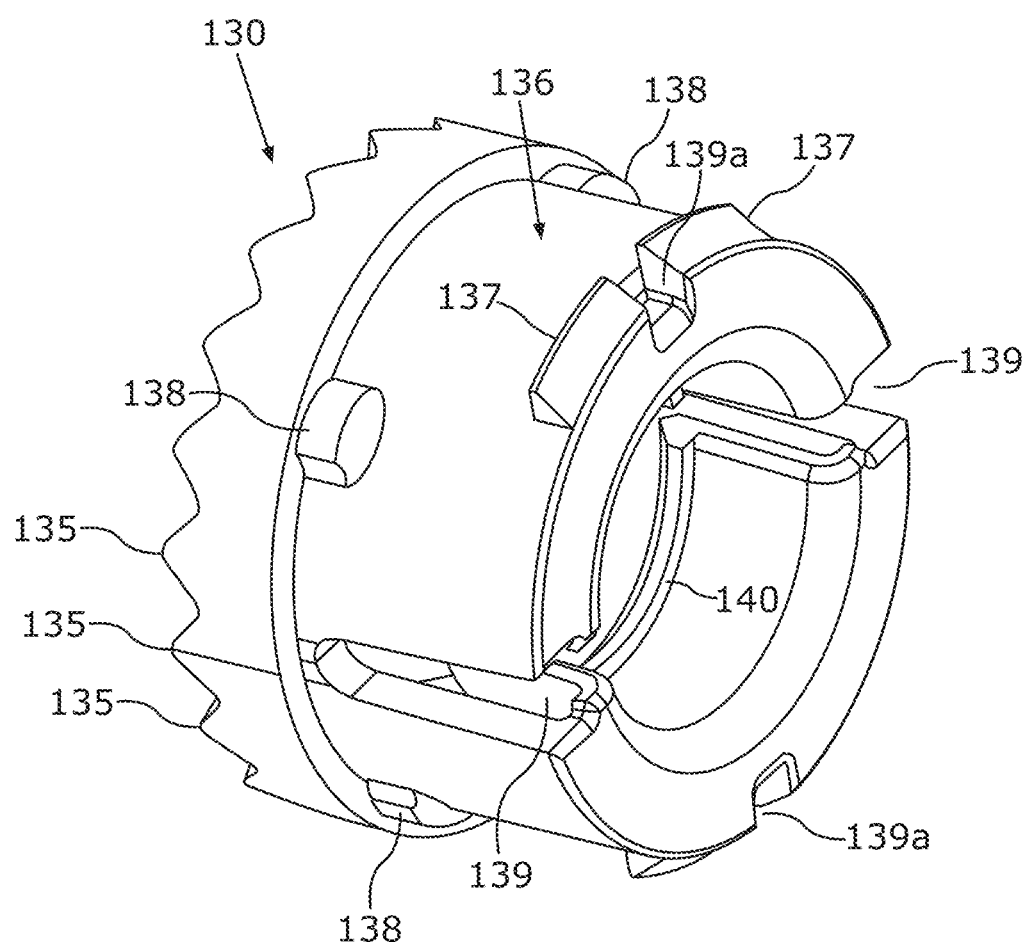
FIG. 46 is an alternative embodiment of the coupling part of the drug delivery device.

FIG. 46 shows an alternative embodiment of the coupling part 130 of the drug delivery device 200. As far as no differences are described or apparent from the Figures, the coupling part 130 according to the alternative embodiment is configured as it is described above in connection with the coupling part 130 of the drug delivery device 200 and vice versa.

The alternative embodiments of the coupling part 130 comprises four of the protrusions 138. The protrusions 138 are circumferentially distributed around the longitudinal axis 207 and equally spaced apart from each other in the circumferential direction.

Furthermore, the alternative embodiment of the coupling part 130 comprises, in addition to the slots 139, recesses 139a. In FIG. 46, the coupling part 130 is exemplarily shown having two of the recesses 139a. The recesses 139a are located at the distal end of the coupling part 130. Each recess 139a is centered with one of the first locking structures 137 and divides the respective first locking structure 137 into two parts. As can further be seen from FIG. 46, the slots 139 and the recesses 139a are alternately distributed in the circumferential direction and equally spaced from each other.

Figure 47:
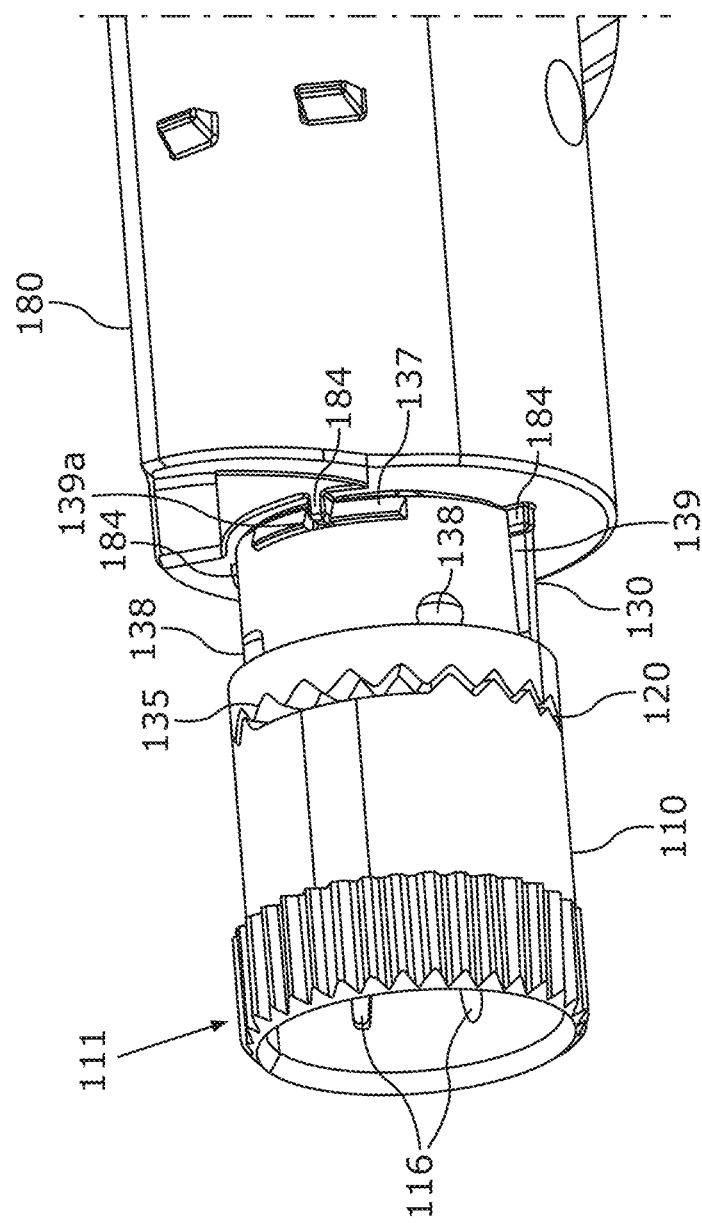
FIG. 47 is the alternative embodiment of the resetting element and the alternative embodiment of the coupling part mounted to an alternative embodiment of the inner housing of the drug delivery device.

FIG. 47 shows the alternative embodiment of the resetting element 110 and the alternative embodiment of the coupling part 130 mounted to an alternative embodiment of the inner housing 180. As far as no differences are described or apparent from the Figures, the alternative embodiment of the housing 180 is configured as it is described above in connection with the inner housing 180 of the drug delivery device 200 and vice versa.

The alternative embodiment of the inner housing 180 comprises one of the tappets 184 for each one of the slots 139 and recesses 139a. In total, the inner housing 180 therefore comprises four tappets 184. The tappets 184 are provided at the proximal end of the inner housing 180. Furthermore, they are equally spaced from each other in the circumferential direction around the longitudinal axis 207.

Figure 48:
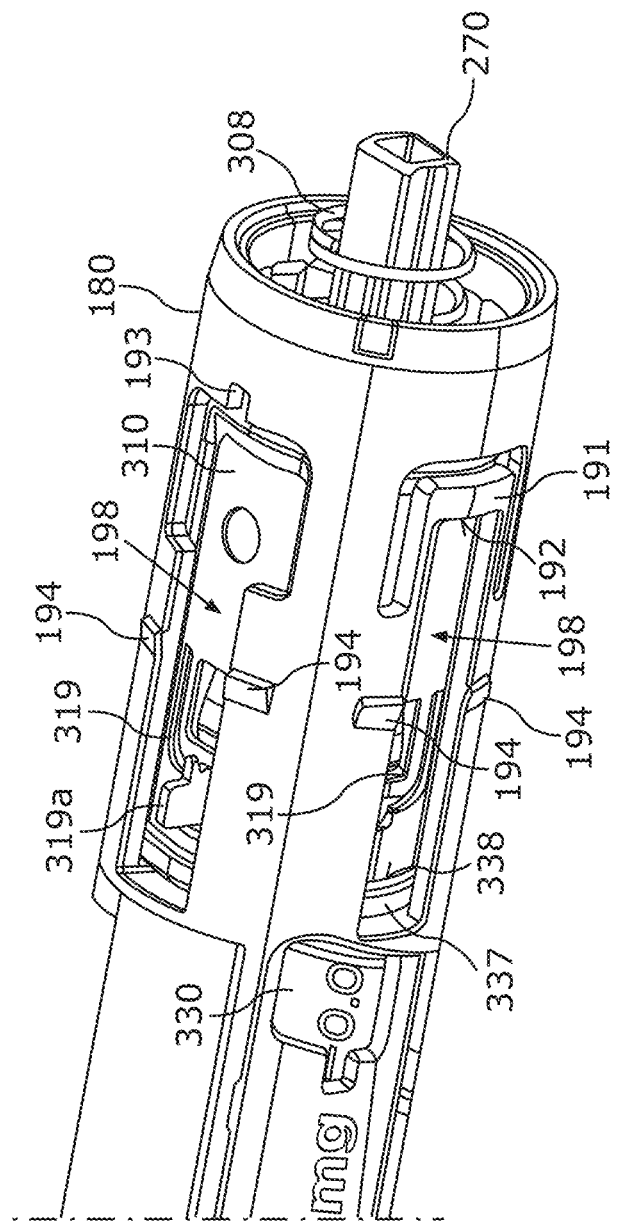
FIG. 48 is a perspective view of an alternative connection between a further alternative embodiment of the inner housing and an alternative embodiment of the dose selector member.
Figure 49:
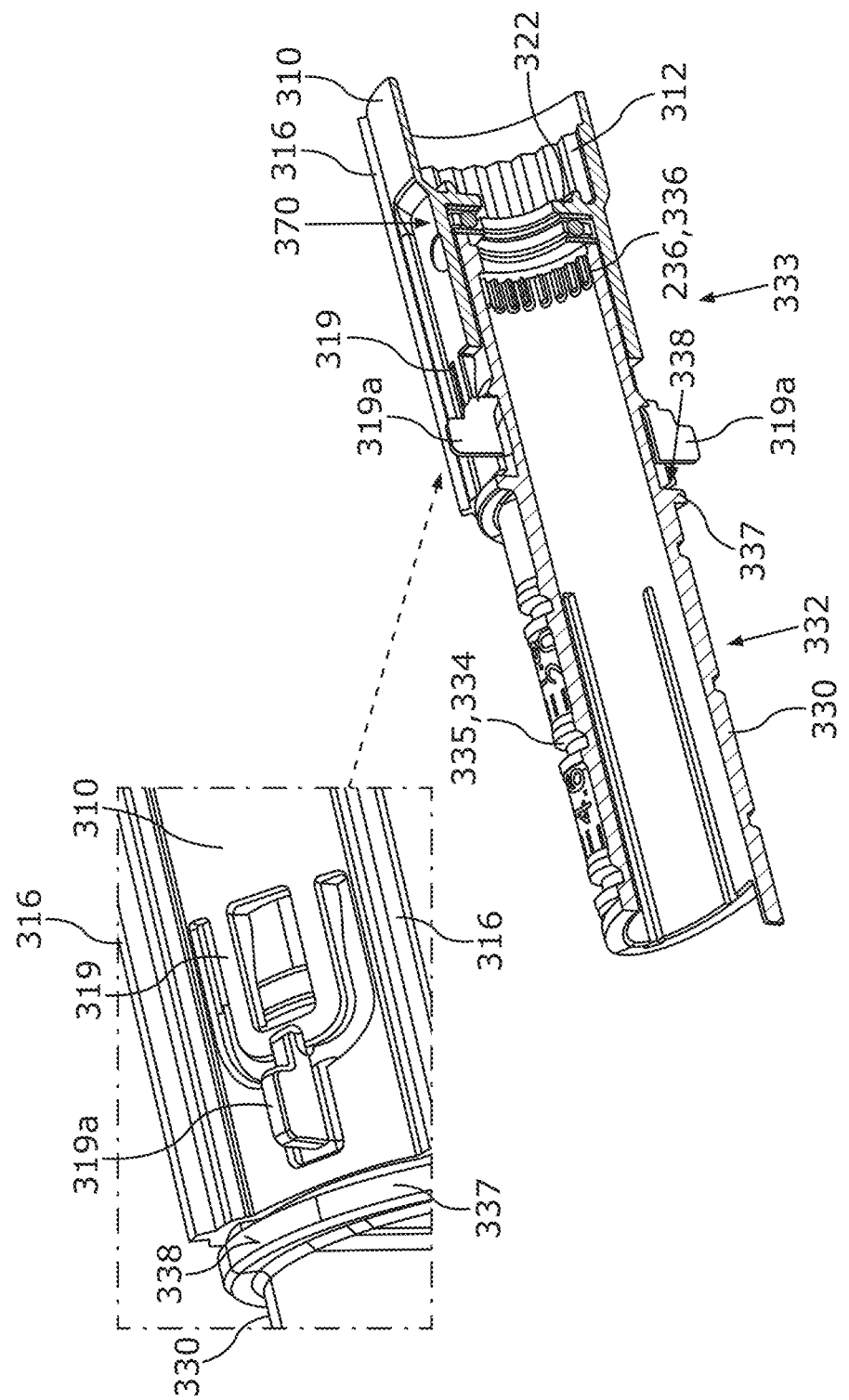
FIG. 49 is a cross sectional view of the further alternative embodiment of the inner housing and the alternative embodiment of the dose selector member.

FIG. 48 to FIG. 49 show an alternative connection between an alternative embodiment of the inner housing 180 and an alternative embodiment of the dose selector member 310. As far as no differences are described or apparent from the Figures, the alternative embodiments of the inner housing 180 and/or the alternative embodiments of the dose selector member 310 are configured as it is described in connection with the other embodiments of the inner housing 180 and the dose selector member 310 according to the present disclosure.

The dose selector member 310 shown in FIG. 48 and FIG. 49 comprises longitudinal protrusions 319a on two of the flexible members 319, wherein the longitudinal protrusions 319a project radially outward into longitudinal slots 198 within the inner housing 180. As can be seen from FIG. 48, the longitudinal slots 198 that receive the protrusions 319a have a recess 193 at their distal end. The recess 193 of each slot 198 is configured to receive the protrusion 319a that is located within the respective slot 198 when the dose selector member 310 is fully extended from the inner housing 180 in the distal direction, for example upon setting the maximum settable dose. This is further illustrated in FIG. 50, which shows the inner housing 180, the dose selector member 310 and the dosing member 330 with no dose set, and FIG. 51, which shows the inner housing 180, the dose selector member 310 and the dosing member 330 with the maximum dose set.

When the maximum dose is set, the stopping surfaces 338 of the maximum dose stops 337 abut against the limiting surfaces 192 of the maximum stop features 190. Furthermore, the radial protrusions 198*a* are received within the recesses 193. With the embodiments of the drug delivery device 200 shown in FIGS. 48 to 51, the inner housing 180 comprises two maximum stop features 190 that are located opposite to each other with respect to the longitudinal axis 207. Instead of two further maximum stop features 190, the inner housing 180 comprises two longitudinal slots 198 that have the recesses 193 at the distal end. The longitudinal slots 198 with the recesses 193 are also located opposite to each other with respect to the longitudinal axis 207. In the circumferential direction, the inner housing 180 alternately comprises longitudinal slots 198 that feature the limiting surfaces 192 and longitudinal slots 188 that feature the recesses 193.

The radial protrusions 319*a* and the recesses 193 can serve as a further maximum dose stop mechanism that is disposed between the dose selector member 310 and the inner housing 180 and that limits axial movement of the dosing member 330 and the dose selector member 310 upon having set the maximum settable dose. Alternatively or additionally, they can provide a locking device or means that prevents detachment of the dose selector member 310 from the housing 210 after assembly of the drug delivery device 200. For example, the radial protrusions 319*a* and the recesses 193 can be configured in a way that they do not touch each other upon engagement between the stopping surface 338 and the limiting surfaces 192 but only touch upon further forceful movement of the dose selector member 310 in the distal direction. Alternatively, the radial protrusions 319*a* and the recesses 193 can be configured to touch essentially simultaneously with the stopping surface 338 touching the limiting surfaces 192.

Figure 50:
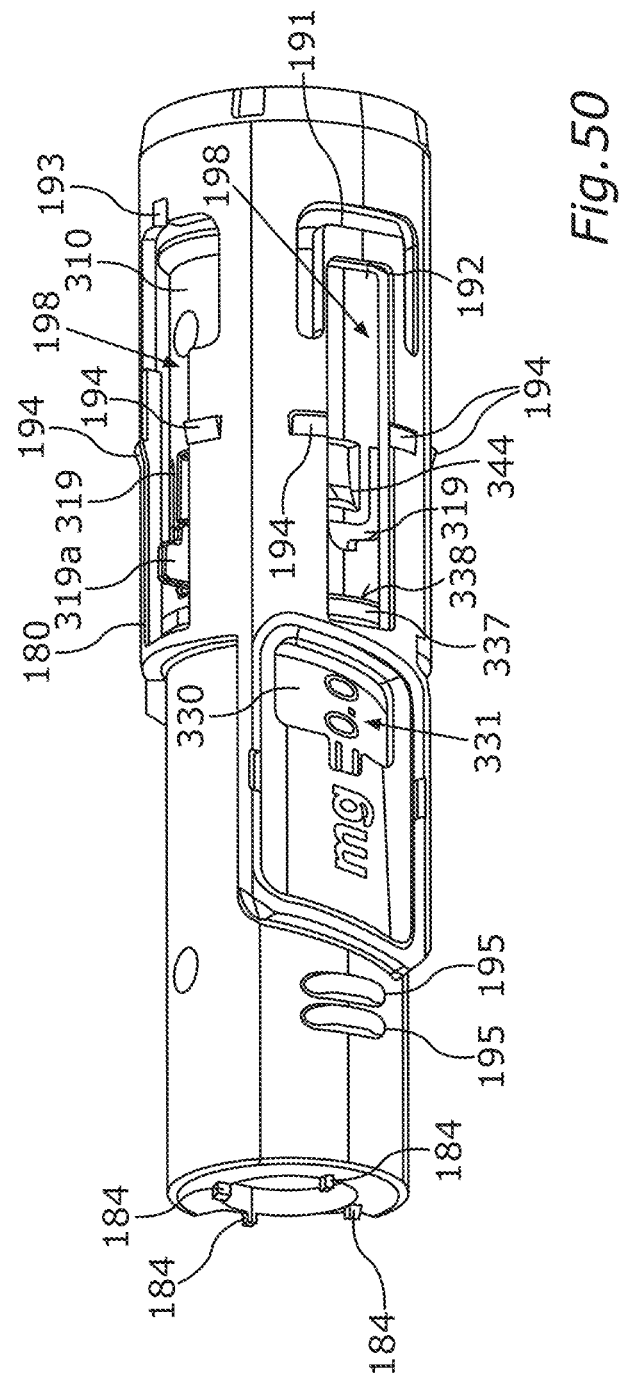
FIG. 50 is the alternative embodiments of the inner housing, the dose selector member and the dosing member with no dose set.

As can be seen from FIGS. 49 and 50, an inner housing 180 that is configured to receive the alternative embodiments of the dose selector member 310 having the radial protrusions 319*a* can also have four of the tappets 183 and be configured to be used in a drug delivery device 200 that features the alternative embodiment of the coupling part 130 shown in FIGS. 46 and 47. Alternatively, such an inner housing 118 can also feature only two of the tappets 184 and be configured to be used with the coupling part 130 described in connection with FIGS. 27 to 33.

Figure 51:
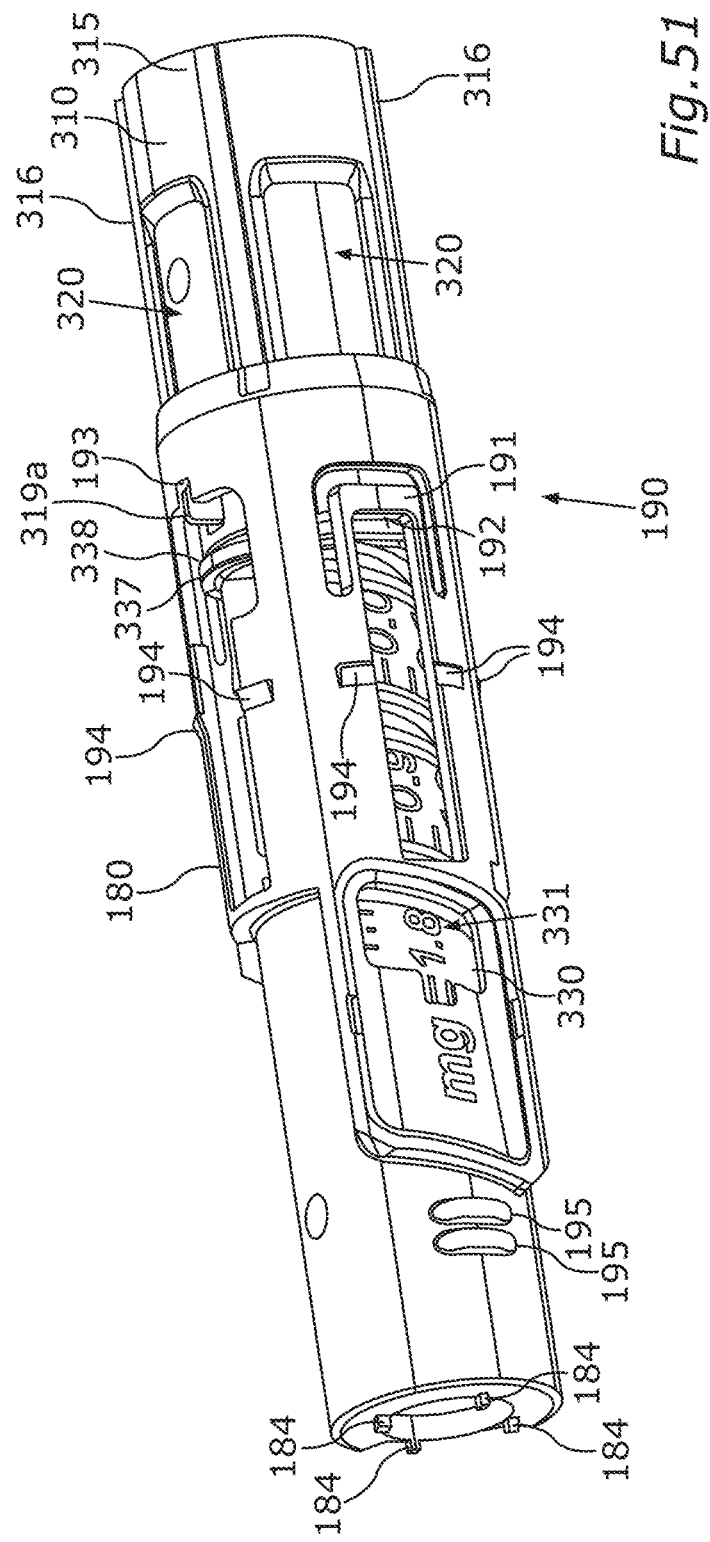
FIG. 51 is an alternative embodiment of the clutch member.

As further can be seen from FIG. 51, the dose definition mechanism 232 of the drug delivery device 200 having the alternative embodiments of the dose selector member 310 and the inner housing 180 is exemplarily configured as it is described in connection with FIGS. 36 and 37 for the first drug delivery device 220 that is configured to expel a maximum dose of the active pharmaceutical ingredient of 1.8 mg.

As it has been described in connection with the first, second and third drug delivery device 220, 222, 225, the clutch mechanisms 234 of the individual drug delivery devices 220, 222, 225 of the individual sets can define a different number of rotational coupling positions in which the first part 235 of the clutch mechanism 234 can be closed to rotationally couple the clutch member 270 to the dosing member 330. These rotational coupling positions are defined by the circumferential positions of the clutch elements 273, 336.

An angular spacing between the rotational coupling positions corresponds to an angular spacing between the dose positions that are settable by rotating the dose setting member 290. With the type of drug delivery device 200 described in connection with FIGS. 1 to 37 and 44 to 51, the angular spacing between the rotational coupling positions equals the angular spacing between the dose positions. In general, these positions can correspond in a way that the angular spacing between the dose positions is a multiple of the angular spacing between the coupling positions. For example, depending on the circumferential positions of the dose stops 35*a* on the inner surface of the dose selector member 35 of the further drug delivery device 10, the angular spacing between the dose positions defined by the dose stops 35*a* can be an integer multiple of the rotational coupling positions defined by the clutch elements 34*a* on the connector 34 and the clutch elements 33*a* on the snap element 33.

The embodiment of the clutch member 270 of the drug delivery device 200 shown in FIGS. 16 and 17 comprises one clutch element 273 for each rotational coupling position. So, in principle, a single clutch element 336 on the dosing member 330 would suffice to define the rotational coupling positions. With alternative embodiments of the clutch member 270, the number of clutch elements 273 can also differ from the number of rotational coupling positions. For example, a number of clutch elements 273 can be smaller than the number of rotational coupling positions per revolution of the dose setting member 290. The number of clutch elements 273 can thereby be smaller by at least one, at least two, such as by one or two, or by more clutch elements 273.

The embodiment of the dosing member 330 shown in FIG. 20 comprises one clutch element 336 for each rotational coupling position. So, in principle, a single clutch element 273 on the clutch member 270 would suffice to define the rotational coupling positions. With alternative embodiments of the dosing member 330, the number of clutch elements 336 can also differ from the number of rotational coupling positions. For example, the number of clutch elements 336 can be smaller than the number of rotational coupling positions per revolution of the dose setting member 290. The number of clutch elements 336 can thereby be smaller by at least one, by at least two, such as by one or two, or by more clutch elements 336.

Figure 52:
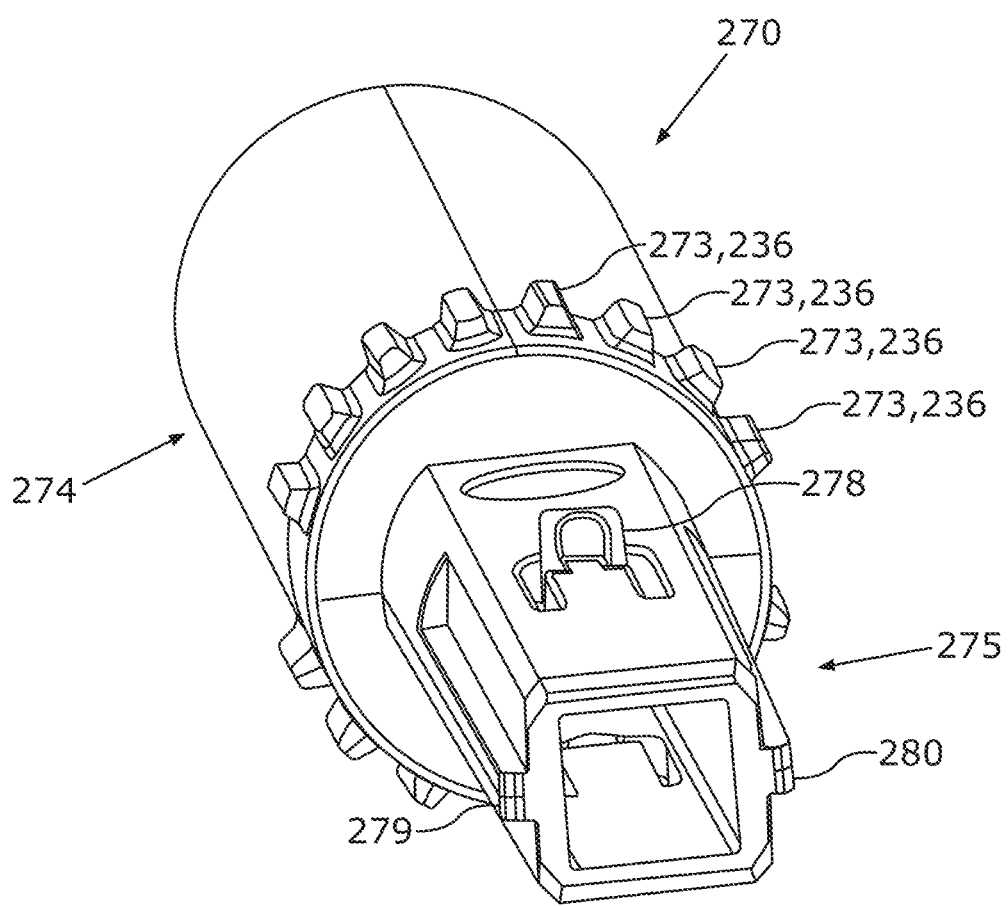
FIG. 52 is the alternative embodiments of the inner housing, the dose selector member and the dosing member with the maximum dose set.

FIG. 52 shows an alternative embodiment of the clutch member 270 of the drug delivery device 200. As long as no differences are described or apparent from the Figures, the alternative embodiment of the clutch member 270 is configured as it is disclosed in connection with the clutch member 270 described above.

A number of clutch elements 273 of the alternative embodiments of the clutch member 270 is by two smaller than the number of rotational coupling positions. The clutch elements 273 are located next to each other in two groups, wherein each group comprises the same number of clutch elements 273, that is, exemplarily, eight clutch elements 273, and wherein the clutch elements 273 of the individual groups are equally spaced apart from each other. In the gaps between the two groups, a ninth clutch element 273 is missing. The two groups of clutch elements 273 are circumferentially spaced apart from each other by twice the distance between the clutch elements 273 of the individual groups.

The drug delivery devices 10, 200, 220, 222, 225 according to the present disclosure can comprise a balancing weight. The balancing weight can be located at a position offset from the longitudinal axis 207 of the device 10, 200, 220, 222, 225, so that a position of the center of mass of the device 10, 200, 220, 222, 225 is shifted away from the longitudinal axis 207 towards the outer circumferential shell of the device 10, 200, 220, 222, 225. This prevents rolling of the device 10, 200, 220, 222, 225 when it is placed on a flat surface.

Figure 53:
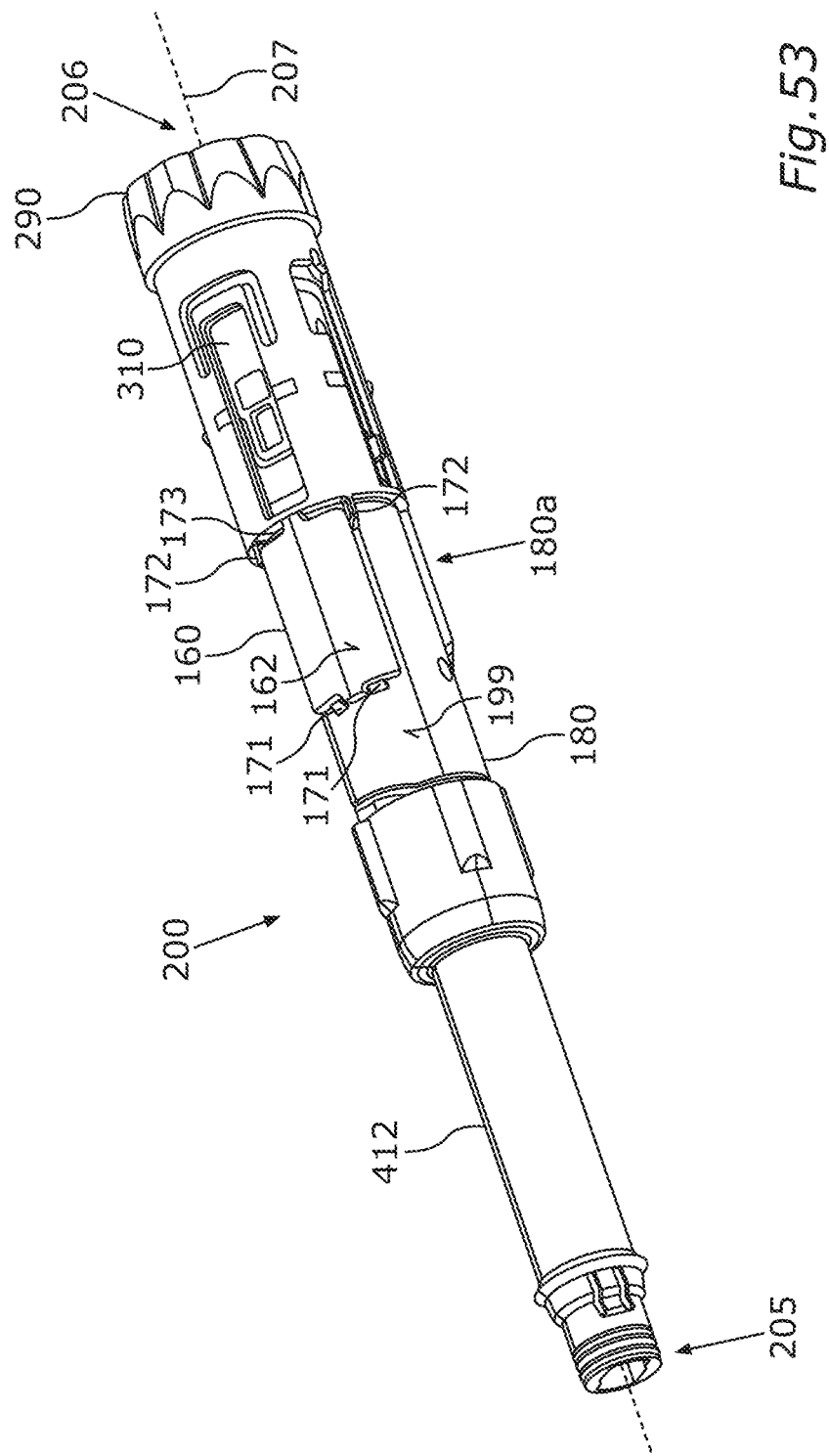
FIG. 53 is a further alternative embodiment of the inner housing with a balancing weight located on an outer surface of the inner housing.
Figure 54:
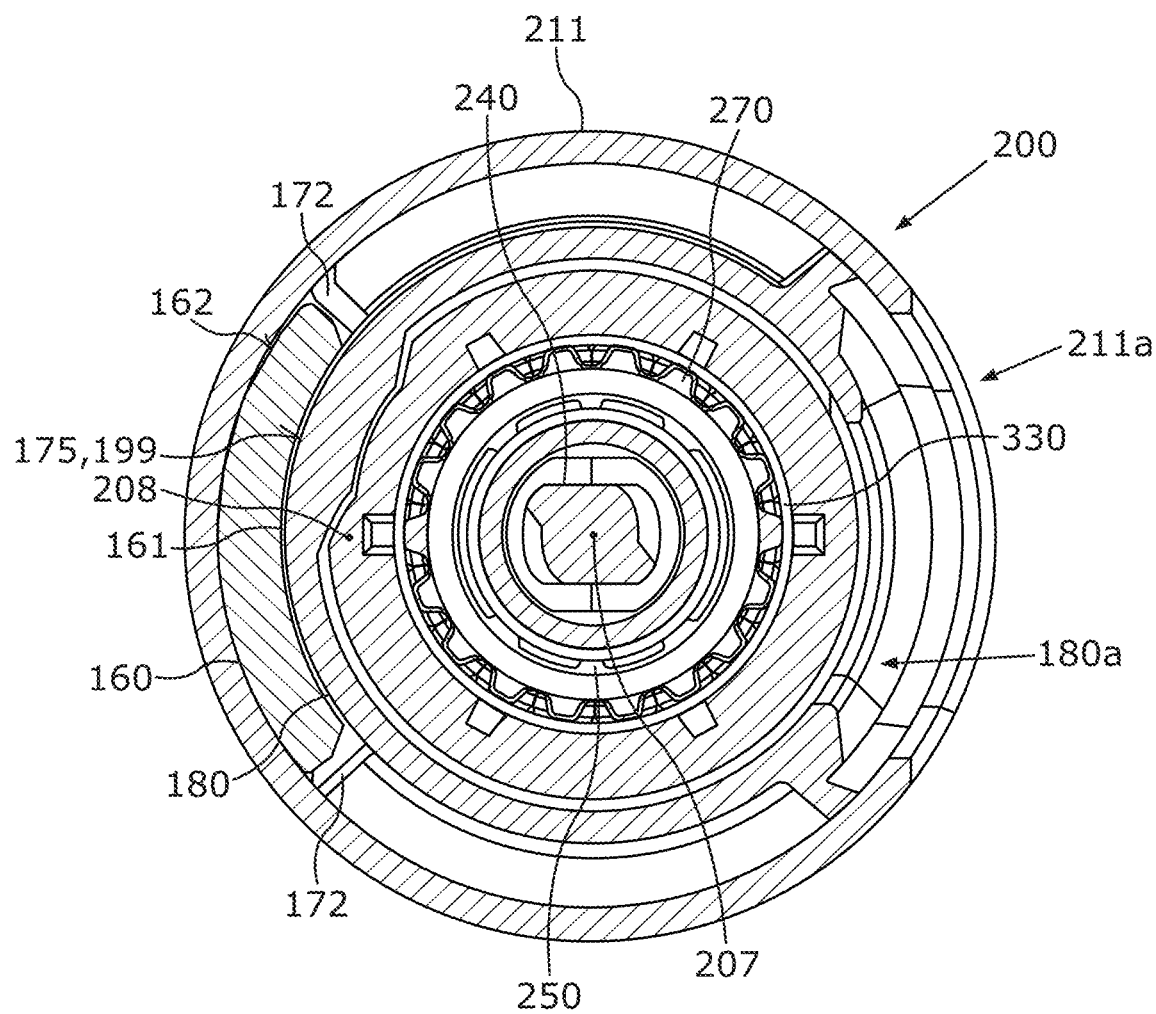
FIG. 54 is a radial cross sectional view of perpendicular to the longitudinal axis through the drug delivery device with the balancing weight.

FIG. 53 shows a perspective view of the drug delivery device 200 that is equipped with such a balancing weight 160 and FIG. 54 shows a radial cut perpendicular to the longitudinal axis 207 through the device 200 and the balancing weight 160. In FIG. 53, the outer housing 211 of the drug delivery device 200 has been omitted. The balancing weight 160 is located within the housing 210 of the device 200, namely within the outer housing 211. It is thereby placed between the inner housing 180 and the outer housing 211, as well as between the dosing mechanism 230 and the outer housing 211.

The balancing weight 160 is placed on an outer surface 199 of the inner housing 180. It has a curved bottom surface 161, which faces towards the longitudinal axis 207, and a curved top surface 162, which faces away from the longitudinal axis 207. The bottom surface 161 forms a segment of a circular cylindrical shell with a rotational axis that coincides with the longitudinal axis 207. Likewise, the top surface 162 forms a segment of a circular cylindrical shell with a rotational axis that coincides with the longitudinal axis 207. The bottom and top surfaces 161, 162 are orientated parallel to each other.

Figure 55:
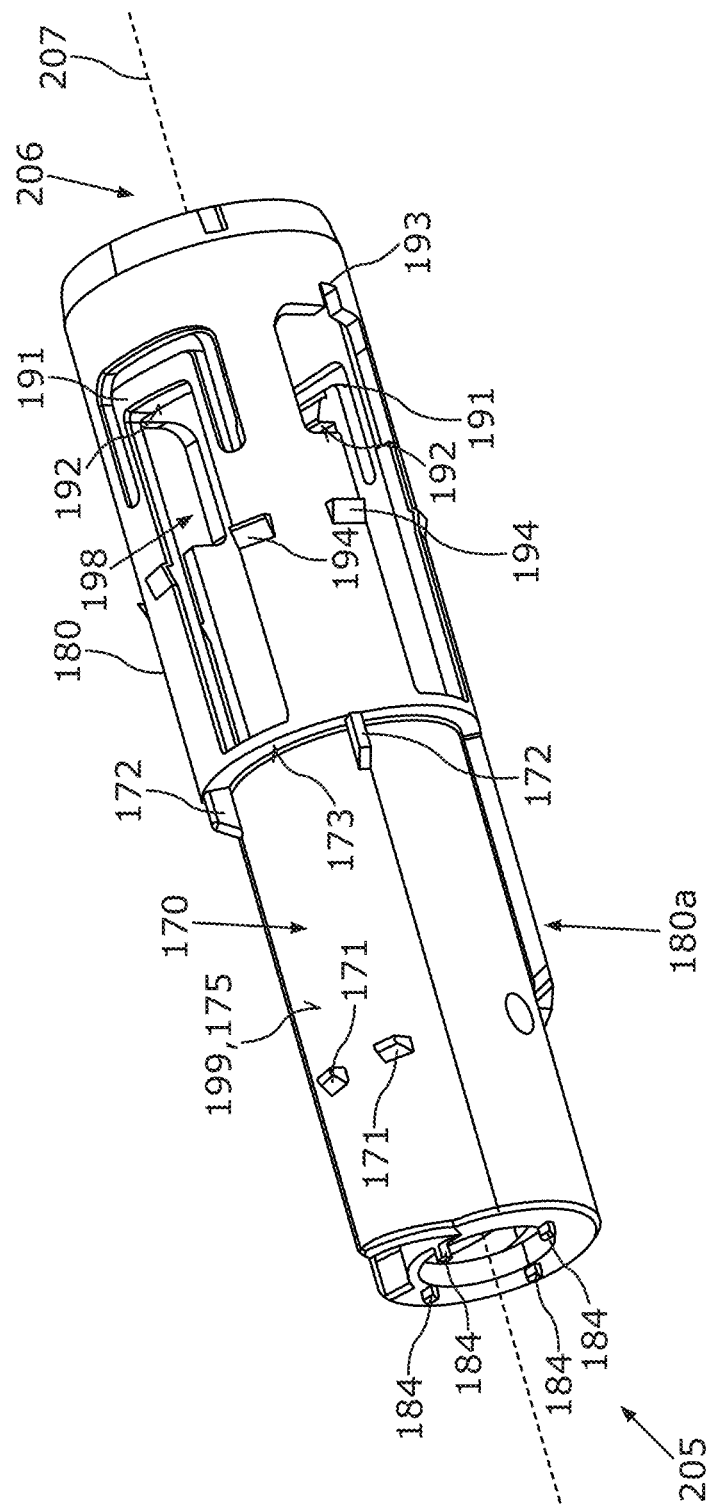
FIG. 55 is the alternative embodiment of the inner housing.

The balancing weight 160 is laid in a seat 170, which is formed on the outer surface 199 of the inner housing 180 and which is, inter alia, depicted in FIG. 55. The seat 170 comprises a support surface 175, which carries the balancing weight 160 and against which the bottom surface 161 of the balancing weight 160 rests. The support surface 175 is formed by the outer surface 199 of the inner housing 180. Furthermore, the seat 170 comprises at least one, namely two, first longitudinal stop elements 171 that delimit the seat 170 towards the proximal end 205 and a second longitudinal stop element 173 that delimits the seat 170 towards the distal end 206. To prevent rotation of the balancing weight 160 in the circumferential direction, the seat 170 comprises two circumferential stop elements 172 that limit the seat 170 in the circumferential direction.

The first longitudinal stop elements 171 are configured as protrusions located on the outer surface 199 of the inner housing 180. The first longitudinal stop elements 171 are spaced apart from each other in the circumferential direction and located at the same axial position along the longitudinal axis 207. The first longitudinal stop elements 171 have an elongated shape that is orientated perpendicular to the longitudinal axis 207.

The second longitudinal stop element 173 is configured as a protrusion that forms a step in the outer surface 199 of the inner housing 180. The second longitudinal stop element 173 runs perpendicular to the longitudinal axis 207 and forms a radial surface that is orientated perpendicular to the longitudinal axis 207.

The circumferential stop elements 172 are configured as individual protrusions located on the outer surface 199 of the inner housing 180. They are placed at the distal end of the seat 170. Furthermore, they are configured as protrusions that extend in the proximal direction from the second longitudinal stop element 173. The longitudinal stop elements 172 have an elongated shape that is orientated parallel to the longitudinal axis 207.

As can be seen from FIG. 54, the seat is covered by the outer housing 211. The balancing weight 160 is configured to abut with its top surface 162 against an inner surface of the outer housing 211. The balancing weight 160 is sandwiched between the inner housing 180 and the outer housing 211. The covered seat 170 forms a cavity in which the balancing weight 160 is inserted. Thereby, the balancing weight 160 is only held in place by the stop elements 171, 172, 173, the support surface 175 and the inner surface of the outer housing 211.

As further can be seen from FIG. 54, the balancing weight 160 causes a center of mass 208 of the drug delivery device 200 to be located away from the longitudinal axis 207 of the device 200 towards the balancing weight 160. The center of mass 208 is located between the longitudinal axis 207 and the balancing weight 160. Furthermore, a distance between the balancing weight 160 and the center of mass 208 is smaller than a distance between the center of mass 208 and the longitudinal axis 207.

The balancing weight 160 and the window 211a in the outer housing 211, as well as the balancing weight 160 and the window 180a in the inner housing 180 are located at different angular positions with respect to the longitudinal axis 207. In the exemplary embodiment of FIG. 54, the balancing weight 160 and the windows 211a, 180a are located on angular positions that differ by 180° and thus correspond to opposite sides of the longitudinal axis 207.

The contact surface of the drug delivery device 200, which comprises all surface elements of the drug delivery device 200 that touch a planar surface when rolling the drug delivery device 200 over the surface has a circular cylindrical outer surface that lacks protrusions that would inhibit rolling of the housing 210 when being placed on a flat surface. Due to the balancing weight 160, the drug delivery device 200 will rotate on a flat surface until it assumes a stable position and the center of mass 280 is located between the surface and the longitudinal axis 207.

In the stable position, the windows 180a, 211a are located on the upper side of the drug delivery device 200 that faces away from the surface that the drug delivery device 200 is placed on. With other embodiments of the device 200 and other placings of the balancing weight 160, the windows 180a, 211a could also be located on another side of the drug delivery device 200, for example on a lateral side.

Figure 56:
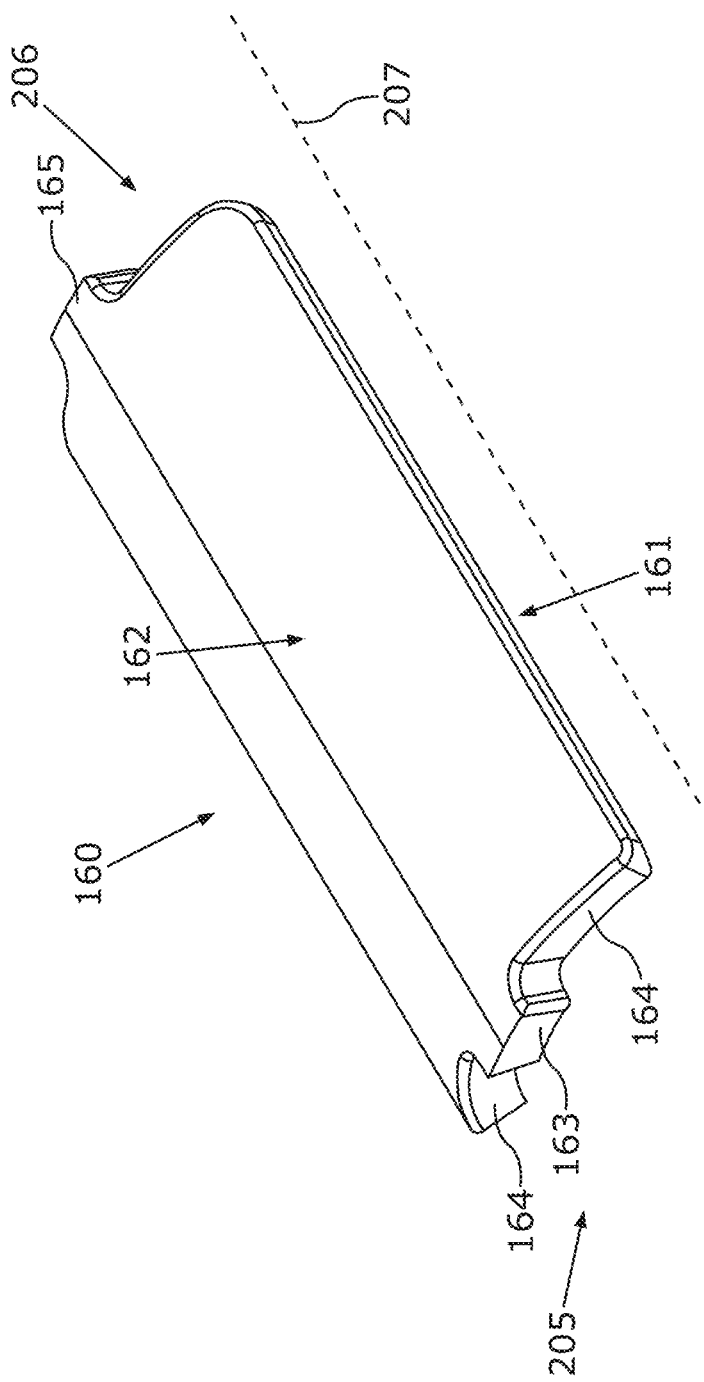
FIG. 56 is the balancing weight.

FIG. 56 shows a perspective view of the balancing weight 160. It is configured as a metal part and has a higher density than the plastic parts of the dosing mechanism 230 and the inner housing 180.

The balancing weight 160 is curved around the longitudinal axis 207 of the drug delivery device 200. It is symmetrical with respect to its center plane, which is orientated perpendicular to the longitudinal axis 207.

The balancing weight 160 has a proximal protrusion 163 at its proximal end and a distal protrusion 165 at its distal end. When being inserted into the seat 170, the proximal protrusion 163 is placed in between the first longitudinal stop elements 171. Two front faces 164 of the balancing weight 160 that radially extend from the proximal protrusion 163 and which are set back along the longitudinal axis 207 with respect to the proximal protrusion 163 are configured to abut against the first longitudinal stop elements 171. The distal protrusion 165 is configured to abut against the second longitudinal stop element 173. A width of the balancing weight 160 perpendicular to the longitudinal axis 207 is adapted to allow the balancing weight 162 being placed in between the circumferential stop elements 172.

Figure 57:
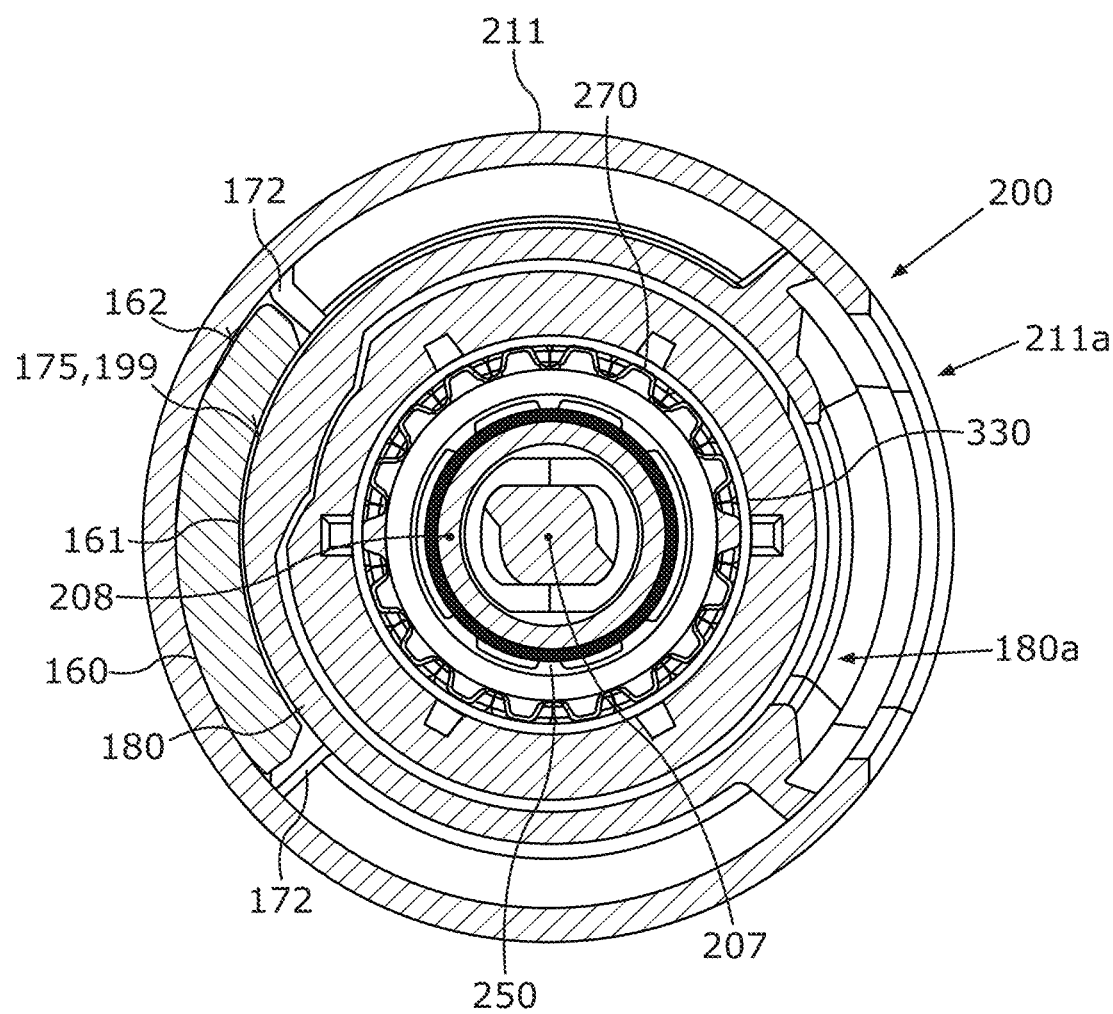
FIG. 57 is a radial cross sectional view of perpendicular to the longitudinal axis through an alternative embodiment of the drug delivery device with the balancing weight.

With other embodiments, the distance between the balancing weight 160 and the center of mass 208 can also be smaller than the distance between the center of mass 208 and the longitudinal axis 207, as can be seen from FIG. 57, which shows a radial cut perpendicular to the longitudinal axis 207 through an alternative embodiment of the drug delivery device 200 with the balancing weight 160. Positioning the center of mass 208 at a smaller distance from the longitudinal axis 207 than from the balancing weight 160 allows to use a comparatively small balancing weight 160 while still shifting the center of mass away from the longitudinal axis 207.

The sectional views of FIGS. 54 and 57 only schematically depict the radial position of the center of mass 208. With the drug delivery device 200, the longitudinal position of the center of mass 208 can not be located within the sectional plane depicted in FIGS. 54 and 57 but in other cross-sectional planes. The longitudinal position of the center of mass 208 can, for example, be positioned distally from the longitudinal center of the window 211a within the outer housing 211 along the longitudinal axis 207 or it can be positioned proximally from the longitudinal center of the window 211a within the outer housing 211 along the longitudinal axis 207.

The present disclosure is also directed at the following embodiments of a drug delivery device:

1. A drug delivery device (10, 200, 220, 222, 225) with an elongate, for example generally cylindrical, housing (3, 43, 210, 221, 223, 226) extending along a longitudinal axis (207) between a distal end (206) and a proximal end (205),
   wherein the housing (3, 43, 210, 221, 223, 226) is, for example, configured as a generally cylindrical housing (3, 43, 210, 221, 223, 226),
   wherein the drug delivery device (10, 200, 220, 222, 225) comprises a balancing weight (160) located within the housing (3, 43, 210, 221, 223, 226),
   wherein a center of mass (208) of the drug delivery device (10, 200, 220, 222, 225) is located radially offset from the longitudinal axis (207) in a radial direction of the balancing weight (160).

2. The drug delivery device (10, 200, 220, 222, 225) according to embodiment 1,
   wherein the center of mass (208) is located between the balancing weight (160) and the longitudinal axis (207).

3. The drug delivery device (10, 200, 220, 222, 225) according to one of the preceding embodiments,
   wherein a distance between a radial position of the balancing weight (160) and a radial position of the center of mass (208) is smaller than a distance between the radial position of the center of mass (208) and the longitudinal axis (207).

4. The drug delivery device (10, 200, 220, 222, 225) according to one of the preceding embodiments,
   wherein the balancing weight (160) and a window (3a, 180a, 211a) of the housing (3, 43, 210, 221, 223, 226) for showing an optical marker (40, 331) indicating a set dose are located at different angular positions with respect to the longitudinal axis (207), for example at angular positions that differ by 180°.

5. The drug delivery device (10, 200, 220, 222, 225) according to one of the preceding embodiments,
   wherein the balancing weight (160) is configured as a separate member of the drug delivery device (10, 200, 220, 222, 225).

6. The drug delivery device (10, 200, 220, 222, 225) according to one of the preceding embodiments,
   wherein the balancing weight (160) is made from metal.

7. The drug delivery device (10, 200, 220, 222, 225) according to one of the preceding embodiments,
   wherein a material of the balancing weight (160) has a higher density than a material of a majority of members of a dosing mechanism (230) of the drug delivery device (10, 200, 220, 222, 225).

8. The drug delivery device (10, 200, 220, 222, 225) according to one of the preceding embodiments,
   wherein the balancing weight (160) is located at an inside surface of a shell of the housing (3, 43, 210, 221, 223, 226) of the drug delivery device (10, 200, 220, 222, 225).

9. The drug delivery device (10, 200, 220, 222, 225) according to one of the preceding embodiments,
   wherein the balancing weight (160) is configured separate from members of a dosing mechanism (230) of the drug delivery device (10, 200, 220, 222, 225).

10. The drug delivery device (10, 200, 220, 222, 225) according to embodiment 9,
    wherein the balancing weight (160) is located between the housing (3, 43, 210, 221, 223, 226) and the dosing mechanism (230).

11. The drug delivery device (10, 200, 220, 222, 225) according to one of the preceding embodiments,
    wherein the housing (3, 43, 210, 221, 223, 226) comprises an outer housing (211), wherein the drug delivery device (10, 200, 220, 222, 225) comprises an inner housing (180),
    wherein the inner housing (180) is permanently rotationally and/or axially fixed with respect to the outer housing (211),
    wherein the balancing weight (160) is located between the outer housing (211) and the inner housing (180).

12. The drug delivery device (10, 200, 220, 222, 225) according embodiment 11,
    wherein the balancing weight (160) rests on an outer surface (199) of the inner housing (3, 43, 210, 221, 223, 226).

13. The drug delivery device (10, 200, 220, 222, 225) according to one of the preceding embodiments,
    wherein the balancing weight (160) is axially and/or rotationally fixed with respect to the housing (3, 43, 210, 221, 223, 226).

14. The drug delivery device (10, 200, 220, 222, 225) according embodiment 13,
    wherein the balancing weight (160) is received in a seat (170) that is configured to axially and/or rotationally fix the balancing weight (160) with respect to the housing (3, 43, 210, 221, 223, 226).

15. The drug delivery device (10, 200, 220, 222, 225) according to embodiment 14,
    wherein the seat (170) comprises longitudinal stop elements (171, 173) that prevent movement of the balancing weight (160) along the longitudinal axis (207).

16. The drug delivery device (10, 200, 220, 222, 225) according to one of embodiments 14 and 15,
    wherein the seat (170) comprises circumferential stop elements (172) that prevent movement of the balancing weight (160) around the longitudinal axis (207).

17. The drug delivery device (10, 200, 220, 222, 225) according to one of embodiments 15 and 16,
    wherein the stop elements (171, 172, 173) are configured as protrusions on a surface (199) of the housing (3, 43, 210, 221, 223, 226).

18. The drug delivery device (10, 200, 220, 222, 225) according to one of embodiments 14 to 17 and embodiment 12,
wherein the seat (170) is provided at the outer surface (199) of the inner housing (3, 43, 210, 221, 223, 226).
19. The drug delivery device (10, 200, 220, 222, 225) according to one of embodiments 14 to 18,
wherein the housing (3, 43, 210, 221, 223, 226), such as an outer housing (211) of the housing (3, 43, 210, 221, 223, 226), is configured to cover the seat (170) in a radial direction perpendicular to the longitudinal axis (207) to prevent radial movement of the balancing weight (160).
20. The drug delivery device (10, 200, 220, 222, 225) according to one of the preceding embodiments,
wherein the balancing weight (160) has a bottom surface (161), such as a curved and/or concave bottom surface,
wherein the bottom surface (161) radially faces towards the longitudinal axis (207),
wherein the bottom surface (161) is formed complementary to a surface of one or more members of the drug delivery device (10, 200, 220, 222, 225) located between the longitudinal axis (207) and the balancing weight (160).
21. The drug delivery device (10, 200, 220, 222, 225) according to one of the preceding embodiments,
wherein the balancing weight (160) has a top surface (162), such as a curved and/or convex top surface,
wherein the top surface (162) radially faces away from the longitudinal axis (207),
wherein the top surface (162) is formed complementary to one or more inner surfaces of the housing (3, 43, 210, 221, 223, 226) of the drug delivery device (10, 200, 220, 222, 225).
22. The drug delivery device (10, 200, 220, 222, 225) according to one of the preceding embodiments,
wherein a shape of the balancing weight (160) is symmetrical with respect to a centre plane that is orientated perpendicular to the longitudinal axis (207).

The present disclosure is also directed at the following embodiments of a drug delivery device
1. Drug delivery device having
a housing with a longitudinal axis,
a dose setting member that is actuatable by a user and rotatable around the longitudinal axis to set a dose to be delivered by the drug delivery device,
a piston rod that is configured to be axially advanced in a proximal direction to deliver the set dose, and
a dosing member for defining the axial advancement of the piston rod upon delivery of the set dose,
wherein the dosing member is axially movable along the longitudinal axis and rotationally movable around the longitudinal axis during dose setting,
wherein the dosing member is rotationally fixed to the dose setting member during dose setting,
wherein the dosing member comprises a maximum dose stop,
wherein the maximum dose stop is configured to engage with a maximum stop feature to limit movement of the dosing member with respect to the housing upon setting a maximum dose,
wherein the maximum stop feature is provided at the housing.
2. The drug delivery device according to embodiment 1,
wherein the dosing member is rotationally movable with respect to the dose setting member during dose delivery.
3. The drug delivery device according to one of the preceding embodiments,
wherein the dosing member is configured to perform more than one full rotation, for example two full rotations, with respect to the housing during dose setting,
wherein, for example, the dosing member is configured to perform two full rotations to set a maximum settable dose.
4. The drug delivery device according to one of the preceding embodiments,
wherein the dosing member is threadedly connected to the housing, for example via an outer thread provided on the dosing member and a corresponding inner thread provided on the housing.
5. The drug delivery device according to one of the preceding embodiments,
wherein the dosing member is rotatable with respect to the housing during both dose setting and dose delivery.
6. The drug delivery device according to one of the preceding embodiments,
wherein the maximum dose stop comprises a stopping surface that is configured to axially abut the maximum stop feature of the housing upon setting the maximum dose.
7. The drug delivery device according to embodiment 6,
wherein the stopping surface is orientated perpendicular to the longitudinal axis.
8. The drug delivery device according to one of embodiments 6 and 7,
wherein the stopping surface is an annular surface surrounding the longitudinal axis.
9. The drug delivery device according to one of the preceding embodiments,
wherein the maximum dose stop protrudes from an outer surface of the dose setting member and/or
wherein the maximum stop feature protrudes from an inner surface of the housing.
10. The drug delivery device according to one of the preceding embodiments,
wherein the maximum dose stop is spaced apart from a distal end of the dosing member.
11. The drug delivery device according to one of the preceding embodiments,
wherein the maximum stop feature of the housing has a limiting surface that is orientated perpendicular to the longitudinal axis,
wherein the maximum dose stop engages with the limiting surface upon setting the maximum dose.
12. The drug delivery device according to one of the preceding embodiments,
wherein the maximum stop feature of the housing is provided on a flexible element that is configured to snap over the maximum dose stop of the dosing member upon assembly of the drug delivery device.
13. The drug delivery device according to embodiment 12,
wherein the flexible element rests against a backing element, such as an outer housing that surrounds an inner housing having the flexible element, after assembly of the drug delivery device to prevent disengagement of the maximum stop feature from the maximum dose stop.

14. The drug delivery device according to one of the preceding embodiments,
    wherein the dosing member is configured as a dose indication member that provides a visual indication of the set dose to a user, for example via corresponding markings on an outer surface of the dose setting member.
15. The drug delivery device according to one of the preceding embodiments,
    wherein the dose setting member is configured to axially move with respect to the housing together with the dosing member during dose setting.
16. The drug delivery device according to one of the preceding embodiments,
    wherein the dosing member comprises a zero dose stop,
    wherein the zero dose stop is configured to engage with a zero stop feature to limit movement of the dosing member with respect to the housing upon the dosing member reaching a zero dose position,
    wherein the zero stop feature is provided at the housing.
17. The drug delivery device according to embodiment 16,
    wherein the zero dose stop engages with the zero stop feature in a contact plane that is angled with respect to a radial plane perpendicular to the longitudinal axis, wherein, for example, the contact plane is orientated perpendicular to the radial plane.
18. The drug delivery device according to one of embodiments 16 to 17,
    wherein the zero dose stop of the dosing member comprises a stop surface that is configured to abut against a corresponding stop surface of the housing.
19. The drug delivery device according to one of embodiments 16 to 18,
    wherein the zero dose stop is provided at a proximal end of the dosing member and/or
    wherein the zero stop feature is provided at a proximal end of a housing cavity of the housing.
20. The drug delivery device according to one of embodiments 16 to 19,
    wherein the zero stop feature and the maximum stop feature are provided at the same structural element of the housing, for example at an inner housing member.
21. The drug delivery device according to embodiment 20,
    wherein the structural element comprises a dose setting thread that threadedly engages with the dosing member.
22. The drug delivery device according to one of embodiments 20 and 21,
    wherein the structural element comprises a drive thread that threadedly engages with a driver of the drug delivery device,
    wherein the driver is coupled to the piston rod during dose delivery to axially advance the piston rod upon axial movement of the driver.
23. The drug delivery device according to one of the preceding embodiments,
    wherein the drug delivery device comprises a dose definition mechanism for defining rotational dose positions of the dose setting member with respect to the housing,
    wherein the dose setting member is connected to the housing via a dose selector,
    wherein the dose selector is rotationally fixed and axially movable with respect to the housing,
    wherein the dose definition mechanism acts between the dose selector and the dose setting member.
24. The drug delivery device according to embodiment 23,
    wherein the dose selector is axially fixed with respect to the dosing member.
25. The drug delivery device according to one of embodiments 23 and 24,
    wherein the dose selector is connected to the housing via a connection that allows the dose selector to be mounted to the housing only in rotational orientations that ensure that the dose setting member is set to a dose position upon engagement of the maximum dose stop with the maximum stop feature,
    wherein, for example, the connection allows a single rotational orientation only.
26. The drug delivery device according to embodiment 25,
    wherein the connection comprises a splined connection that allows axial movement and prevents rotational movement of the dose selector with respect to the housing,
    wherein the splined connection comprises a set of coding splines wherein the coding splines have respective dimensions that differ from each other, for example in width and/or height.
27. The drug delivery device according to embodiment 26,
    wherein the splined connection comprises a single coding spline that differs from the remaining splines of the connection.
28. The drug delivery device according to one of the preceding embodiments,
    wherein the dosing member is coupled to the piston rod via an advancement mechanism that translates axial movement of the dosing member into the axial advancement of the piston rod during dose delivery so that the axial movement of the dosing member during dose delivery causes the piston rod to axially advance in the proximal direction.
29. The drug delivery device according to embodiment 28,
    wherein the advancement mechanism is configured as a gearing mechanism that reduces the axial movement of the dosing member to a smaller axial advancement of the piston rod.
30. The drug delivery device according to one of embodiments 28 to 29,
    wherein the piston rod is rotationally fixed to the housing,
    wherein the advancement mechanism comprises a nut that is coupled between the piston rod and the dosing member,
    wherein the nut is threadedly connected to the piston rod,
    wherein the nut is rotationally fixed with respect to the dosing member and rotatable with respect to the housing during dose setting,
    wherein the nut is rotatable with respect to the dosing member and rotationally fixed with respect to the housing during dose delivery.
31. The drug delivery device according to embodiment 30,
    wherein the advancement mechanism comprises a driver that is coupled between the nut and the dosing member, wherein the driver is rotationally fixed to the dosing member and axially movable with respect to the dose setting member during both dose setting and dose delivery, wherein the driver is threadedly coupled to the housing, wherein the driver is configured to engage with the nut during dose delivery to axially advance the nut and the piston rod upon being rotated by the dosing member.

32. Drug delivery device having
 a housing with a longitudinal axis,
 a dose setting member that is actuatable by a user and rotatable around the longitudinal axis to set a dose to be delivered by the drug delivery device,
 a piston rod that is configured to be axially advanced in a proximal direction to deliver the set dose, and
 a dosing member for defining the axial advancement of the piston rod upon delivery of the set dose,
 wherein the dosing member is axially movable along the longitudinal axis and rotationally movable around the longitudinal axis during dose setting,
 wherein the dosing member is rotationally fixed to the dose setting member during dose setting,
 wherein the dosing member comprises a zero dose stop,
 wherein the zero dose stop is configured to engage with a zero stop feature to limit movement of the dosing member with respect to the housing upon setting a zero dose, wherein the zero stop feature is provided at the housing.

33. The drug delivery device according to embodiment 32,
 wherein the dosing member is rotationally movable with respect to the dose setting member during dose delivery.

34. The drug delivery device according to one of embodiments 32 and 33,
 wherein the zero dose stop engages with the zero stop feature in a contact plane that is angled with respect to a radial plane perpendicular to the longitudinal axis, wherein, for example, the contact plane is orientated perpendicular to the radial plane.

35. The drug delivery device according to one of embodiments 32 to 34,
 wherein the zero dose stop of the dosing member comprises a stop surface that is configured to abut against a corresponding stop surface of the housing.

36. The drug delivery device according to one of embodiments 32 to 35,
 wherein the zero dose stop is provided at a proximal end of the dosing member and/or wherein the zero stop feature is provided at a proximal end of a housing cavity of the housing.

The invention is further described by the following embodiments:

1. A drug delivery device (10, 200, 220, 222, 225) with a housing (3, 43, 210, 221, 223, 226), which is configured to connect to a dispensing unit (410, 420, 430, 440) comprising a compartment (81) containing a fluid,
 a piston rod (42, 240) configured to move in a proximal direction for ejecting the fluid, and
 a dosing mechanism (30, 230),
 wherein the dosing mechanism (30, 230) comprises an actuation member (31, 230) to be actuated by a user for advancing the piston rod (42, 240) and to thereby eject a set dose out of the compartment (81) and
 a conversion mechanism, which is configured to convert a movement of the actuation member (31, 230) to a movement of the piston rod (42, 240),
 wherein the conversion mechanism comprises a dose selector member (35, 310), which is rotationally fixed to the housing (3, 43, 210, 221, 223, 226) and axially movable with respect to the housing (3, 43, 210, 221, 223, 226), and a dosing member (330), which is rotationally movable with respect to the dose selector member (35, 310),
 wherein the dose selector member (35, 310) is provided between the actuation member (31, 230) and the dosing member (330),
 wherein the drug delivery device (10, 200, 220, 222, 225) comprises a friction reduction mechanism, which is provided between the dose selector member (35, 310) and the dosing member (330) to reduce friction between the dose selector member (35, 310) and the dosing member (330) upon relative rotational movement with respect to each other.

2. The drug delivery device (10, 200, 220, 222, 225) according to embodiment 1,
 wherein the friction reduction mechanism comprises a bearing element (370, 380), for example a ball bearing.

3. The drug delivery device (10, 200, 220, 222, 225) according to embodiment 2,
 wherein the bearing element (370, 380) is configured as an individual component separate from the dose selector member (35, 310) and/or the dosing member (330).

4. The drug delivery device (10, 200, 220, 222, 225) according to one of embodiments 2 and 3,
 wherein the bearing element (370, 380) is configured to rotate with respect to dose selector member (35, 310) and/or dosing member (330).

5. The drug delivery device (10, 200, 220, 222, 225) according to one of embodiments 2 to 4,
 wherein the bearing element (370, 380) is axially restrained between the dose selector member (35, 310) and the dosing member (330).

6. The drug delivery device (10, 200, 220, 222, 225) according to one of the preceding embodiments,
 wherein the dose selector member (35, 310) is axially restrained with respect to the dosing member (330),
 wherein the friction reduction mechanism is sandwiched between the dosing member (330) and the dose selector member (35, 310).

7. The drug delivery device (10, 200, 220, 222, 225) according to one of the preceding embodiments,
 wherein the dose selector member (35, 310) is connected to the dosing member (330) by a snap-on connector (318) that restricts relative movement between the dose selector member (35, 310) and the dosing member (330) in the axial direction and allows for relative rotational movement between the dose selector member (35, 310) and the dosing member (330).

8. The drug delivery device (10, 200, 220, 222, 225) according to one of the preceding embodiments,
 wherein the friction reduction mechanism is provided at a distal end of the dosing member (330).

9. The drug delivery device (10, 200, 220, 222, 225) according to one of the preceding embodiments,
 wherein the dose selector member (35, 310) comprises a contact surface (314) which is in contact with the friction reduction mechanism.

10. The drug delivery device (10, 200, 220, 222, 225) according to embodiment 9,
wherein the contact surface (314) comprises a ring shape and/or is provided at an inner surface of the dose selector member (35, 310).
11. The drug delivery device (10, 200, 220, 222, 225) according to one of the preceding embodiments,
wherein the dosing member (330) is partially located inside the dose selector member (35, 310).
12. The drug delivery device (10, 200, 220, 222, 225) according to one of the preceding embodiments,
wherein the dosing member (330) is coupled to the housing (3, 43, 210, 221, 223, 226) via a threaded connection (334) that translates rotation of the dosing member (330) into axial movement of the dosing member (330) with respect to the housing (3, 43, 210, 221, 223, 226).
13. The drug delivery device (10, 200, 220, 222, 225) according to one of the preceding embodiments,
wherein the actuation member (31, 230) is axially movable with respect to the dose selector member (35, 310) and configured to move towards the dose selector member (35, 310) when being actuated by a user.
14. The drug delivery device (10, 200, 220, 222, 225) according to one of the preceding embodiments,
wherein the actuation member (31, 230) is rotationally movable with respect to the dose selector member (35, 310), for example for setting the dose to be injected.
15. The drug delivery device (10, 200, 220, 222, 225) according to one of the preceding embodiments,
wherein the conversion mechanism further comprises a nut (36, 250), and a driver (41, 360),
wherein the nut (36, 250) is threadedly engaged with the piston rod (42, 240) and rotationally fixed to the housing (3, 43, 210, 221, 223, 226) during injection of the set dose,
wherein the driver (41, 360) is rotatable and axially movable with respect to the housing (3, 43, 210, 221, 223, 226) during injection and configured to axially advance the nut (36, 250) during injection.
16. The drug delivery device (10, 200, 220, 222, 225) according to embodiment 15,
wherein the conversion mechanism comprises a further friction reduction mechanism,
wherein the further friction reduction mechanism is provided between the nut (36, 250) and the driver (41, 360) to reduce friction therebetween during injection.
17. The drug delivery device (10, 200, 220, 222, 225) according to embodiment 16,
wherein the further friction reduction mechanism is a bearing (370, 380), for example a disc bearing.
18. The drug delivery device (10, 200, 220, 222, 225) according to one of embodiments 15 to 17,
wherein the driver (41, 360) is connected to the nut (36, 250) via a connection (354) which limits axial movement between the driver (41, 360) and the nut (36, 250).
19. The drug delivery device (10, 200, 220, 222, 225) according to embodiment 18,
wherein the connection (354) is provided at a distal end of the driver (41, 360).
20. The drug delivery device (10, 200, 220, 222, 225) according to one of embodiments 18 and 19,
wherein the connection (354) is configured as a snap connector.
21. The drug delivery device (10, 200, 220, 222, 225) according to one of embodiments 15 to 20,
wherein the driver (41, 360) is rotationally fixed with respect to the dosing member (330).
22. The drug delivery device (10, 200, 220, 222, 225) according to one of embodiments 15 to 21,
wherein the driver (41, 360) is coupled to the housing (3, 43, 210, 221, 223, 226) via a threaded connection (352) that translates rotational movement of the driver (41, 360) into axial movement.
23. A drug delivery device (10, 200, 220, 222, 225) with a housing (3, 43, 210, 221, 223, 226), which is configured to connect to a dispensing unit (410, 420, 430, 440) comprising a compartment (81) containing a fluid,
a piston rod (42, 240) configured to move in a proximal direction out of the housing (3, 43, 210, 221, 223, 226) for ejecting the fluid, and
a dosing mechanism (30, 230),
wherein the dosing mechanism (30, 230) comprises an actuation member (31, 230) to be actuated by a user for advancing the piston rod (42, 240) and to thereby eject a set dose out of the compartment and a conversion mechanism, which is configured to convert a movement of the actuation member (31, 230) to a movement of the piston rod (42, 240),
wherein the conversion mechanism comprises a nut (36, 250) and a driver (41, 360),
wherein the nut (36, 250) is threadedly engaged with the piston rod (42, 240) and rotationally fixed to the housing (3, 43, 210, 221, 223, 226) during injection of the set dose,
wherein the driver (41, 360) is rotatable and axially movable with respect to the housing (3, 43, 210, 221, 223, 226) during injection and configured to axially advance the nut (36, 250) during injection,
wherein the conversion mechanism comprises a friction reduction mechanism,
wherein the friction reduction mechanism is provided between the nut (36, 250) and the driver (41, 360) to reduce friction therebetween during injection.
24. The drug delivery device (10, 200, 220, 222, 225) according to embodiment 23,
wherein the friction reduction mechanism comprises a bearing element (370, 380), for example a disc bearing.
25. The drug delivery device (10, 200, 220, 222, 225) according to embodiment 24,
wherein the bearing element (370, 380) is configured as a component that is separate from the nut (36, 250) and/or the driver (41, 360).
26. The drug delivery device (10, 200, 220, 222, 225) according to one of embodiments 24 and 25,
wherein the bearing element (370, 380) is configured to rotate with respect to the nut (36, 250) and/or the driver (41, 360).
27. The drug delivery device (10, 200, 220, 222, 225) according to one of embodiments 24 to 26,
wherein the bearing element (370, 380) is axially restrained between the nut (36, 250) and the driver (41, 360).
28. The drug delivery device (10, 200, 220, 222, 225) according to one of embodiments 23 to 27,
wherein the nut (36, 250) is connected to the driver (41, 360) by a connection (354), such as a snap-on connection, that restricts relative movement between the nut (36, 250) and the driver (41, 360) in the axial direction.
29. The drug delivery device (10, 200, 220, 222, 225) according to one of embodiments 23 to 28,
    wherein the friction reduction mechanism is provided at a proximal end of the driver (41, 360).
30. The drug delivery device (10, 200, 220, 222, 225) according to one of embodiments 23 to 29,
    wherein a proximal front surface of the driver (41, 360) rests against an element of the friction reduction mechanism, such as a bearing element (370, 380).
31. The drug delivery device (10, 200, 220, 222, 225) according to one of embodiments 23 to 30,
    wherein the friction reduction mechanism is provided at a proximal end of the nut (36, 250).
32. The drug delivery device (10, 200, 220, 222, 225) according to one of embodiments 23 to 31,
    wherein the friction reduction mechanism rests against a proximal protrusion (253) of the nut (36, 250).
33. The drug delivery device (10, 200, 220, 222, 225) according to one of embodiments 23 to 32,
    wherein the driver (41, 360) is connected to the nut (36, 250) via a connection (354) which limits axial movement between the driver (41, 360) and the nut (36, 250).
34. The drug delivery device (10, 200, 220, 222, 225) according to embodiment 33,
    wherein the connection (354) is provided at a distal end of the driver (41, 360).
35. The drug delivery device (10, 200, 220, 222, 225) according to one of embodiments 33 and 34,
    wherein the connection (354) is configured as a snap fit connector.
36. The drug delivery device (10, 200, 220, 222, 225) according to one of embodiments 23 to 35,
    wherein the driver (41, 360) is rotationally fixed with respect to the dosing member (330).
37. The drug delivery device (10, 200, 220, 222, 225) according to one of embodiments 23 to 36,
    wherein the driver (41, 360) is coupled to the housing (3, 43, 210, 221, 223, 226) via a threaded connection (352) that translates rotational movement of the driver (41, 360) into axial movement.

What is claimed:
1. A drug delivery device, comprising:
   a housing configured to connect to a dispensing unit, the dispensing unit comprising a compartment containing a fluid;
   a piston rod configured to move in a proximal direction for ejecting the fluid; and
   a dosing mechanism,
   the dosing mechanism comprising an actuation member to be actuated by a user to advance the piston rod and to thereby eject a set dose out of the compartment and
   a conversion mechanism configured to convert movement of the actuation member to movement of the piston rod,
   the conversion mechanism comprising a dose selector member rotationally fixed to the housing and axially movable with respect to the housing, and a dosing member rotationally movable with respect to the dose selector member,
   the dose selector member disposed between the actuation member and the dosing member, the drug delivery device comprising a friction reduction mechanism disposed between the dose selector member and the dosing member to reduce friction between the dose selector member and the dosing member upon relative rotational movement with respect to each other.
2. The drug delivery device according to claim 1, wherein the friction reduction mechanism comprises a bearing element, and the bearing element is an individual component separate from the dose selector member or the dosing member.
3. The drug delivery device to claim 2, wherein the bearing element is configured to rotate with respect to the dose selector member or the dosing member, or the bearing element is axially restrained between the dose selector member and the dosing member.
4. The drug delivery device according to claim 1, wherein the dose selector member is axially restrained with respect to the dosing member, the friction reduction mechanism is sandwiched between the dosing member and the dose selector member, the dose selector member is connected to the dosing member by a connector configured to restrict relative movement between the dose selector member and the dosing member in an axial direction and enables relative rotational movement between the dose selector member and the dosing member.
5. The drug delivery device according to claim 1, wherein the friction reduction mechanism is provided at a distal end of the dosing member, or the dose selector member comprises a contact surface in contact with the friction reduction mechanism, and the contact surface comprises a ring shape or is provided at an inner surface of the dose selector member.
6. The drug delivery device according to claim 1, wherein the dosing member is partially disposed inside the dose selector member or the dosing member is coupled to the housing via a threaded connection configured to translate rotation of the dosing member into axial movement of the dosing member with respect to the housing.
7. The drug delivery device according to claim 1, wherein the actuation member is axially movable with respect to the dose selector member and configured to move towards the dose selector member when actuated by a user, or the actuation member is rotationally movable with respect to the dose selector member to set the dose to be injected.
8. The drug delivery device according to claim 1, wherein the conversion mechanism further comprises a nut, and a driver,
   the nut being threadedly engaged with the piston rod and rotationally fixed to the housing during delivery of the set dose, and the driver is rotatable and axially movable with respect to the housing during dose delivery and configured to axially advance the nut during dose delivery.
9. The drug delivery device according to claim 8, wherein the friction reduction mechanism is a first friction reduction mechanism, and the conversion mechanism comprises a second friction reduction mechanism, the second friction reduction mechanism is disposed between the nut and the driver to reduce friction therebetween during dose delivery, and the second friction reduction mechanism is a bearing.
10. The drug delivery device according to claim 8, wherein the driver is connected to the nut via a connection which limits axial movement between the driver and the nut, the connection provided at a distal end of the driver, or the connection is a snap connector.
11. The drug delivery device according to claim 8, wherein the driver is rotationally fixed with respect to the dosing member, or the driver is coupled to the housing via a threaded connection configured to translate rotational movement of the driver into axial movement.

12. The drug delivery device according to claim 2, wherein the bearing element is a ball bearing.

13. A drug delivery device, comprising:
a housing configured to connect to a dispensing unit comprising a compartment containing a fluid;
a piston rod configured to move in a proximal direction to eject the fluid; and
a dosing mechanism, the dosing mechanism comprising an actuation member to be actuated by a user to advance the piston rod and to thereby eject a set dose out of the compartment and a conversion mechanism configured to convert movement of the actuation member to movement of the piston rod, the conversion mechanism comprising a nut and a driver, the nut threadedly engaged with the piston rod and rotationally fixed to the housing during delivery of the set dose, the driver rotatable and axially movable with respect to the housing during dose delivery and configured to axially advance the nut during dose delivery, the conversion mechanism comprising a friction reduction mechanism, the friction reduction mechanism disposed between the nut and the driver to reduce friction therebetween during dose delivery.

14. The drug delivery device according to claim 13, wherein the friction reduction mechanism comprises a bearing element, and the bearing element is a component separate from the nut or the driver.

15. The drug delivery device according to claim 14, wherein the bearing element is configured to rotate with respect to the nut or the driver, or
the bearing element is axially restrained between the nut and the driver, and
the nut is connected to the driver by a connection configured to restrict relative movement between the nut and the driver in the axial direction.

16. The drug delivery device according to claim 13, wherein the friction reduction mechanism is provided at a proximal end of the driver, a proximal front surface of the driver rests against the friction reduction mechanism, or
the friction reduction mechanism is provided at a proximal end of the nut, and the friction reduction mechanism rests against a proximal protrusion of the nut.

17. The drug delivery device according to claim 13, wherein the driver is connected to the nut via a connection configured to limit axial movement between the driver and the nut, the connection provided at a distal end of the driver, and the connection is a snap fit connector.

18. The drug delivery device according to claim 15, wherein the connected is a snap-on connection.

* * * * *